(12) United States Patent
Dumas et al.

(10) Patent No.: US 7,928,239 B2
(45) Date of Patent: Apr. 19, 2011

(54) INHIBITION OF RAF KINASE USING QUINOLYL, ISOQUINOLYL OR PYRIDYL UREAS

(75) Inventors: Jacques Dumas, Orange, CT (US); Bernd Riedl, Wuppertal (DE); Uday Khire, Hamden, CT (US); Jill E. Wood, Hamden, CT (US); Robert N. Sibley, North Haven, CT (US); Mary-Katherine Monahan, Hamden, CT (US); Joel Renick, Milford, CT (US); David E. Gunn, Hamden, CT (US); Timothy B. Lowinger, Nishinomiya (JP); William J. Scott, Guilford, CT (US); Roger A. Smith, Madison, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

(21) Appl. No.: 09/777,920

(22) Filed: Feb. 7, 2001

(65) Prior Publication Data

US 2002/0165394 A1 Nov. 7, 2002

Related U.S. Application Data

(63) Continuation-in-part of application No. 09/758,548, filed on Jan. 12, 2001, now abandoned, which is a continuation-in-part of application No. 09/425,228, filed on Oct. 22, 1999, now abandoned, which is a continuation-in-part of application No. 09/257,266, filed on Feb. 25, 1999, now abandoned.

(60) Provisional application No. 60/115,877, filed on Jan. 13, 1999.

(51) Int. Cl.
*C07D 401/02* (2006.01)
*A61K 31/44* (2006.01)
*A61K 31/47* (2006.01)

(52) U.S. Cl. ........ 546/152; 546/159; 546/180; 546/261; 546/264; 546/277.4; 514/277; 514/299; 514/311; 514/312; 514/313; 514/314

(58) Field of Classification Search .................. 546/152, 546/159, 180, 261, 264, 277.4; 514/277, 514/299, 311, 312, 313, 314
See application file for complete search history.

(56) References Cited

U.S. PATENT DOCUMENTS

| | | |
|---|---|---|
| 502,504 A | 8/1893 | Thoms |
| 1,742,156 A | 2/1931 | Fitzky |
| 2,046,375 A | 7/1936 | Goldstein et al. |
| 2,093,265 A | 9/1936 | Coffby et al. |
| 2,288,422 A | 6/1942 | Rohm |
| 2,649,476 A | 8/1953 | Martin |
| 2,683,082 A | 7/1954 | Hill et al. |
| 2,722,544 A | 11/1955 | Martin |
| 2,745,874 A | 5/1956 | Schetty et al. |
| 2,781,330 A | 2/1957 | Downey |
| 2,797,214 A | 6/1957 | Bossard |
| 2,867,659 A | 1/1959 | Model et al. |
| 2,877,268 A | 3/1959 | Applegate et al. |
| 2,960,488 A | 11/1960 | Tamblyn et al. |
| 2,973,386 A | 2/1961 | Weldon |
| 3,151,023 A | 9/1964 | Martin |
| 3,200,035 A | 8/1965 | Martin et al. |
| 3,230,141 A | 1/1966 | Frick et al. |
| 3,424,760 A | 1/1969 | Helsley et al. |
| 3,424,761 A | 1/1969 | Helsley et al. |
| 3,424,762 A | 1/1969 | Helsley et al. |
| 3,547,940 A | 12/1970 | Brantley |
| 3,646,059 A | 2/1972 | Brantley |
| 3,689,550 A | 9/1972 | Schellenbaum et al. |
| 3,743,498 A | 7/1973 | Brantley |
| 3,754,887 A | 8/1973 | Brantley |
| 3,823,161 A | 7/1974 | Lesser |
| 3,828,001 A | 8/1974 | Broad et al. |
| 3,860,645 A | 1/1975 | Nikawitz |
| 3,990,879 A | 11/1976 | Soper |
| 4,001,256 A | 1/1977 | Callahan et al. |
| 4,009,847 A | 3/1977 | Aldrich et al. |
| 4,042,372 A | 8/1977 | Harper |
| 4,062,861 A | 12/1977 | Yukinaga et al. |
| 4,071,524 A | 1/1978 | Banitt |
| 4,111,680 A | 9/1978 | Yukinaga et al. |
| 4,111,683 A | 9/1978 | Singer |
| 4,116,671 A | 9/1978 | Yukinaga et al. |
| 4,173,637 A | 11/1979 | Nishiyama et al. |
| 4,173,638 A | 11/1979 | Nishiyama et al. |
| 4,183,854 A | 1/1980 | Crossley |
| 4,212,981 A | 7/1980 | Yukinaga et al. |
| 4,240,820 A | 12/1980 | Dickore et al. |
| 4,405,644 A | 9/1983 | Kabbe et al. |

(Continued)

FOREIGN PATENT DOCUMENTS

| | | |
|---|---|---|
| CA | 2146707 | 10/1995 |
| DE | 0 487 014 | 12/1929 |
| DE | 0 511 468 | 10/1930 |
| DE | 0 523 437 | 5/1931 |
| DE | 2436179 | 2/1975 |
| DE | 2436179 A1 | 2/1975 |
| DE | 25 01 648 | 7/1975 |
| DE | 3305866 A1 | 2/1983 |
| DE | 35 29 747 A1 | 8/1985 |
| DE | 35 40 377 A1 | 11/1985 |

(Continued)

OTHER PUBLICATIONS

Dorwald F. A. Side Reactions in Organic Synthesis, 2005, Wiley: VCH, Weinheim p. IX of Preface.*

(Continued)

*Primary Examiner* — Rita J Desai
(74) *Attorney, Agent, or Firm* — Millen, White, Zelano & Branigan, P.C.

(57) ABSTRACT

This invention relates to the use of a group of aryl ureas in treating raf mediated diseases, and pharmaceutical compositions in such therapy.

18 Claims, No Drawings

U.S. PATENT DOCUMENTS

| | | | |
|---|---|---|---|
| 4,410,697 | A | 10/1983 | Török et al. |
| 4,437,878 | A | 3/1984 | Acker et al. |
| 4,468,380 | A | 8/1984 | O'Doherty et al. |
| 4,473,579 | A | 9/1984 | Devries et al. |
| 4,511,571 | A | 4/1985 | Böger et al. |
| 4,514,571 | A | 4/1985 | Nakai et al. |
| 4,526,997 | A | 7/1985 | O'Doherty et al. |
| 4,623,662 | A | 11/1986 | De Vries |
| 4,643,849 | A | 2/1987 | Hirai et al. |
| 4,740,520 | A | 4/1988 | Hallenbach et al. |
| 4,760,063 | A | 7/1988 | Hallenbach et al. |
| 4,808,588 | A | 2/1989 | King |
| 4,820,871 | A | 4/1989 | Kissener et al. |
| 4,863,924 | A | 9/1989 | Haga et al. |
| 4,983,605 | A | 1/1991 | Kondo et al. |
| 4,985,449 | A | 1/1991 | Haga et al. |
| 5,036,072 | A | 7/1991 | Nakajama et al. |
| 5,059,614 | A | 10/1991 | Lepage et al. |
| 5,098,907 | A | 3/1992 | Kondo et al. |
| 5,130,331 | A | 7/1992 | Pascual |
| 5,162,360 | A | 11/1992 | Creswell et al. |
| 5,185,358 | A | 2/1993 | Creswell et al. |
| 5,312,820 | A | 5/1994 | Ashton et al. |
| 5,319,099 | A | 6/1994 | Kamata et al. |
| 5,399,566 | A | 3/1995 | Katano et al. |
| 5,423,905 | A | 6/1995 | Fringeli |
| 5,429,918 | A | 7/1995 | Seto et al. |
| 5,432,468 | A | 7/1995 | Moriyama et al. |
| 5,470,882 | A | 11/1995 | Dixon et al. |
| 5,500,424 | A | 3/1996 | Nagamine et al. |
| 5,508,288 | A | 4/1996 | Forbes et al. |
| 5,547,966 | A * | 8/1996 | Atwal et al. ................. 514/352 |
| 5,597,719 | A | 1/1997 | Freed et al. |
| 5,696,138 | A | 12/1997 | Olesen et al. |
| 5,698,581 | A | 12/1997 | Kleemann et al. |
| 5,773,459 | A | 6/1998 | Tang et al. |
| 5,780,483 | A | 7/1998 | Widdowson et al. |
| 5,807,891 | A | 9/1998 | Bold et al. |
| 5,814,646 | A | 9/1998 | Heinz et al. |
| 5,886,044 | A | 3/1999 | Widdowson et al. |
| 5,891,895 | A | 4/1999 | Shiraishi et al. |
| 5,908,865 | A | 6/1999 | Doi et al. |
| 5,965,573 | A | 10/1999 | Petrie et al. |
| 6,004,965 | A | 12/1999 | Breu et al. |
| 6,005,008 | A | 12/1999 | Widdowson et al. |
| 6,020,345 | A | 2/2000 | Vacher et al. |
| 6,040,339 | A | 3/2000 | Yoshida et al. |
| 6,080,763 | A | 6/2000 | Regan et al. |
| 6,093,742 | A | 7/2000 | Salituro et al. |
| 6,133,319 | A | 10/2000 | Widdowson |
| 6,150,415 | A | 11/2000 | Hammock et al. |
| 6,174,901 | B1 | 1/2001 | Mantlo et al. |
| 6,180,675 | B1 | 1/2001 | Widdowson et al. |
| 6,187,799 | B1 | 2/2001 | Wood et al. |
| 6,211,373 | B1 | 4/2001 | Widdowson et al. |
| 6,218,539 | B1 | 4/2001 | Widdowson |
| 6,242,601 | B1 | 6/2001 | Breu et al. |
| 6,262,113 | B1 | 7/2001 | Widdowson et al. |
| 6,271,261 | B1 | 8/2001 | Widdowson |
| 6,333,341 | B1 | 12/2001 | Mantlo et al. |
| 6,339,045 | B1 | 1/2002 | Kanno et al. |

FOREIGN PATENT DOCUMENTS

| | | | |
|---|---|---|---|
| DE | 3529247 | A1 | 11/1986 |
| DE | 3540377 | A1 | 5/1987 |
| EP | 16371 | | 3/1980 |
| EP | 0016371 | A1 | 10/1980 |
| EP | 0116932 | A1 | 8/1984 |
| EP | 0202538 | A1 | 11/1986 |
| EP | 242666 | | 10/1987 |
| EP | 0242666 | A1 | 10/1987 |
| EP | 335156 | | 3/1989 |
| EP | 371876 | | 11/1989 |
| EP | 425443 | | 10/1990 |
| EP | 0 405 233 | | 1/1991 |
| EP | 459887 | | 5/1991 |
| EP | 0 502 504 | A1 | 9/1992 |
| EP | 0676395 | A2 | 10/1995 |
| EP | 676395 | | 7/1996 |
| EP | 0 860 433 | A1 | 8/1998 |
| EP | 0860433 | A1 | 8/1998 |
| FR | 1 457 172 | | 9/1966 |
| GB | 0 828 231 | | 10/1956 |
| GB | 0 771 333 | | 3/1957 |
| GB | 0 921 682 | | 3/1963 |
| GB | 1590870 | | 6/1981 |
| GB | 0 253 997 | | 2/1988 |
| JP | 44 2569 | | 2/1969 |
| JP | 50-77375 | | 6/1975 |
| JP | 60-76072 | | 6/1975 |
| JP | 50-149668 | | 11/1975 |
| JP | 06317051 | | 1/1976 |
| JP | 51-80862 | | 7/1976 |
| JP | 08603353 | | 7/1978 |
| JP | 55 98152 | | 7/1980 |
| JP | 55-124763 | | 9/1980 |
| JP | 55-162772 | | 12/1980 |
| JP | 56029871 | | 7/1981 |
| JP | 5821626 | | 5/1983 |
| JP | 3 532 47 | | 3/1991 |
| JP | 8 301841 | | 11/1996 |
| JP | 10-306078 | | 11/1998 |
| WO | 96/02112 | | 3/1990 |
| WO | 93/18028 | | 9/1993 |
| WO | 93/24458 | | 12/1993 |
| WO | 94/14801 | | 7/1994 |
| WO | 94/18170 | | 8/1994 |
| WO | 94 22807 | | 10/1994 |
| WO | 94/25012 | | 11/1994 |
| WO | 95/02591 | | 1/1995 |
| WO | 95/07922 | | 3/1995 |
| WO | 95/13067 | | 5/1995 |
| WO | 95/31451 | | 11/1995 |
| WO | 95/33458 | | 12/1995 |
| WO | WO 96/10559 | | 4/1996 |
| WO | 96/25157 | A1 | 8/1996 |
| WO | 96/40673 | | 12/1996 |
| WO | 96/40675 | A1 | 12/1996 |
| WO | WO 97/17329 | | 5/1997 |
| WO | 97/29743 | | 8/1997 |
| WO | WO 97/30992 | | 8/1997 |
| WO | 97/40028 | A1 | 10/1997 |
| WO | 97/45400 | | 12/1997 |
| WO | 97/49399 | | 12/1997 |
| WO | 97/49400 | | 12/1997 |
| WO | WO 98/17267 | | 4/1998 |
| WO | 98/22103 | | 5/1998 |
| WO | 98/22432 | | 5/1998 |
| WO | WO 98/22103 | | 5/1998 |
| WO | 98/52559 | | 11/1998 |
| WO | WO 98/52558 | | 11/1998 |
| WO | WO 98/52559 | | 11/1998 |
| WO | WO 99/33458 | | 11/1998 |
| WO | 99/00357 | | 1/1999 |
| WO | 99/00370 | | 1/1999 |
| WO | WO 99/32110 | | 4/1999 |
| WO | 99/23091 | | 5/1999 |
| WO | 99/24398 | | 5/1999 |
| WO | WO 99/23091 | | 5/1999 |
| WO | WO 99/24398 | | 5/1999 |
| WO | 99/32111 | | 7/1999 |
| WO | 99/32437 | * | 7/1999 |
| WO | 99/32455 | | 7/1999 |
| WO | WO 99/32106 | | 7/1999 |
| WO | WO 99/32111 | | 7/1999 |
| WO | WO 99/32436 | | 7/1999 |
| WO | WO 99/32437 | | 7/1999 |
| WO | WO 99/32455 | | 7/1999 |
| WO | WO 99/32463 | | 7/1999 |
| WO | 00/17175 | | 9/1999 |
| WO | WO 00/17175 | | 9/1999 |
| WO | 00/43384 | | 7/2000 |
| WO | WO 00/43366 | | 7/2000 |
| WO | WO 00/43384 | | 7/2000 |
| WO | 00/47577 | * | 8/2000 |
| WO | 00/55139 | | 9/2000 |

| | | |
|---|---|---|
| WO | 00/55152 | 9/2000 |
| WO | WO 00/55139 | 9/2000 |
| WO | WO 00/55152 | 9/2000 |

OTHER PUBLICATIONS

Side Reaction p. 8 and (9, Dorwald , 2005.*
O. McDonald et al , Aza Stilbenes . . . 2006 Bioorganic Medical Chemical Letters, 5378-5383.*
Dumas, J., "CAS Substructure," May 6, 1997, pp. 1-29.
Scott, Bill, "Substructure (Patent Families)," Aug. 11, 1997, pp. 1-19.
Scott, Bill, "Substructure #2," Nov. 25, 1997, pp. 1-3.
"Beilstein number" Collection, 28 pages.
"Beilstein Collection," 4 pages.
Scott, Bill, "Substructure Search," Dec. 2, 1997, pp. 1-51.
Substructure Search, pp. 1-30.
Derwent World Patents Index Search, pp. 20-26.
Abstract of EP 116,932.
Abstract of EP 676,395.
Abstract of EP 202,538.
Abstract of EP 16,371.
Avruch et al., "Raf meets Ras: completing the framework of a signal transduction pathway", TIBS 19; Jul. 1994; pp. 279-2823.
White, A. D., et al. "Heterocyclic Ureas: Inhibitors of Acyl-CoA:Cholesterol O-Acyltransferase as Hypochelesterolemic Agents," Jun. 6, 1996, pp. 4382-4395.
Audia, James E. et al., "Potent, Selective Tetraphdro-β-carboline Antagonists of the Serotonin 2B ($5HT_{2B}$) Contractile Receptor in the Rat Stomach Fundus, " Jan. 22, 1996, pp. 2773-2780.
Forbes, Ian T., "N-(1-Methyl-5-indolyl)-n'-(3-methyl-5-isothiazolyl)urea: A Novel, High-Affinity $5-HT_{2B}$ Receptor Antagonist," Mar. 17, 1995, pp. 855-857.
Boulton, A. J., et al.,"Heterocyclic Rearrangements. Part X.[1] A Generalised Monocyclic Rearrangement," 1967, 2005-07.
N. S. Magnuson, et al., "The Raf-1 serine/threonine protein kinase," Cancer Biology, vol. 5, 1994, pp. 247-253.
G. Daum, et al., The ins and outs of Raf Kinases,: TIBS Nov. 19, 1994, pp. 474-480.
W. Kolch, et al., "Raf-1 protein kinase is required for growth of induced NIH/3T3 cells," Letters to Nature, vol. 349, Jan. 31, 1991, p. 226-28.
M. Fridman, et al., "The Minimal Fragments of c-Raf-1 and NF1 That Can Suppress v-Ha-Ras-Induced Malignant Phenotype," The Journal of Biological Chemistry, vol. 269, No. 48, Dec. 2, 1994; pp. 30105-30108.
G. L. Bolton, et al., Chapter 17. Ras Oncogene Directed Approaches in Cancer Chemotherapy, Annual Reports In Medicinal Chemistry, vol. 29, 1994, pp. 165-174.
J. L. Bos, "ras Oncogenes in Human Cancer: A Review," Cancer Research, vol. 49, Sep. 1, 1989, pp. 4682-4689.
Michaelis, Justus, Liebigs Ann. Chem. (JLACBF) 397, 1913, 143.
B. P. Monia, et al., "Antitumor activity of a phosphorothioate antisense oligodeopxynucleotide targeted against C-rat kinase," Nature Medicine, vol. 2, No. 6, Jun. 1996, pp. 668-675.
Lee, et al., Bicyclic Imidazoles as a Novel Class of Cytokine Biosynthesis Inhiibitors, N.Y. Academy of Science, 1993, pp. 149-170.
F. Lepage, et al., "New N-aryl isoxazolecarboxamides and N-isoxazolybenzamides as anticonvulsant agents," Eur. J. Med. Chem, vol. 27, 1992, pp. 581-593.
Ridley, et al., "Actions of IL-1 are Selectively Controlled by p38 Mitogen-Activated Protein Kinase," The American Association of Immunologists, 1997, p. 3165-73.
Chemical Abstract, vol. 116, No. 21, 25 May 1992, pp. 741-742.

Tarzia, G. et al. Whythesis and anti-inflammatory properties of some pyrrolo(1H,3H)[3,4]pyrimidin-2-ones and pyrrolo(1H,3H)[3,4-d]pyurimidin-2-ones and pyrrolo(1H,3H)-pyrimidin-2-ones. Chemical Abstracts. Aug. 27, 1979, No. 74558p; p. 594.
U.S. Appl. No. 08/863,021, May 23, 1997, RAF Kinase Inhibitors.
U.S. Appl. No. 08/863,022, May 23, 1997, RAF Kinase Inhibitors.
Unassigned, Dec. 22, 1998, Inhibition of RAF Kinase Using Symmetrical Substituted Diphenyl Ureas.
U.S. Appl. No. 09/479,125, filed Dec. 22, 1998, Inhibition of RAF Kinase Using Substituted Heterocyclic Ureas (Abandoned in favor of Bayer 8C1 U.S. Appl. No. 09/640,780, filed Aug. 18, 2000).
U.S. Appl. No. 09/472,232, filed Dec. 27, 1998, Inhibition of RAF Kinase Using Aryl and Heteroaryl Substituted Heterocyclic Ureas.
U.S. Appl. No. 09/458,015, filed Dec. 10, 1999, Inhibition of P38 Kinase Activity Using Symmetrical and Unsymmetrical Diphenyl Ureas.
U.S. Appl. No. 09/458,014, filed Dec. 10, 1999, Inhibition of P38 Kinase Activity Using Substituted Heterocyclic Ureas.
Unassigned, Dec. 22, 1998, Inhbition of RAF Kinase Using Aryl and Heteroaryl Substituted Heterocyclic Ureas.
U.S. Appl. No. 09/425,229, filed Oct. 22, 1999, ω-Carboxy Arly Substituted Diphenyl Ureas P38 Kinase Inhibitors.
F. Russo, Sintesi Di Derivati 2,6-Sostituiti Del 5H-1,3,5-Tiadiazolo[3,2-a]-s-Triazina-5,7-Dione, 1978, pp. 972-983.
Odette Foussard-Blanpin, Etude pharmacodynamique comparee de carboxamides diversement substitutes dans le domaine du systeme nerveux central; 1982; pp. 339-350.
Joseph T. Bruder and Imre Kovesdi, "Adenovirus Infection Stimulates the Raf/MAPK Signaling Pathway and Induces Interleukin-8 Expression", May 17, 1996, pp. 398-404.
Abstract (Basic): EP 4931 A, Apr. 21, 1978.
Caplus 95:61995, Abstract JP 55162772, Substituted acetic derivatives, Shionogi & Co., May 23, 1980.
Caplus 86:72448, Abstract JP 57053785, Pyridine derivatives, Maeda Ryozo et al., Nov. 15, 1982.
Caplus 84:180049, Abstract JP 56029871, Hamada Yoshinori et al., Jul. 10, 1981.
Caplus 84:43857, Abstract JP 58021626, Maeda Ryozo et al., May 2, 1983.
Murata et la., Chemical and Pharmaceutical Bulletin, vol. 22, 1974, p. 1212.
Garcia-Lopez et al., Journal of the American Chemical Society, vol. 1978, 1978, pp. 438-537.
Hiroshi Kubo et al., Herbicidal Activity of 1,3,4-Thiadiazole Derivatives, 1970, pp. 60-65.
Abstract of DE 3305866 A, Aug. 23, 1986.
Abstract of EP 202,538, Nov. 26, 1886.
Abstract of EP 676,395 (U.S. equivalent 5,698,581).
Abstract of EP 4931 (U.S. equivalent 4,240,820).
Kubo, Hiroshi et al: "herbicidal activity . . . " J. Agr. Food Chem, (1970), 18(1), 60-5.
Russo, F. et al. "Synthesis of 2,6-substituted derivatives of 5H-1,3,4-thiadiazolo'3,2-a!-s triazine-5,7-dione" FARMACO, ED.SCI. (1978), 33(12), 972-83.
Foussard-Blanpin, Odette: "Comparative pharmacodynamic study of variously substituted carboxamides of the central nervous ststem" Ann. Pharm. Fr. (1982), 40 (4), 339-50.
Grant, A.M et al.: "Hypotensive thiadiazoles" J.Med. Chem. (1972), 15(10), 1082-4.

* cited by examiner

US 7,928,239 B2

INHIBITION OF RAF KINASE USING QUINOLYL, ISOQUINOLYL OR PYRIDYL UREAS

CROSS REFERENCE TO RELATED APPLICATIONS

This is a continuation-in-part of Ser. No. 09/758,548 filed Jan. 12, 2001 now abandoned, which is a continuation-in-part of Ser. No. 09/425,228 filed Oct. 22, 1999 now abandoned, which is a continuation-in-part of Ser. No. 09/257,266 filed Feb. 25, 1999 now abandoned and which claims the benefit of priority of Provisional Application Ser. No. 60/115,877 filed Jan. 13, 1999.

FIELD OF THE INVENTION

This invention relates to the use of a group of aryl ureas in treating raf mediated diseases, and pharmaceutical compositions for use in such therapy.

BACKGROUND OF THE INVENTION

The $p21^{ras}$ oncogene is a major contributor to the development and progression of human solid cancers and is mutated in 30% of all human cancers (Bolton et al. *Ann. Rep. Med. Chem.* 1994, 29, 165-74; Bos. *Cancer Res.* 1989, 49, 4682-9). In its normal, unmutated form, the ras protein is a key element of the signal transduction cascade directed by growth factor receptors in almost all tissues (Avruch et al. *Trends Biochem. Sci.* 1994, 19, 279-83). Biochemically, ras is a guanine nucleotide binding protein, and cycling between a GTP-bound activated and a GDP-bound resting form is strictly controlled by ras' endogenous GTPase activity and other regulatory proteins. In the ras mutants in cancer cells, the endogenous GTPase activity is alleviated and, therefore, the protein delivers constitutive growth signals to downstream effectors such as the enzyme raf kinase. This leads to the cancerous growth of the cells which carry these mutants (Magnuson et al. *Semin. Cancer Biol.* 1994, 5, 247-53). It has been shown that inhibiting the effect of active ras by inhibiting the raf kinase signaling pathway by administration of deactivating antibodies to raf kinase or by co-expression of dominant negative raf kinase or dominant negative MEK, the substrate of raf kinase, leads to the reversion of transformed cells to the normal growth phenotype (see: Daum et al. *Trends Biochem. Sci.* 1994, 19, 474-80; Fridman et al. *J. Biol. Chem.* 1994, 269, 30105-8. Kolch et al. (*Nature* 1991, 349, 426-28) have further indicated that inhibition of raf expression by antisense RNA blocks cell proliferation in membrane-associated oncogenes. Similarly, inhibition of raf kinase (by antisense oligodeoxynucleotides) has been correlated in vitro and in vivo with inhibition of the growth of a variety of human tumor types (Monia et al., *Nat. Med.* 1996, 2, 668-75).

SUMMARY OF THE INVENTION

The present invention provides compounds which are inhibitors of the enzyme raf kinase. Since the enzyme is a downstream effector of $p21^{ras}$, the instant inhibitors are useful in pharmaceutical compositions for human or veterinary use where inhibition of the raf kinase pathway is indicated, e.g., in the treatment of tumors and/or cancerous cell growth mediated by raf kinase. In particular, the compounds are useful in the treatment of human or animal, e.g., murine cancer, since the progression of these cancers is dependent upon the ras protein signal transduction cascade and therefore susceptible to treatment by interruption of the cascade, i.e., by inhibiting raf kinase. Accordingly, the compounds of the invention are useful in treating solid cancers, such as, for example, carcinomas (e.g., of the lungs, pancreas, thyroid, bladder or colon, myeloid disorders (e.g., myeloid leukemia) or adenomas (e.g., villous colon adenoma).

The present invention, therefore, provides compounds generally described as aryl ureas, including both aryl and heteroaryl analogues, which inhibit the raf pathway. The invention also provides a method for treating a raf mediated disease state in humans or mammals. Thus, the invention is directed to compounds which inhibit the enzyme RAF kinase and also to compounds, compositions and methods for the treatment of cancerous cell growth mediated by raf kinase wherein a compound of Formula I is administered or a pharmaceutically acceptable salt thereof.

$$A\text{-}D\text{-}B \tag{I}$$

wherein
D is —NH—C(O)—NH—,
A is a substituted moiety of up to 40 carbon atoms of the formula: -L-(M-L$^1$)$_q$, where L is a 5 or 6 membered cyclic structure bound directly to D, L$^1$ comprises a substituted cyclic moiety having at least 5 members, M is a bridging group having at least one atom, q is an integer of from 1-3; and each cyclic structure of L and L$^1$ contains 0-4 members of the group consisting of nitrogen, oxygen and sulfur, and
B is a substituted or unsubstituted pyridyl, quinolinyl, isoquinolinyl group
wherein L$^1$ is substituted by at least one substituent selected from the group consisting of —SO$_2$R$_x$, —C(O)R$_x$ and —C(NR$_y$)R$_z$,
R$_y$ is hydrogen or a carbon based moiety of up to 24 carbon atoms optionally containing heteroatoms selected from N, S and O and optionally halosubstituted, up to per halo,
R$_z$ is hydrogen or a carbon based moiety of up to 30 carbon atoms optionally containing heteroatoms selected from N, S and O and optionally substituted by halogen, hydroxy and carbon based substituents of up to 24 carbon atoms, which optionally contain heteroatoms selected from N, S and O and are optionally substituted by halogen;
R$_x$ is R$_z$ or NR$_a$R$_b$ where R$_a$ and R$_b$ are
a) independently hydrogen,
a carbon based moiety of up to 30 carbon atoms optionally containing heteroatoms selected from N, S and O and optionally substituted by halogen, hydroxy and carbon based substituents of up to 24 carbon atoms, which optionally contain heteroatoms selected from N, S and O and are optionally substituted by halogen, or
—OSi(R$_f$)$_3$ where R$_f$ is hydrogen or a carbon based moiety of up to 24 carbon atoms optionally containing heteroatoms selected from N, S and O and optionally substituted by halogen, hydroxy and carbon based substituents of up to 24 carbon atoms, which optionally contain heteroatoms selected from N, S and O and are optionally substituted by halogen; or
b) R$_a$ and R$_b$ together form a 5-7 member heterocyclic structure of 1-3 heteroatoms selected from N, S and O, or a substituted 5-7 member heterocyclic structure of 1-3 heteroatoms selected from N, S and O substituted by halogen, hydroxy or carbon based substituents of up to 24 carbon atoms, which optionally contain heteroatoms selected from N, S and O and are optionally substituted by halogen; or
c) one of R$_a$ or R$_b$ is —C(O)—, a C$_1$-C$_5$ divalent alkylene group or a substituted C$_1$-C$_5$ divalent alkylene group bound to the moiety L to form a cyclic structure with at least 5 members, wherein the substituents of the substituted C$_1$-C$_5$ divalent alkylene group are selected from the group consisting of halogen, hydroxy, and carbon based substituents of up to 24 carbon atoms, which optionally contain heteroatoms selected from N, S and O and are optionally substituted by halogen;

where B is substituted, L is substituted or $L^1$ is additionally substituted, the substituents are selected from the group consisting of halogen, up to per-halo, and Wn, where n is 0-3;

wherein each W is independently selected from the group consisting of —CN, —$CO_2R^7$, —$C(O)NR^7R^7$, —$C(O)$—$R^7$, —$NO_2$, —$OR^7$, —$SR^7$, —$NR^7R^7$, —$NR^7C(O)OR^7$, —$NR^7C(O)R^7$, -Q-Ar, and carbon based moieties of up to 24 carbon atoms, optionally containing heteroatoms selected from N, S and O and optionally substituted by one or more substituents independently selected from the group consisting of —CN, —$CO_2R^7$, —$C(O)R^7$, —$C(O)NR^7R^7$, —$OR^7$, —$SR^7$, —$NR^7R^7$, —$NO_2$, —$NR^7C(O)R^7$, —$NR^7C(O)OR^7$ and halogen up to per-halo; with each $R^7$ independently selected from H or a carbon based moiety of up to 24 carbon atoms, optionally containing heteroatoms selected from N, S and O and optionally substituted by halogen, wherein Q is —O—, —S—, —$N(R^7)$—, —$(CH_2)_m$—, —$C(O)$—, —$CH(OH)$—, —$(CH_2)_mO$—, —$(CH_2)_mS$—, —$(CH_2)_mN(R^7)$—, —$O(CH_2)_m$— $CHX^a$—, $CX^a_2$—, —S—$(CH_2)_m$— and —$N(R^7)(CH_2)_m$—, where m=1-3, and $X^a$ is halogen; and Ar is a 5- or 6-member aromatic structure containing 0-2 members selected from the group consisting of nitrogen, oxygen and sulfur, which is optionally substituted by halogen, up to per-halo, and optionally substituted by $Z_{n1}$, wherein n1 is 0 to 3 and each Z is independently selected from the group consisting of —CN, —$CO_2R^7$, —$C(O)R^7$, —$C(O)NR^7R^7$, —$NO_2$, —$OR^7$, —$SR^7$—$NR^7R^7$, —$NR^7C(O)OR^7$, —$NR^7C(O)R^7$, and a carbon based moiety of up to 24 carbon atoms, optionally containing heteroatoms selected from N, S and O and optionally substituted by one or more substituents selected from the group consisting of —CN, —$CO_2R^7$, —$COR^7$, —$C(O)NR^7R^7$, —$OR^7$, —$SR^7$, —$NO_2$, —$NR^7R^7$, —$NR^7C(O)R^7$, and —$NR^7C(O)OR^7$, with $R^7$ as defined above.

$R_y$ is preferably hydrogen, $C_{1-10}$ alkyl, $C_{1-10}$ alkoxy, $C_{3-10}$ cycloalkyl having 0-3 heteroatoms, $C_{2-10}$ alkenyl, $C_{1-10}$ alkenoyl, $C_{6-12}$ aryl, $C_{3-12}$ hetaryl having 1-3 heteroatoms selected from N, S and O, $C_{7-24}$ aralkyl, $C_{7-24}$ alkaryl, substituted $C_{1-10}$ alkyl, substituted $C_{1-10}$ alkoxy, substituted $C_{3-10}$ cycloalkyl having 0-3 heteroatoms selected from N, S and O, substituted $C_{6-14}$ aryl, substituted $C_{3-12}$ hetaryl having 1-3 heteroatoms selected from N, S and O, substituted $C_{7-24}$ alkaryl or substituted $C_{7-24}$ aralkyl, where $R_y$ is a substituted group, it is substituted by halogen up to per halo, $R_z$ is preferably hydrogen, $C_{1-10}$ alkyl, $C_{1-10}$ alkoxy, $C_{3-10}$ cycloalkyl having 0-3 heteroatoms, $C_{2-10}$ alkenyl, $C_{1-10}$ alkenoyl, $C_{6-12}$ aryl, $C_{3-12}$ hetaryl having 1-3 heteroatoms selected from, S, N and O, $C_{7-24}$ alkaryl, $C_{7-24}$ aralkyl, substituted $C_{1-10}$ alkyl, substituted $C_{1-10}$ alkoxy, substituted $C_{6-14}$ aryl, substituted $C_{3-10}$ cycloalkyl having 0-3 heteroatoms selected from S, N and O, substituted $C_{3-12}$ hetaryl having 1-3 heteroatoms selected from S, N and O, substituted $C_{7-24}$ alkaryl or substituted $C_{7-24}$ aralkyl where $R_z$ is a substituted group, it is substituted by halogen up to per halo, hydroxy, $C_{1-10}$ alkyl, $C_{3-12}$ cycloalkyl having 0-3 heteroatoms selected from O, S and N, $C_{3-12}$ hetaryl having 1-3 heteroatoms selected from N, S and O, $C_{1-10}$ alkoxy, $C_{6-12}$ aryl, $C_{1-6}$ halo substituted alkyl up to per halo alkyl, $C_6$-$C_{12}$ halo substituted aryl up to per halo aryl, $C_3$-$C_{12}$ halo substituted cycloalkyl up to per halo cycloalkyl having 0-3 heteroatoms selected from N, S and O, halo substituted $C_3$-$C_{12}$ hetaryl up to per halo hetaryl having 1-3 heteroatoms selected from O, N and S, halo substituted $C_7$-$C_{24}$ aralkyl up to per halo aralkyl, halo substituted $C_7$-$C_{24}$ alkaryl up to per halo alkaryl, and —$C(O)R_g$ wherein $R_y$ is as defined below, $R_a$ and $R_b$ preferably are, a) independently hydrogen,
a carbon based moiety selected from to the group consisting of $C_1$-$C_{10}$ alkyl, $C_1$-$C_{10}$ alkoxy, $C_{3-10}$ cycloalkyl, $C_{2-10}$ alkenyl, $C_{1-10}$ alkenoyl, $C_{6-12}$ aryl, $C_{3-12}$ hetaryl having 1-3 heteroatoms selected from O, N and S, $C_{3-12}$ cycloalkyl having 0-3 heteroatoms selected from N, S and O, $C_{7-24}$ aralkyl, $C_{7-24}$ alkaryl, substituted $C_{1-10}$ alkyl, substituted $C_{1-10}$ alkoxy, substituted $C_{3-10}$ cycloalkyl, having 0-3 heteroatoms selected from N, S and O, substituted $C_{6-12}$ aryl, substituted $C_{3-12}$ hetaryl having 1-3 heteroatoms selected from N, S and O, substituted $C_{7-24}$ aralkyl, substituted $C_{7-24}$ alkaryl, where $R_a$ and $R_b$ are a substituted group, they are substituted by halogen up to per halo, hydroxy, $C_{1-10}$ alkyl, $C_{3-12}$ cycloalkyl having 0-3 heteroatoms selected from O, S and N, $C_{3-12}$ hetaryl having 1-3 heteroatoms selected from N, S and O, $C_{1-10}$ alkoxy, $C_{6-12}$ aryl, $C_{1-6}$ halo substituted alkyl up to per halo alkyl, $C_6$-$C_{12}$ halo substituted aryl up to per halo aryl, $C_3$-$C_{12}$ halo substituted cycloalkyl having 0-3 heteroatoms selected from N, S and O, up to per halo cycloalkyl, halo substituted $C_3$-$C_{12}$ hetaryl up to per halo hetaryl, halo substituted $C_7$-$C_{24}$ aralkyl up to per halo aralkyl, halo substituted $C_7$-$C_{24}$ alkaryl up to per halo alkaryl, and —$C(O)R_g$ wherein $R_g$ is as defined below; or —$OSi(R_f)_3$ where $R_f$ is hydrogen, $C_{1-10}$ alkyl, $C_{1-10}$ alkoxy, $C_3$-$C_{10}$ cycloalkyl having 0-3 heteroatoms selected from O, S and N, $C_{6-12}$ aryl, $C_3$-$C_{12}$ hetaryl having 1-3 heteroatoms selected from O, S and N, $C_{7-24}$ aralkyl, substituted $C_{1-10}$ alkyl, substituted $C_1$-$C_{10}$ alkoxy, substituted $C_3$-$C_{12}$ cycloalkyl having 0-3 heteroatoms selected from O, S and N, substituted $C_3$-$C_{12}$ hetaryl having 1-3 heteroatoms selected from O, S, and N, substituted $C_{6-12}$ aryl, and substituted $C_{7-24}$ alkaryl, where $R_f$ is a substituted group it is substituted halogen up to per halo, hydroxy, $C_{1-10}$ alkyl, $C_{3-12}$ cycloalkyl having 0-3 heteroatoms selected from O, S and N, $C_{3-12}$ hetaryl having 1-3 heteroatoms selected from N, S and O, $C_{1-10}$ alkoxy, $C_{6-12}$ aryl, $C_7$-$C_{24}$ alkaryl, $C_7$-$C_{24}$ aralkyl, $C_{1-6}$ halo substituted alkyl up to per halo alkyl, $C_6$-$C_{12}$ halo substituted aryl up to per halo aryl, $C_3$-$C_{12}$ halo substituted cycloalkyl having 0-3 heteroatoms selected from N, S and O, up to per halo cycloalkyl, halo substituted $C_3$-$C_{12}$ hetaryl up to per halo hetaryl, halo substituted $C_7$-$C_{24}$ aralkyl up to per halo aralkyl, halo substituted $C_7$-$C_{24}$ alkaryl up to per halo alkaryl, and —$C(O)R_g$ wherein $R_g$ is as defined below, or b) $R_a$ and $R_b$ together form a 5-7 member heterocyclic structure of 1-3 heteroatoms selected from N, S and O, or a substituted 5-7 member heterocyclic structure of 1-3 heteroatoms selected from N, S and O with substituents selected from the group consisting of halogen up to per halo, hydroxy, $C_{1-10}$ alkyl, $C_{3-12}$ cycloalkyl having 0-3 heteroatoms selected from O, S and N, $C_{3-12}$ hetaryl having 1-3 heteroatoms selected from N, S and O, $C_{1-10}$ alkoxy, $C_{6-12}$ aryl, $C_7$-$C_{24}$ alkaryl, $C_7$-$C_{24}$ aralkyl, halo substituted $C_{1-6}$ alkyl up to per halo alkyl, halo substituted $C_6$-$C_{12}$ aryl up to per halo aryl, halo substituted $C_3$-$C_{12}$ cycloalkyl having 0-3 heteroatoms selected from N, S and O, up to per halo cycloalkyl, halo substituted $C_3$-$C_{12}$ hetaryl up to per halo hetaryl, halo substituted $C_7$-$C_{24}$ aralkyl up to per halo aralkyl, halo substituted $C_7$-$C_{24}$ alkaryl up to per halo alkaryl, and —C(O)R$_g$ wherein R$_g$ is as defined below, or c) one of R$_a$ or R$_b$ is —C(O)—, a $C_1$-$C_5$ divalent alkylene group or a substituted $C_1$-$C_5$ divalent alkylene group bound to the moiety L to form a cyclic structure with at least 5 members, wherein the substituents of the substituted $C_1$-$C_5$ divalent alkylene group are selected from the group consisting of halogen, hydroxy, $C_{1-10}$ alkyl, $C_{3-12}$ cycloalkyl having 0-3 heteroatoms selected from O, S and N, $C_{3-12}$ hetaryl having 1-3 heteroatoms selected from N, S and O, $C_{1-10}$ alkoxy, $C_{6-12}$ aryl, $C_7$-$C_{24}$ alkaryl, $C_7$-$C_{24}$ aralkyl, $C_{1-6}$ halo substituted alkyl up to per halo alkyl, $C_6$-$C_{12}$ halo substituted aryl up to per halo aryl, $C_3$-$C_{12}$ halo substituted cycloalkyl having 0-3 heteroatoms selected from N, S and O, up to per halo cycloalkyl, halo substituted $C_3$-$C_{12}$ hetaryl up to per halo hetaryl, halo substituted $C_7$-$C_{24}$ aralkyl up to per halo aralkyl, halo substituted $C_7$-$C_{24}$ alkaryl up to per halo alkaryl, and —C(O)R$_g$ where R$_g$ is as defined below, where R$_g$ is $C_{1-10}$ alkyl; —CN, —CO$_2$R$_d$, —OR$_d$, —SR$_d$, —NO$_2$, —C(O) R$_e$, —NR$_d$R$_e$, —NR$_d$C(O)OR$_e$ and —NR$_d$C(O)R$_e$, and R$_d$ and R$_e$ are independently selected from the group consisting of hydrogen, $C_{1-10}$, alkyl, $C_{1-10}$ alkoxy, $C_{3-10}$ cycloalkyl having 0-3 heteroatoms selected from O, N and S, $C_{6-12}$ aryl, $C_3$-$C_{12}$ hetaryl with 1-3 heteroatoms selected from O, N and S and $C_7$-$C_{24}$ aralkyl, $C_7$-$C_{24}$ alkaryl, up to per halo substituted $C_1$-$C_{10}$ alkyl, up to per halo substituted $C_3$-$C_{10}$ cycloalkyl having 0-3 heteroatoms selected from O, N and S, up to per halo substituted $C_6$-$C_{14}$ aryl, up to per halo substituted $C_3$-$C_{12}$ hetaryl having 1-3 heteroatoms selected from O, N, and S, halo substituted $C_7$-$C_{24}$ alkaryl up to per halo alkaryl, and up to per halo substituted $C_7$-$C_{24}$ aralkyl, W is preferably independently selected from the group consisting of —CN, —CO$_2$R$^7$, —C(O)NR$^7$R$^7$, —C(O)—R$^7$, —NO$_2$, —OR$^7$, —SR$^7$, —NR$^7$R$^7$, —NR$^7$C(O)OR$^7$, —NR$^7$C(O)R$^7$, $C_1$-$C_{10}$ alkyl, $C_1$-$C_{10}$ alkoxy, $C_2$-$C_{10}$ alkenyl, $C_1$-$C_{10}$ alkenoyl, $C_3$-$C_{10}$ cycloalkyl having 0-3 heteroatoms selected from O, S and N, $C_6$-$C_{14}$ aryl, $C_7$-$C_{24}$ alkaryl, $C_7$-$C_{24}$ aralkyl, $C_3$-$C_{12}$ heteroaryl having 1-3 heteroatoms selected from O, N and S, $C_4$-$C_{23}$ alkheteroaryl having 1-3 heteroatoms selected from O, N and S, substituted $C_1$-$C_{10}$ alkyl, substituted $C_1$-$C_{10}$ alkoxy, substituted $C_2$-$C_{10}$ alkenyl, substituted $C_1$-$C_{10}$ alkenoyl, substituted $C_3$-$C_{10}$ cycloalkyl having 0-3 heteroatoms selected from O, N and S, substituted $C_6$-$C_{12}$ aryl, substituted $C_3$-$C_{12}$ hetaryl having 1-3 heteroatoms selected from O, N and S, substituted $C_7$-$C_{24}$ aralkyl, substituted $C_7$-$C_{24}$ alkaryl, substituted $C_4$-$C_{23}$ alkheteroaryl having 1-3 heteroatoms selected from O, N and S, and -Q-Ar;

R$^7$ is preferably independently selected from H, $C_1$-$C_{10}$ alkyl, $C_1$-$C_{10}$ alkoxy, $C_2$-$C_{10}$ alkenyl, $C_1$-$C_{10}$ alkenoyl, $C_3$-$C_{10}$ cycloalkyl having 0-3 heteroatoms selected from O, S and N, $C_6$-$C_{14}$ aryl, $C_3$-$C_{13}$ hetaryl having 1-3 heteroatoms selected from O, N and S, $C_7$-$C_{14}$ alkaryl, $C_7$-$C_{24}$ aralkyl, $C_4$-$C_{23}$ alkheteroaryl having 1-3 hetero atoms selected from O, N and S, up to per-halosubstituted $C_1$-$C_{10}$ alkyl, up to per-halosubstituted $C_3$-$C_{10}$ cycloalkyl having 0-3 heteroatoms selected from O, N and S, up to per-halosubstituted $C_6$-$C_{14}$ aryl, up to per-halosubstituted $C_3$-$C_{13}$ hetaryl having 1-3 heteroatoms selected from O, N and S, up to per-halosubstituted $C_7$-$C_{24}$ aralkyl, up to per-halosubstituted $C_7$-$C_{24}$ alkaryl, and up to per-halosubstituted $C_4$-$C_{23}$ alkheteroaryl; and Z is preferably independently selected from the group consisting of —CN, —CO$_2$R$^7$, —C(O)R$^7$, —C(O)NR$^7$R$^7$, —NO$_2$, —OR$^7$, —SR$^7$—NR$^7$R$^7$, —NR$^7$C(O)OR$^7$, —NR$^7$C(O)R$^7$, $C_1$-$C_{10}$ alkyl, $C_1$-$C_{10}$ alkoxy, $C_2$-$C_{10}$ alkenyl, $C_1$-$C_{10}$ alkenoyl, $C_3$-$C_{10}$ cycloalkyl having 0-3 heteroatoms selected from O, N and S, $C_6$-$C_{14}$ aryl, $C_3$-$C_{13}$ hetaryl having 1-3 heteroatoms selected from O, N and S, $C_7$-$C_{24}$ alkaryl, $C_7$-$C_{24}$ aralkyl, $C_4$-$C_{23}$ alkheteroaryl having 1-3 heteroatoms selected from O, N and S, substituted $C_1$-$C_{10}$ alkyl, substituted $C_1$-$C_{10}$ alkoxy, substituted $C_2$-$C_{10}$ alkenyl, substituted $C_1$-$C_{10}$ alkenoyl, substituted $C_3$-$C_{10}$ cycloalkyl having 0-3 heteroatoms selected from O, N and S, substituted $C_6$-$C_{12}$ aryl, substituted $C_7$-$C_{24}$ alkaryl, substituted $C_7$-$C_{24}$ aralkyl and substituted $C_4$-$C_{23}$ alkheteroaryl having 1-3 heteroatoms selected from O, N and S; wherein if Z is a substituted group, the one or more substituents are selected from the group consisting of —CN, —CO$_2$R$^7$, —COR$^7$, —C(O)NR$^7$R$^7$, —OR$^7$, —SR$^7$, —NO$_2$, —NR$^7$R$^7$, —NR$^7$C(O)R$^7$, and —NR$^7$C(O)OR$^7$, wherein R$^7$ is as defined above.

M is preferably one or more bridging groups selected from the group consisting of —O—, —S—, —N(R$^7$)—, —(CH$_2$)$_m$—, —C(O)—, —CH(OH)—, —(CH$_2$)$_m$O—, —(CH$_2$)$_m$S—, —(CH$_2$)$_m$N(R$^7$)—, —O(CH$_2$)$_m$—CHX$^a$—, —CX$^a{_2}$—, —S—(CH$_2$)$_m$— and —N(R$^7$)(CH$_2$)$_m$—, where m=1-3, X$^a$ is halogen and R$^7$ is as defined above.

Preferred compounds of Formula I include those wherein the cyclic structures of B and L bound directly to D are not substituted in the ortho position by —OH.

Where B of Formula I is a substituted pyridyl, substituted quinolinyl or isoquinolinyl group, B is preferably substituted 1 to 3 times by 1 or more substituents selected from the group consisting of —CN, halogen, $C_1$-$C_{10}$ alkyl, $C_1$-$C_{10}$ alkoxy, —OH, up to per halo substituted $C_1$-$C_{10}$ alkyl, up to per halo substituted $C_1$-$C_{10}$ alkoxy or phenyl substituted by halogen up to per halo.

In Formula I, suitable hetaryl groups include, but are not limited to, 5-12 carbon-atom aromatic rings or ring systems containing 1-3 rings, at least one of which is aromatic, in which one or more, e.g., 1-4 carbon atoms in one or more of the rings can be replaced by oxygen, nitrogen or sulfur atoms. Each ring typically has 3-7 atoms. For example, B can be 2- or 3-furyl, 2- or 3-thienyl, 2- or 4-triazinyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-oxadiazol-3- or -5-yl, 1,3,4-thiadiazol-2- or -5-yl, 1,3,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 1-, 3-, 4-, 5-, 6- or 7-benzothiazolyl, 2-, 4-, 5-, 6- or 7-benzisothiazolyl, 2-, 4-, 5-, 6- or 7-benz-1,3-oxadiazolyl, 2-, 3-, 4-, 5-, 6-, 7- or 8-quinolinyl, 1-, 3-, 4-, 5-, 6-, 7-, 8-isoquinolinyl, 1-, 2-, 3-, 4- or 9-carbazolyl, 1-, 2-, 3-, 4-, 5-, 6-, 7-, 8- or 9-acridinyl, or 2-, 4-, 5-, 6-, 7- or 8-quinazolinyl, or additionally optionally substituted phenyl, 2- or 3-thienyl, 1,3,4-thiadiazolyl, 3-pyrryl, 3-pyrazolyl, 2-thiazolyl or 5-thiazolyl, etc. For example, B can be 4-methyl-phenyl, 5-methyl-2-thienyl, 4-methyl-2-thienyl, 1-methyl-3-pyrryl, 1-methyl-3-pyrazolyl, 5-methyl-2-thiazolyl or 5-methyl-1,2,4-thiadiazol-2-yl.

Suitable alkyl groups and alkyl portions of groups, e.g., alkoxy, etc. throughout include methyl, ethyl, propyl, butyl, etc., including all straight-chain and branched isomers such as isopropyl, isobutyl, sec-butyl, tert-butyl, etc.

Suitable aryl groups which do not contain heteroatoms include, for example, phenyl and 1- and 2-naphthyl.

The term "cycloalkyl", as used herein, refers to cyclic structures with or without alkyl substituents such that, for example, "$C_4$ cycloalkyl" includes methyl substituted cyclopropyl groups as well as cyclobutyl groups. The term "cycloalkyl", as used herein also includes saturated heterocyclic groups.

Suitable halogen groups include F, Cl, Br, and/or I, from one to per-substitution (i.e. all H atoms on a group replaced by a halogen atom) being possible where an alkyl group is substituted by halogen, mixed substitution of halogen atom types also being possible on a given moiety.

The invention also relates to compounds per se, of formula I.

The present invention is also directed to pharmaceutically acceptable salts of formula I. Suitable pharmaceutically acceptable salts are well known to those skilled in the art and include basic salts of inorganic and organic acids, such as hydrochloric acid, hydrobromic acid, sulfuric acid, phosphoric acid, methanesulfonic acid, trifluoromethanesulfonic acid, benzenesulfonic acid, p-toluenesulfonic acid, 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid. In addition, pharmaceutically acceptable salts include acid salts of inorganic bases, such as salts containing alkaline cations (e.g., $Li^+Na^+$ or $K^+$), alkaline earth cations (e.g., $Mg^+2$, $Ca^+2$ or $Ba^+2$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, lysine, pyridine, N,N-dimethylaminopyridine (DMAP), 1,4-diazabiclo[2.2.2]octane (DABCO), 1,5-diazabicyclo[4.3.0]non-5-ene (DBN) and 1,8-diazabicyclo[5.4.0]undec-7-ene (DBU).

A number of the compounds of Formula I possess asymmetric carbons and can therefore exist in racemic and optically active forms. Methods of separation of enantiomeric and diastereomeric mixtures are well known to one skilled in the art. The present invention encompasses any racemic or optically active form of compounds described in Formula I which possess progesterone receptor binding activity.

General Preparative Methods

The compounds of Formula I may be prepared by the use of known chemical reactions and procedures, some from starting materials which are commercially available. Some of the compounds of Formula I are known in the art. Nevertheless, general preparative methods are provided below to aid one skilled in the art in synthesizing these compounds, with more detailed examples being provided in the Experimental section which follows.

Substituted and unsubstituted aminoquinolines, aminoisoquinolines and aminopyridines may be prepared using standard methods (see, for example: A. R. Katritsky et al. (Eds.). *Comprehensive Heterocyclic Chemistry II*, Vol. 5. M. H. Palmer. *Heterocyclic Compounds*; Arnold Ltd., London (1967). C. K. Esser et al. WO 96/18616. C. J. Donahue et al. *Inorg. Chem.* 30, 1991, 1588. E. Cho et al. WO 98/00402. A. Cordi et al. *Bioorg. Med. Chem.* 3, 1995, 129). In addition, many aminoquinolines, aminoisoquinolines and aminopyridines are commercially available.

Substituted anilines may be generated using standard methods (March. *Advanced Organic Chemistry*, 3$^{rd}$ Ed.; John Wiley: New York (1985). Larock. *Comprehensive Organic Transformations*; VCH Publishers: New York (1989)). As shown in Scheme I, aryl amines are commonly synthesized by reduction of nitroaryls using a metal catalyst, such as Ni, Pd, or Pt, and $H_2$ or a hydride transfer agent, such as formate, cyclohexadiene, or a borohydride (Rylander. *Hydrogenation Methods*; Academic Press: London, UK (1985)). Nitroaryls may also be directly reduced using a strong hydride source, such as $LiAlH_4$ (Seyden-Penne. *Reductions by the Alumino- and Borohydrides in Organic Synthesis*; VCH Publishers: New York (1991)), or using a zero valent metal, such as Fe, Sn or Ca, often in acidic media. Many methods exist for the synthesis of nitroaryls (March. *Advanced Organic Chemistry*, 3$^{rd}$ Ed.; John Wiley: New York (1985). Larock. *Comprehensive Organic Transformations*; VCH Publishers: New York (1989)).

Scheme I
Reduction of Nitroaryls to Aryl Amines

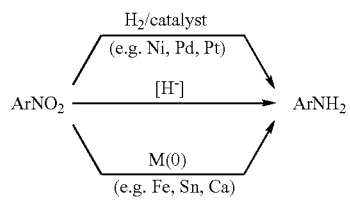

Nitroaryls are commonly formed by electrophilic aromatic nitration using $HNO_3$, or an alternative $NO_2^+$ source. Nitroaryls may be further elaborated prior to reduction. Thus, nitroaryls substituted with

potential leaving groups (e.g. F, Cl, Br, etc.) may undergo substitution reactions on treatment with nucleophiles, such as thiolate (exemplified in Scheme II) or phenoxide. Nitroaryls may also undergo Ullman-type coupling reactions (Scheme II).

Scheme II
Selected Nucleophilic Aromatic Substitution using Nitroaryls

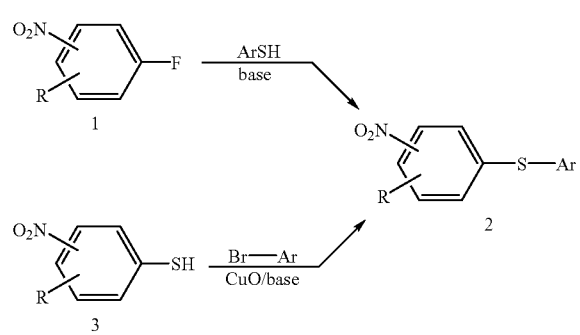

Nitroaryls may also undergo transition metal mediated cross coupling reactions. For example, nitroaryl electrophiles, such as nitroaryl bromides, iodides or triflates, undergo palladium mediated cross coupling reactions with aryl nucleophiles, such as arylboronic acids (Suzuki reactions, exemplified below), aryltins (Stille reactions) or arylzincs (Negishi reaction) to afford the biaryl (5).

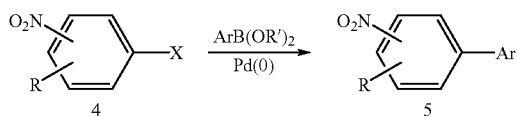

Either nitroaryls or anilines may be converted into the corresponding arenesulfonyl chloride (7) on treatment with chlorosulfonic acid. Reaction of the sulfonyl chloride with a fluoride source, such as KF then affords sulfonyl fluoride (8). Reaction of sulfonyl fluoride 8 with trimethylsilyl trifluoromethane in the presence of a fluoride source, such as tris (dimethylamino)sulfonium difluorotrimethylsiliconate (TASF) leads to the corresponding trifluoromethylsulfone (9). Alternatively, sulfonyl chloride 7 may be reduced to the arenethiol (10), for example with zinc amalgum. Reaction of thiol 10 with $CHClF_2$ in the presence of base gives the difluoromethyl mercaptan (11), which may be oxidized to the sulfone (12) with any of a variety of oxidants, including $CrO_3$-acetic anhydride (Sedova et al. *Zh. Org. Khim.* 1970, 6, (568).

Scheme III
Selected Methods of Fluorinated Aryl Sulfone Synthesis

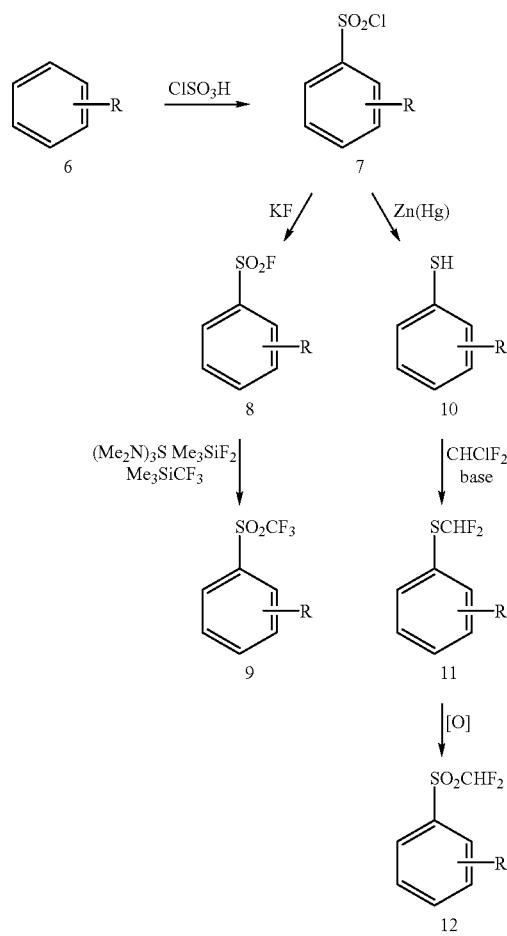

As shown in Scheme IV, non-symmetrical urea formation may involve reaction of an aryl isocyanate (14) with an aryl amine (13). The heteroaryl isocyanate may be synthesized from a heteroaryl amine by treatment with phosgene or a phosgene equivalent, such as trichloromethyl chloroformate (diphosgene), bis(trichloromethyl) carbonate (triphosgene), or N,N'-carbonyldiimidazole (CDI). The isocyanate may also be derived from a heterocyclic carboxylic acid derivative, such as an ester, an acid halide or an anhydride by a Curtius-type rearrangement. Thus, reaction of acid derivative 16 with an azide source, followed by rearrangement affords the isocyanate. The corresponding carboxylic acid (17) may also be subjected to Curtius-type rearrangements using diphenylphosphoryl azide (DPPA) or a similar reagent.

Scheme IV
Selected Methods of Non-Symmetrical Urea Formation

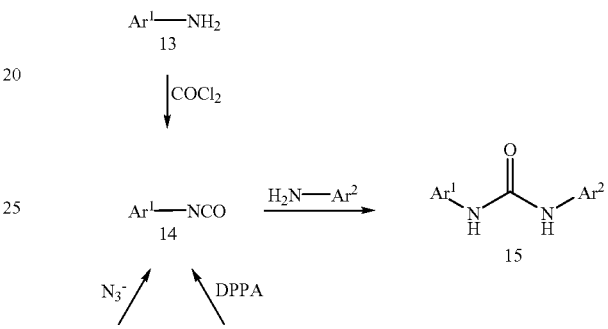

Finally, ureas may be further manipulated using methods familiar to those skilled in the art.

The invention also includes pharmaceutical compositions including a compound of Formula I, and a physiologically acceptable carrier.

The compounds may be administered orally, dermally, parenterally, by injection, by inhalation or spray, or sublingually, rectally or vaginally in dosage unit formulations. The term 'administration by injection' includes intravenous, intraarticular, intramuscular, subcutaneous and parenteral injections, as well as use of infusion techniques. Dermal administration may include topical application or transdermal administration. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets.

These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oil phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

Compounds of the invention may also be administered transdermally using methods known to those skilled in the art (see, for example: Chien; "Transdermal Controlled Systemic Medications"; Marcel Dekker, Inc.; 1987. Lipp et al. WO94/04157 3 Mar. 1994). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures one or more materials selected from lower alcohols, lower ketones, lower carboxylic acid esters, polar ethers, lower hydrocarbons, halogenated hydrocarbons.

Suitable penetration enhancing materials for transdermal delivery systems are known to those skilled in the art, and include, for example, monohydroxy or polyhydroxy alcohols such as ethanol, propylene glycol or benzyl alcohol, saturated or unsaturated $C_8$-$C_{18}$ fatty alcohols such as lauryl alcohol or cetyl alcohol, saturated or unsaturated $C_8$-$C_{18}$ fatty acids such as stearic acid, saturated or unsaturated fatty esters with up to 24 carbons such as methyl, ethyl, propyl, isopropyl, n-butyl, sec-butyl isobutyl tert-butyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures one or more materials selected from monohydroxy or polyhydroxy alcohols, saturated or unsaturated $C_8$-$C_{18}$ fatty alcohols, saturated or unsaturated $C_8$-$C_{18}$ fatty acids, saturated or unsaturated fatty esters with up to 24 carbons, diesters of saturated or unsaturated dicarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrene-butadiene copolymers, and natural and synthetic rubbers. Cellulose ethers, derivatized polyethylenes, and silicates may also be used as matrix components. Additional additives, such as viscous resins or oils may be added to increase the viscosity of the matrix.

For all regimens of use disclosed herein for compounds of Formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.1 to 200 mg administered between one to four times daily. The transdermal concentration will preferably be that required to maintain a daily dose of from 0.01 to 200 mg/Kg. The daily inhalation dosage regimen will preferably be from 0.01 to 10 mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, but not limited to the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e. the mode of treatment and the daily number of doses of a compound of Formula I or a pharmaceutically acceptable salt thereof given for a defined number of days, can be ascertained by those skilled in the art using conventional treatment tests.

The compounds of Formula I are producible from known compounds (or from starting materials which, in turn, are producible from known compounds), e.g., through the general preparative methods shown below. The activity of a given compound to inhibit raf kinase can be routinely assayed, e.g., according to procedures disclosed below. The following examples are for illustrative purposes only and are not intended, nor should they be construed to limit the invention in any way.

EXAMPLES

All reactions were performed in flame-dried or oven-dried glassware under a positive pressure of dry argon or dry nitrogen, and were stirred magnetically unless otherwise indicated. Sensitive liquids and solutions were transferred via syringe or cannula, and introduced into reaction vessels through rubber septa. Unless otherwise stated, the term 'concentration under reduced pressure' refers to use of a Buchi rotary evaporator at approximately 15 mmHg. Unless otherwise stated, the term 'under high vacuum' refers to a vacuum of 0.4-1.0 mmHg.

All temperatures are reported uncorrected in degrees Celsius (° C.). Unless otherwise indicated, all parts and percentages are by weight.

Commercial grade reagents and solvents were used without further purification. N-cyclohexyl-N'-(methylpolystyrene)carbodiimide was purchased from Calbiochem-Novabiochem Corp. 3-tert-Butylaniline, 5-tert-butyl-2-methoxyaniline, 4-bromo-3-(trifluoromethyl)aniline, 4-chloro-3-(trifluoromethyl)aniline 2-methoxy-5-(trifluoromethyl)aniline, 4-tert-butyl-2-nitroaniline, 5-(trifluoromethyl)-2-aminopyridine, 3-aminoquinioline, 3-aminoisoquinoline, 1-(4-methylpiperazinyl)-3-aminoisoquinoline, 3-amino-2-naphthol, ethyl 4-isocyanatobenzoate, N-acetyl-4-chloro-2-methoxy-5-(trifluoromethyl)aniline, 4-(4-nitrobenzyl)pyridine, 4-phenoxyaniline, 4-(4-chlorophenoxy) aniline and 4-chloro-3-(trifluoromethyl)phenyl isocyanate were purchased and used without further purification. Syntheses of 2-amino-4-tert-butylpyridine (C. K. Esser et al. WO 96/18616; C. J. Donahue et al. *Inorg. Chem.* 30, 1991, 1588), 3-amino-2-methoxyquinoline (E. Cho et al. WO 98/00402; A. Cordi et al. EP 542,609; *IBID Bioorg. Med. Chem.* 3, 1995, 129), 4-(3-carbamoylphenoxy)-1-nitrobenzene (K. Ikawa Yakugaku Zasshi 79, 1959, 760; Chem. Abstr. 53, 1959, 12761b), 3-tert-butylphenyl isocyanate (O. Rohr et al. DE 2,436,108) and 2-methoxy-5-(trifluoromethyl)phenyl isocyanate (K. Inukai et al. JP 42,025,067; *IBID Kogyo Kagaku Zasshi* 70, 1967, 491) have previously been described.

Thin-layer chromatography (TLC) was performed using Whatman® pre-coated glass-backed silica gel 60A F-254 250 µm plates. Visualization of plates was effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating, and/or (e) immersion of the plate in an acidic ethanol solution of 2,4-dinitrophenylhydrazine followed by heating. Column chromatography (flash chromatography) was performed using 230-400 mesh EM Science® silica gel.

Melting points (mp) were determined using a Thomas-Hoover melting point apparatus or a Mettler FP66 automated melting point apparatus and are uncorrected. Fourier transform infrared spectra were obtained using a Mattson 4020 Galaxy Series spectrophotometer. Proton ($^1$H) nuclear magnetic resonance (NMR) spectra were measured with a General Electric GN-Omega 300 (300 MHz) spectrometer with either Me$_4$Si (δ0.00) or residual protonated solvent (CHCl$_3$ δ 7.26; MeOH δ 3.30; DMSO δ 2.49) as standard. Carbon ($^{13}$C) NMR spectra were measured with a General Electric GN-Omega 300 (75 MHz) spectrometer with solvent (CDCl$_3$ δ 77.0; MeOD-d$_3$; δ 49.0; DMSO-d$_6$ δ 39.5) as standard. Low resolution mass spectra (MS) and high resolution mass spectra (HRMS) were either obtained as electron impact (EI) mass spectra or as fast atom bombardment (FAB) mass spectra. Electron impact mass spectra (EI-MS) were obtained with a Hewlett Packard 5989A mass spectrometer equipped with a Vacumetrics Desorption Chemical Ionization Probe for sample introduction. The ion source was maintained at 250° C. Electron impact ionization was performed with electron energy of 70 eV and a trap current of 300 µA. Liquid-cesium secondary ion mass spectra (FAB-MS), an updated version of fast atom bombardment were obtained using a Kratos Concept 1-H spectrometer. Chemical ionization mass spectra (CI-MS) were obtained using a Hewlett Packard MS-Engine (5989A) with methane or ammonia as the reagent gas (1×10$^{-4}$ torr to 2.5×10$^{-4}$ torr). The direct insertion desorption chemical ionization (DCI) probe (Vacuumetrics, Inc.) was ramped from 0-1.5 amps in 10 sec and held at 10 amps until all traces of the sample disappeared (~1-2 min). Spectra were scanned from 50-800 amu at 2 sec per scan. HPLC-electrospray mass spectra (HPLC ES-MS) were obtained using a Hewlett-Packard 1100 HPLC equipped with a quaternary pump, a variable wavelength detector, a C-18 column, and a Finnigan LCQ ion trap mass spectrometer with electrospray ionization. Spectra were scanned from 120-800 amu using a variable ion time according to the number of ions in the source. Gas chromatography-ion selective mass spectra (GC-MS) were obtained with a Hewlett Packard 5890 gas chromatograph equipped with an HP-1 methyl silicone column (0.33 mM coating; 25 m×0.2 mm) and a Hewlett Packard 5971 Mass Selective Detector (ionization energy 70 eV). Elemental analyses are conducted by Robertson Microlit Labs, Madison N.J.

All compounds displayed NMR spectra, LRMS and either elemental analysis or HRMS consistent with assigned structures.

LIST OF ABBREVIATIONS AND ACRONYMS

| | |
|---|---|
| AcOH | acetic acid |
| anh | anhydrous |
| atm | atmosphere(s) |
| BOC | tert-butoxycarbonyl |
| CDI | 1,1'-carbonyl diimidazole |
| conc | concentrated |
| dec | decomposition |
| DMAC | N,N-dimethylacetamide |
| DMPU | 1,3-dimethyl-3,4,5,6-tetrahydro-2(1H)-pyrimidinone |
| DMF | N,N-dimethylformamide |
| DMSO | dimethylsulfoxide |
| DPPA | diphenylphosphoryl azide |
| EDCI | 1-(3-dimethylaminopropyl)-3-ethylcarbodiimide |
| EtOAc | ethyl acetate |
| EtOH | ethanol (100%) |
| $Et_2O$ | diethyl ether |
| $Et_3N$ | triethylamine |
| HOBT | 1-hydroxybenzotriazole |
| m-CPBA | 3-chloroperoxybenzoic acid |
| MeOH | methanol |
| pet. ether | petroleum ether (boiling range 30-60° C.) |
| THF | tetrahydrofuran |
| TFA | trifluoroAcOH |
| Tf | trifluoromethanesulfonyl |

A. General Methods for Synthesis of Substituted Anilines

A1. General Method for Aryl Amine Formation via Ether Formation Followed by Ester Saponification, Curtius Rearrangement, and Carbamate Deprotection. Synthesis of 2-Amino-3-methoxynaphthalene

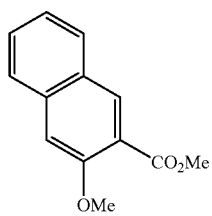

Step 1. Methyl 3-methoxy-2-naphthoate

A slurry of methyl 3-hydroxy-2-naphthoate (10.1 g, 50.1 mmol) and $K_2CO_3$ (7.96 g, 57.6 mmol) in DMF (200 mL) was stirred at room temp. for 15 min., then treated with iodomethane (3.43 mL, 55.1 mmol). The mixture was allowed to stir at room temp. overnight, then was treated with water (200 mL). The resulting mixture was extracted with EtOAc (2×200 mL). The combined organic layers were washed with a saturated NaCl solution (100 mL), dried ($MgSO_4$), concentrated under reduced pressure (approximately 0.4 mmHg overnight) to give methyl 3-methoxy-2-naphthoate as an amber oil (10.30 g): $^1$H-NMR (DMSO-$d_6$) δ2.70 (s, 3H), 2.85 (s, 3H), 7.38 (app t, J=8.09 Hz, 1H), 7.44 (s, 1H), 7.53 (app t, J=8.09 Hz, 1H), 7.84 (d, J=8.09 Hz, 1H), 7.90 (s, 1H), 8.21 (s, 1H).

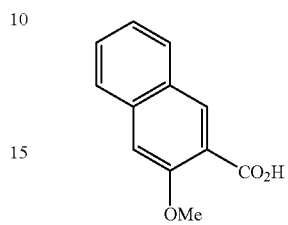

Step 2. 3-Methoxy-2-naphthoic acid

A solution of methyl 3-methoxy-2-naphthoate (6.28 g, 29.10 mmol) and water (10 mL) in MeOH (100 mL) at room temp. was treated with a 1N NaOH solution (33.4 mL, 33.4 mmol). The mixture was heated at the reflux temp. for 3 h, cooled to room temp., and made acidic with a 10% citric acid solution. The resulting solution was extracted with EtOAc (2×100 mL). The combined organic layers were washed with a saturated NaCl solution, dried ($MgSO_4$) and concentrated under reduced pressure. The residue was triturated with hexane then washed several times with hexane to give 3-methoxy-2-naphthoic acid as a white solid (5.40 g, 92%): $^1$H-NMR (DMSO-$d_6$) δ3.88 (s, 3H), 7.34-7.41 (m, 2H), 7.49-7.54 (m, 1H), 7.83 (d, J=8.09 Hz, 1H), 7.91 (d, J=8.09 Hz, 1H), 8.19 (s, 1H), 12.83 (br s, 1H).

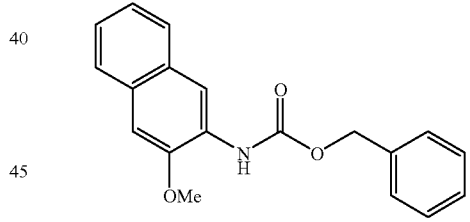

Step 3.
2-(N-(Carbobenzyloxy)amino-3-methoxynaphthalene

A solution of 3-methoxy-2-naphthoic acid (3.36 g, 16.6 mmol) and $Et_3N$ (2.59 mL, 18.6 mmol) in anh toluene (70 mL) was stirred at room temp. for 15 min., then treated with a solution of DPPA (5.12 g, 18.6 mmol) in toluene (10 mL) via pipette. The resulting mixture was heated at 80° C. for 2 h. After cooling the mixture to room temp., benzyl alcohol (2.06 mL, 20 mmol) was added via syringe. The mixture was then warmed to 80° C. overnight. The resulting mixture was cooled to room temp., quenched with a 10% citric acid solution, and extracted with EtOAc (2×100 mL). The combined organic layers were washed with a saturated NaCl solution, dried ($MgSO_4$) and concentrated under reduced pressure. The residue was purified by column chromatography (14% EtOAc/86% hexane) to give 2-(N-(carbobenzyloxy)amino-3-methoxynaphthalene as a pale yellow oil (5.1 g, 100%):

$^1$H-NMR (DMSO-$d_6$) δ3.89 (s, 3H), 5.17 (s, 2H), 7.27-7.44 (m, 8H), 7.72-7.75 (m, 2H), 8.20 (s, 1H), 8.76 (s, 1H).

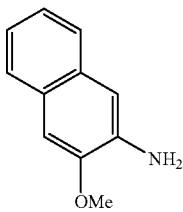

Step 4. 2-Amino-3-methoxynaphthalene

A slurry of 2-(N-(carbobenzyloxy)amino-3-methoxynaphthalene (5.0 g, 16.3 mmol) and 10% Pd/C (0.5 g) in EtOAc (70 mL) was maintained under a H$_2$ atm (balloon) at room temp. overnight. The resulting mixture was filtered through Celite® and concentrated under reduced pressure to give 2-amino-3-methoxynaphthalene as a pale pink powder (2.40 g, 85%): $^1$H-NMR (DMSO-$d_6$) δ3.86 (s, 3H), 6.86 (s, 2H), 7.04-7.16 (m, 2H), 7.43 (d, J=8.0 Hz, 1H), 7.56 (d, J=8.0 Hz, 1H); EI-MS m/z 173 (M$^+$).

A2. Synthesis of ω-Carbamyl Anilines via Formation of a Carbamylpyridine Followed by Nucleophilic Coupling with an Aryl Amine. Synthesis of 4-(2-N-Methylcarbamyl-4-pyridyloxy)aniline

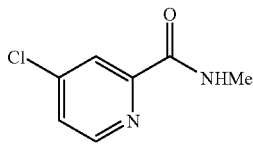

Step 1a. Synthesis of 4-chloro-N-methyl-2-pyridinecarboxamide via the Menisci reaction Caution: this is a highly hazardous, potentially explosive reaction. To a stirring solution of 4-chloropyridine (10.0 g) in N-methylformamide (250 mL) at room temp. was added conc. H$_2$SO$_4$ (3.55 mL) to generate an exotherm. To this mixture was added H$_2$O$_2$ (30% wt in H$_2$O, 17 mL) followed by FeSO$_4$·7H$_2$O (0.56 g) to generate another exotherm. The resulting mixture was stirred in the dark at room temp. for 1 h, then warmed slowly over 4 h to 45° C. When bubbling had subsided, the reaction was heated at 60° C. for 16 h. The resulting opaque brown solution was diluted with H$_2$O (700 mL) followed by a 10% NaOH solution (250 mL). The resulting mixture was extracted with EtOAc (3×500 mL). The organic phases were washed separately with a saturated NaCl solution (3×150 mL), then they were combined, dried (MgSO$_4$) and filtered through a pad of silica gel with the aid of EtOAc. The resulting brown oil was purified by column chromatography (gradient from 50% EtOAc/50% hexane to 80% EtOAc/20% hexane). The resulting yellow oil crystallized at 0° C. over 72 h to give 4-chloro-N-methyl-2-pyridinecarboxamide (0.61 g, 5.3%): TLC (50% EtOAc/50% hexane) R$_f$ 0.50; $^1$H NMR (CDCl$_3$) δ3.04 (d, J=5.1 Hz, 3H), 7.43 (dd, J=5.4, 2.4 Hz, 1H), 7.96 (br s, 1H), 8.21 (s, 1H), 8.44 (d, J=5.1 Hz, 1H); CI-MS m/z 171 ((M+H)$^+$).

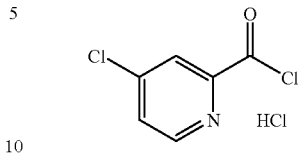

Step 1b. Synthesis of 4-chloropyridine-2-carbonyl chloride HCl salt via picolinic acid Anhydrous DMF (6.0 mL) was slowly added to SOCl$_2$ (180 mL) between 40° and 50° C. The solution was stirred in that temperature range for 10 min. then picolinic acid (60.0 g, 487 mmol) was added in portions over 30 min. The resulting solution was heated at 72° C. (vigorous SO$_2$ evolution) for 16 h to generate a yellow solid precipitate. The resulting mixture was cooled to room temp., diluted with toluene (500 mL) and concentrated to 200 mL. The toluene addition/concentration process was repeated twice. The resulting nearly dry residue was filtered and the solids were washed with toluene (2×200 mL) and dried under high vacuum for 4 h to afford 4-chloropyridine-2-carbonyl chloride HCl salt as a yellow-orange solid (92.0 g, 89%).

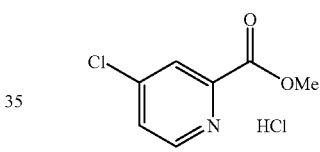

Step 2. Synthesis of methyl 4-chloropyridine-2-carboxylate HCl salt

Anh DMF (10.0 mL) was slowly added to SOCl$_2$ (300 mL) at 40-48° C. The solution was stirred at that temp. range for 10 min., then picolinic acid (100 g, 812 mmol) was added over 30 min. The resulting solution was heated at 72° C. (vigorous SO$_2$ evolution) for 16 h to generate a yellow solid. The resulting mixture was cooled to room temp., diluted with toluene (500 mL) and concentrated to 200 mL. The toluene addition/concentration process was repeated twice. The resulting nearly dry residue was filtered, and the solids were washed with toluene (50 mL) and dried under high vacuum for 4 hours to afford 4-chloropyridine-2-carbonyl chloride HCl salt as an off-white solid (27.2 g, 16%). This material was set aside.

The red filtrate was added to MeOH (200 mL) at a rate which kept the internal temperature below 55° C. The contents were stirred at room temp. for 45 min., cooled to 5° C. and treated with Et$_2$O (200 mL) dropwise. The resulting solids were filtered, washed with Et$_2$O (200 mL) and dried under reduced pressure at 35° C. to provide methyl 4-chloropyridine-2-carboxylate HCl salt as a white solid (110 g, 65%): mp 108-112° C.; $^1$H-NMR (DMSO-$d_6$) δ3.88 (s, 3H); 7.82 (dd, J=5.5, 2.2 Hz, 1H); 8.08 (d, J=2.2 Hz, 1H); 8.68 (d, J=5.5 Hz, 1H); 10.68 (br s, 1H); HPLC ES-MS m/z 172 ((M+H)$^+$).

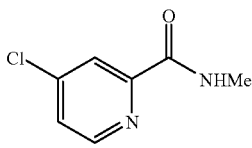

Step 3a. Synthesis of 4-chloro-N-methyl-2-pyridinecarboxamide from methyl 4-chloropyridine-2-carboxylate A suspension of methyl 4-chloropyridine-2-carboxylate HCl salt (89.0 g, 428 mmol) in MeOH (75 mL) at 0° C. was treated with a 2.0 M methylamine solution in THF (1 L) at a rate which kept the internal temp. below 5° C. The resulting mixture was stored at 3° C. for 5 h, then concentrated under reduced pressure. The resulting solids were suspended in EtOAc (1 L) and filtered. The filtrate was washed with a saturated NaCl solution (500 mL), dried ($Na_2SO_4$) and concentrated under reduced pressure to afford 4-chloro-N-methyl-2-pyridinecarboxamide as pale-yellow crystals (71.2 g, 97%): mp 41-43° C.; $^1$H-NMR (DMSO-$d_6$) δ2.81 (s, 3H), 7.74 (dd, J=5.1, 2.2 Hz, 1H), 8.00 (d, J=2.2, 1H), 8.61 (d, J=5.1 Hz, 1H), 8.85 (br d, 1H); Cl-MS m/z 171 ((M+H)$^+$).

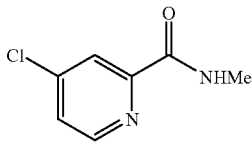

Step 3b. Synthesis of 4-chloro-N-methyl-2-pyridinecarboxamide from 4-chloropyridine-2-carbonyl chloride 4-Chloropyridine-2-carbonyl chloride HCl salt (7.0 g, 32.95 mmol) was added in portions to a mixture of a 2.0M methylamine solution in THF (100 mL) and MeOH (20 mL) at 0° C. The resulting mixture was stored at 3° C. for 4 h, then concentrated under reduced pressure. The resulting nearly dry solids were suspended in EtOAc (100 mL) and filtered. The filtrate was washed with a saturated NaCl solution (2×100 mL), dried ($Na_2SO_4$) and concentrated under reduced pressure to provide 4-chloro-N-methyl-2-pyridinecarboxamide as a yellow, crystalline solid (4.95 g, 88%): mp 37-40° C.

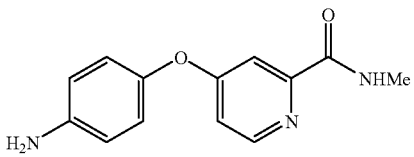

Step 4. Synthesis of 4-(2-(N-methylcarbamoyl)-4-pyridyloxy)aniline

A solution of 4-aminophenol (9.60 g, 88.0 mmol) in anh. DMF (150 mL) was treated with potassium tert-butoxide (10.29 g, 91.7 mmol), and the reddish-brown mixture was stirred at room temp. for 2 h. The contents were treated with 4-chloro-N-methyl-2-pyridinecarboxamide (15.0 g, 87.9 mmol) and $K_2CO_3$ (6.50 g, 47.0 mmol) and then heated at 80° C. for 8 h. The mixture was cooled to room temp. and separated between EtOAc (500 mL) and a saturated NaCl solution (500 mL). The aqueous phase was back-extracted with EtOAc (300 mL). The combined organic layers were washed with a saturated NaCl solution (4×1000 mL), dried ($Na_2SO_4$) and concentrated under reduced pressure. The resulting solids were dried under reduced pressure at 35° C. for 3 h to afford 4-(2-(N-methylcarbamoyl)-4-pyridyloxy)aniline as a light-brown solid 17.9 g, 84%): $^1$H-NMR (DMSO-$d_6$) δ2.77 (d, J=4.8 Hz, 3H), 5.17 (br s, 2H), 6.64, 6.86 (AA'BB' quartet, J=8.4 Hz, 4H), 7.06 (dd, J=5.5, 2.5 Hz, 1H), 7.33 (d, J=2.5 Hz, 1H), 8.44 (d, J=5.5 Hz, 1H), 8.73 (br d, 1H); HPLC ES-MS m/z 244 ((M+H)$^+$).

A3. General Method for the Synthesis of Anilines by Nucleophilic Aromatic Addition Followed by Nitroarene Reduction. Synthesis of 5-(4-Aminophenoxy)isoindoline-1,3-dione

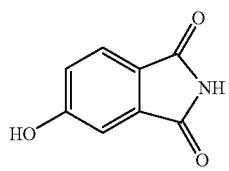

Step 1. Synthesis of 5-hydroxyisoindoline-1,3-dione

To a mixture of ammonium carbonate (5.28 g, 54.9 mmol) in conc. AcOH (25 mL) was slowly added 4-hydroxyphthalic acid (5.0 g, 27.45 mmol). The resulting mixture was heated at 120° C. for 45 min., then the clear, bright yellow mixture was heated at 160° C. for 2 h. The resulting mixture was maintained at 160° C. and was concentrated to approximately 15 mL, then was cooled to room temp. and adjusted pH 10 with a 1N NaOH solution. This mixture was cooled to 0° C. and slowly acidified to pH 5 using a 1N HCl solution. The resultant precipitate was collected by filtration and dried under reduced pressure to yield 5-hydroxyisoindoline-1,3-dione as a pale yellow powder as product (3.24 g, 72%): $^1$H NMR (DMSO-$d_6$) δ7.00-7.03 (m, 2H), 7.56 (d, J=9.3 Hz, 1H).

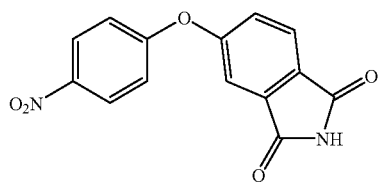

Step 2. Synthesis of 5-(4-nitrophenoxy)isoindoline-1,3-dione

To a stirring slurry of NaH (1.1 g, 44.9 mmol) in DMF (40 mL) at 0° C. was added a solution of 5-hydroxyisoindoline-1,3-dione (3.2 g, 19.6 mmol) in DMF (40 mL) dropwise. The bright yellow-green mixture was allowed to return to room temp. and was stirred for 1 h, then 1-fluoro-4-nitrobenzene (2.67 g, 18.7 mmol) was added via syringe in 3-4 portions. The resulting mixture was heated at 70° C. overnight, then cooled to room temp. and diluted slowly with water (150 mL), and extracted with EtOAc (2×100 mL). The combined organic layers were dried (MgSO$_4$) and concentrated under reduced pressure to give 5-(4-nitrophenoxy)isoindoline-1,3-dione as a yellow solid (3.3 g, 62%): TLC (30% EtOAc/70% hexane) R$_f$ 0.28; $^1$H NMR (DMSO-d$_6$) δ7.32 (d, J=12 Hz, 2H), 7.52-7.57 (m, 2H), 7.89 (d, J=7.8 Hz, 1H), 8.29 (d, J=9 Hz, 2H), 11.43 (br s, 1H); CI-MS m/z 285 ((M+H)$^+$, 100%).

sequentially washed with a 1N HCl solution (15 mL), a 1N NaOH solution (15 mL) and a saturated NaCl solution (15 mL), dried (MgSO$_4$) and concentrated under reduced pressure. The resulting orange-brown solids were purified via column chromatography (60 g SiO$_2$; gradient from 6% EtOAc/94% hexane to 25% EtOAc/75% hexane) to give 1-(4-tert-butyl-2-nitrophenyl)-2,5-dimethylpyrrole as an orange-yellow solid (0.34 g, 49%): TLC (15% EtOAc/85% hexane) R$_f$ 0.67; $^1$H NMR (CDCl$_3$) d 1.34 (s, 9H), 1.89 (s, 6H), 5.84 (s, 2H), 7.19-7.24 (m, 1H), 7.62 (dd, 1H), 7.88 (d, J=2.4 Hz, 1H); CI-MS m/z 273 ((M+H)$^+$, 50%).

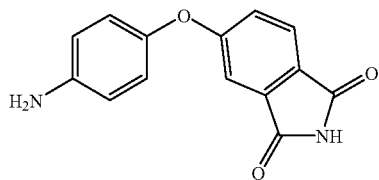

Step 3. Synthesis of
5-(4-aminophenoxy)isoindoline-1,3-dione

A solution of 5-(4-nitrophenoxy)isoindoline-1,3-dione (0.6 g, 2.11 mmol) in conc. AcOH (12 mL) and water (0.1 mL) was stirred under stream of argon while iron powder (0.59 g, 55.9 mmol) was added slowly. This mixture stirred at room temp. for 72 h, then was diluted with water (25 mL) and extracted with EtOAc (3×50 mL). The combined organic layers were dried (MgSO$_4$) and concentrated under reduced pressure to give 5-(4-aminophenoxy)isoindoline-1,3-dione as a brownish solid (0.4 g, 75%): TLC (50% EtOAc/50% hexane) R$_f$ 0.27; $^1$H NMR (DMSO-d$_6$) δ5.14 (br s, 2H), 6.62 (d, J=8.7 Hz, 2H), 6.84 (d, J=8.7 Hz, 2H), 7.03 (d, J=2.1 Hz, 1H), 7.23 (dd, 1H), 7.75 (d, J=8.4 Hz, 1H), 11.02 (s, 1H); HPLC ES-MS m/z 255 ((M+H)+, 100%).

A4. General Method for the Synthesis of
Pyrrolylanilines. Synthesis of
5-tert-Butyl-2-(2,5-dimethylpyrrolyl)aniline

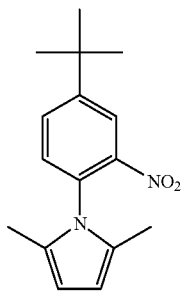

Step 1. Synthesis of
1-(4-tert-butyl-2-nitrophenyl)-2,5-dimethylpyrrole

To a stirring solution of 2-nitro-4-tert-butylaniline (0.5 g, 2.57 mmol) in cyclohexane (10 mL) was added AcOH (0.1 mL) and acetonylacetone (0.299 g, 2.63 mmol) via syringe. The reaction mixture was heated at 120° C. for 72 h with azeotropic removal of volatiles. The reaction mixture was cooled to room temp., diluted with CH$_2$Cl$_2$ (10 mL) and

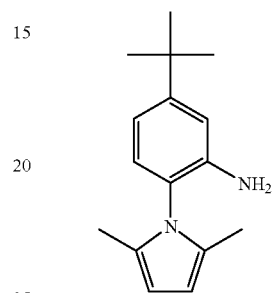

Step 2. Synthesis of
5-tert--Butyl-2-(2,5-dimethylpyrrolyl)aniline

A slurry of 1-(4-tert-butyl-2-nitrophenyl)-2,5-dimethylpyrrole (0.341 g, 1.25 mmol), 10% Pd/C (0.056 g) and EtOAc (50 mL) under an H$_2$ atmosphere (balloon) was stirred for 72 h, then filtered through a pad of Celite®. The filtrate was concentrated under reduced pressure to give 5-tert--butyl-2-(2,5-dimethylpyrrolyl)aniline as yellowish solids (0.30 g, 99%): TLC (10% EtOAc/90% hexane) R$_f$ 0.43; $^1$H NMR (CDCl$_3$) δ1.28 (s, 9H), 1.87-1.91 (m, 8H), 5.85 (br s, 2H), 6.73-6.96 (m, 3H), 7.28 (br s, 1H).

A5. General Method for the Synthesis of Anilines
from Anilines by Nucleophilic Aromatic Substitution. Synthesis of 4-(2-(N-Methylcarbamoyl)-4-pyridyloxy)-2-methylaniline HCl Salt

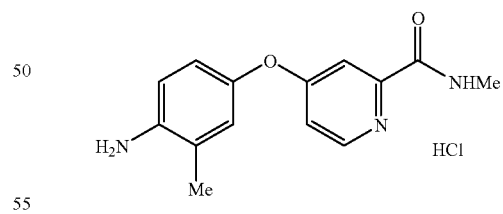

A solution of 4-amino-3-methylphenol (5.45 g, 44.25 mmol) in dry dimethylacetamide (75 mL) was treated with potassium tert-butoxide (10.86 g, 96.77 mmol) and the black mixture was stirred at room temp. until the flask had reached room temp. The contents were then treated with 4-chloro-N-methyl-2-pyridinecarboxamide (Method A2, Step 3b; 7.52 g, 44.2 mmol) and heated at 110° C. for 8 h. The mixture was cooled to room temp. and diluted with water (75 mL). The organic layer was extracted with EtOAc (5×100 mL). The combined organic layers were washed with a saturated NaCl solution (200 mL), dried (MgSO$_4$) and concentrated under reduced pressure. The residual black oil was treated with Et₂O (50 mL) and sonicated. The solution was then treated with HCl (1M in Et₂O; 100 mL) and stirred at room temp. for 5 min. The resulting dark pink solid (7.04 g, 24.1 mmol) was removed by filtration from solution and stored under anaerobic conditions at 0° C. prior to use: $^1$H NMR (DMSO-d$_6$) δ2.41 (s, 3H), 2.78 (d, J=4.4 Hz, 3H), 4.93 (br s, 2H), 7.19 (dd, J=8.5, 2.6 Hz, 1H), 7.23 (dd, J=5.5, 2.6 Hz, 1H), 7.26 (d, J=2.6 Hz, 1H), 7.55 (d, J=2.6 Hz, 1H), 7.64 (d, J=8.8 Hz, 1H), 8.55 (d, J=5.9 Hz, 1H), 8.99 (q, J=4.8 Hz, 1H).

A6. General Method for the Synthesis of Anilines from Hydroxyanilines by N-Protection, Nucleophilic Aromatic Substitution and Deprotection. Synthesis of 4-(2-(N-Methylcarbamoyl)-4-pyridyloxy)-2-chloroaniline

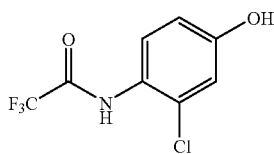

Step 1: Synthesis of 3-Chloro-4-(2,2,2-trifluoroacetylamino)phenol

Iron (3.24 g, 58.00 mmol) was added to stirring TFA (200 mL). To this slurry was added 2-chloro-4-nitrophenol (10.0 g, 58.0 mmol) and trifluoroacetic anhydride (20 mL). This gray slurry was stirred at room temp. for 6 d. The iron was filtered from solution and the remaining material was concentrated under reduced pressure. The resulting gray solid was dissolved in water (20 mL). To the resulting yellow solution was added a saturated NaHCO₃ solution (50 mL). The solid which precipitated from solution and was removed. The filtrate was slowly quenched with the sodium bicarbonate solution until the product visibly separated from solution (determined was using a mini work-up vial). The slightly cloudy yellow solution was extracted with EtOAc (3×125 mL). The combined organic layers were washed with a saturated NaCl solution (125 mL), dried (MgSO₄) and concentrated under reduced pressure. The $^1$H NMR (DMSO-d$_6$) indicated a 1:1 ratio of the nitrophenol starting material and the intended product 3-chloro-4-(2,2,2-trifluoroacetylamino)phenol. The crude material was taken on to the next step without further purification.

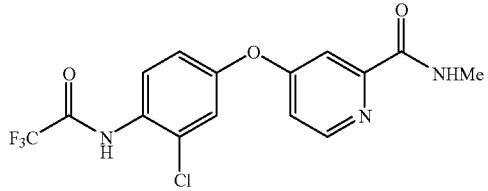

Step 2: Synthesis of 4-(2-(N-Methylcarbamoyl)-4-pyridyloxy)-2-chlorophenyl (222-trifluoroacetamide A solution of crude 3-chloro-4-(2,2,2-trifluoroacetylamino)phenol (5.62 g, 23.46 mmol) in dry dimethylacetamide (50 mL) was treated with potassium tert-butoxide (5.16 g, 45.98 mmol) and the brownish black mixture was stirred at room temp. until the flask had cooled to room temp. The resulting mixture was treated with 4-chloro-N-methyl-2-pyridinecarboxamide (Method A2, Step 3b; 1.99 g, 11.7 mmol) and heated at 100° C. under argon for 4 d. The black reaction mixture was cooled to room temp. and then poured into cold water (100 mL). The mixture was extracted with EtOAc (3×75 mL) and the combined organic layers were concentrated under reduced pressure. The residual brown oil was purified by column chromatography (gradient from 20% EtOAc/pet. ether to 40% EtOAc/pet. ether) to yield 4-(2-(N-Methylcarbamoyl)-4-pyridyloxy)-2-chlorophenyl (222-trifluoroacetamide as a yellow solid (8.59 g, 23.0 mmol).

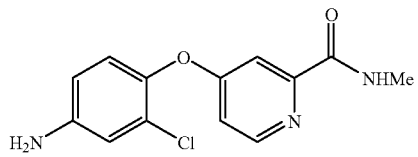

Step 3. Synthesis of 4-(2-(N-Methylcarbamoyl)-4-pyridyloxy)-2-chloroaniline

A solution of crude 4-(2-(N-Methylcarbamoyl)-4-pyridyloxy)-2-chlorophenyl (222-trifluoroacetamide (8.59 g, 23.0 mmol) in dry 4-dioxane (20 mL) was treated with a 1N NaOH solution (20 mL). This brown solution was allowed to stir for 8 h. To this solution was added EtOAc (40 mL). The green organic layer was extracted with EtOAc (3×40 mL) and the solvent was concentrated to yield 4-(2-(N-Methylcarbamoyl)-4-pyridyloxy)-2-chloroaniline as a green oil that solidified upon standing (2.86 g, 10.30 mmol): $^1$H NMR (DMSO-d$_6$) δ2.77 (d, J=4.8 Hz, 3H), 5.51 (s, 2H), 6.60 (dd, J=8.5, 2.6 Hz, 1H), 6.76 (d, J=2.6 Hz, 1H), 7.03 (d, J=8.5 Hz, 1H), 7.07 (dd, J=5.5, 2.6, Hz, 1H), 7.27 (d, J=2.6 Hz, 1H), 8.46 (d, J=5.5 Hz, 1H), 8.75 (q, J=4.8, 1H).

A7. General Method for the Deprotection of an Acylated Aniline. Synthesis of 4-Chloro-2-methoxy-5-(trifluoromethyl)aniline

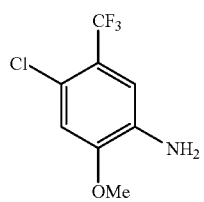

A suspension of 3-chloro-6-(N-acetyl)-4-(trifluoromethyl)anisole (4.00 g, 14.95 mmol) in a 6M HCl solution (24 mL) was heated at the reflux temp. for 1 h. The resulting solution was allowed to cool to room temp. during which time it solidified slightly. The resulting mixture was diluted with water (20 mL) then treated with a combination of solid NaOH and a saturated NaHCO₃ solution until the solution was basic. The organic layer was extracted with CH₂Cl₂ (3×50 mL). The combined organics were dried (MgSO₄) and concentrated under reduced pressure to yield 4-chloro-2-methoxy-5-(trifluoromethyl)aniline as a brown oil (3.20 g, 14.2 mmol): 1H NMR (DMSO-d$_6$) δ3.84 (s, 3H), 5.30 (s, 2H), 7.01 (s, 2H).

A8. General Method for Synthesis of ω-Alkoxy-ω-carboxyphenyl Anilines. Synthesis of 4-(3-(N-Methylcarbamoyl)-4-methoxyphenoxy)aniline

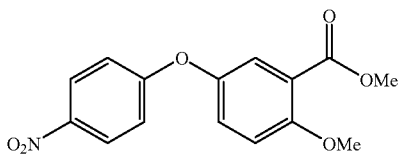

Step 1. 4-(3-Methoxycarbonyl-4-methoxyphenoxy)-1-nitrobenzene

To a solution of 4-(3-carboxy-4-hydroxyphenoxy)-1-nitrobenzene (prepared from 2,5-dihydroxybenzoic acid in a manner analogous to that described in Method 13, Step 1, 12 mmol) in acetone (50 mL) was added K$_2$CO$_3$ (5 g) and dimethyl sulfate (3.5 mL). The resulting mixture was heated at the reflux temp. overnight, then cooled to room temp. and filtered through a pad of Celite®. The resulting solution was concentrated under reduced pressure, absorbed onto SiO$_2$, and purified by column chromatography (50% EtOAc/50% hexane) to give 4-(3-methoxycarbonyl-4-methoxyphenoxy)-1-nitrobenzene as a yellow powder (3 g): mp 115-118° C.

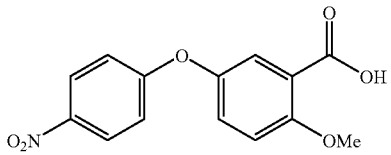

Step 2.
4-(3-Carboxy-4-methoxyphenoxy)-1-nitrobenzene

A mixture of 4-(3-methoxycarbonyl-4-methoxyphenoxy)-1-nitrobenzene (1.2 g), KOH (0.33 g) and water (5 mL) in MeOH (45 mL) was stirred at room temp. overnight and then heated at the reflux temp. for 4 h. The resulting mixture was cooled to room temp. and concentrated under reduced pressure. The residue was dissolved in water (50 mL), and the aqueous mixture was made acidic with a 1N HCl solution. The resulting mixture was extracted with EtOAc (50 mL). The organic layer was dried (MgSO$_4$) and concentrated under reduced pressure to give 4-(3-carboxy-4-methoxyphenoxy)-1-nitrobenzene (1.04 g).

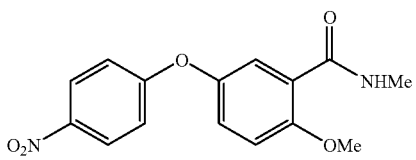

Step 3. 4-(3-(N-Methylcarbamoyl)-4-methoxyphenoxy)-1-nitrobenzene

To a solution of 4-(3-carboxy-4-methoxyphenoxy)-1-nitrobenzene (0.50 g, 1.75 mmol) in CH$_2$Cl$_2$ (12 mL) was added SOCl$_2$ (0.64 mL, 8.77 mmol) in portions. The resulting solution was heated at the reflux temp. for 18 h, cooled to room temp., and concentrated under reduced pressure. The resulting yellow solids were dissolved in CH$_2$Cl$_2$ (3 mL) then the resulting solution was treated with a methylamine solution (2.0 M in THF, 3.5 mL, 7.02 mmol) in portions (CAUTION: gas evolution), and stirred at room temp. for 4 h. The resulting mixture was treated with a 1N NaOH solution, then extracted with CH$_2$Cl$_2$ (25 mL). The organic layer was dried (Na$_2$SO$_4$) and concentrated under reduced pressure to give 4-(3-(N-methylcarbamoyl)-4-methoxyphenoxy)-1-nitrobenzene as a yellow solid (0.50 g, 95%).

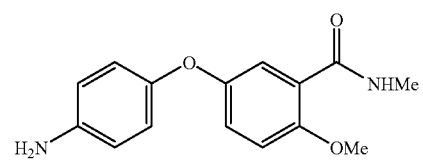

Step 4.
4-(3-(N-Methylcarbamoyl)-4-methoxyphenoxy)aniline

A slurry of 4-(3-(N-methylcarbamoly)-4-methoxyphenoxy)-1-nitrobenzene (0.78 g, 2.60 mmol) and 10% Pd/C (0.20 g) in EtOH (55 mL) was stirred under 1 atm of H$_2$ (balloon) for 2.5 d, then was filtered through a pad of Celite®. The resulting solution was concentrated under reduced pressure to afford 4-(3-(N-methylcarbamoly)-4-methoxyphenoxy)aniline as an off-white solid (0.68 g, 96%): TLC (0.1% Et$_3$N/99.9% EtOAc) R$_f$ 0.36.

A9. General Method for Preparation of ω-Alkylphthalimide-containing Anilines. Synthesis of 5-(4-Aminophenoxy)-2-methylisoindoline-1,3-dione

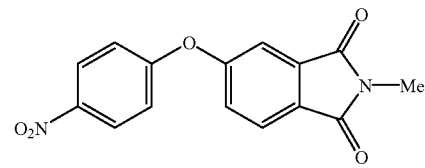

Step 1. Synthesis of 5-(4-Nitrophenoxy)-2-methylisoindoline-1,3-dione

A slurry of 5-(4-nitrophenoxy)isoindoline-1,3-dione (A3 Step 2; 1.0 g, 3.52 mmol) and NaH (0.13 g, 5.27 mmol) in DMF (15 mL) was stirred at room temp. for 1 h, then treated with methyl iodide (0.3 mL, 4.57 mmol). The resulting mixture was stirred at room temp. overnight, then was cooled to ° C. and treated with water (10 mL). The resulting solids were collected and dried under reduced pressure to give 5-(4-nitrophenoxy)-2-methylisoindoline-1,3-dione as a bright yellow solid (0.87 g, 83%): TLC (35% EtOAc/65% hexane) $R_f$ 0.61.

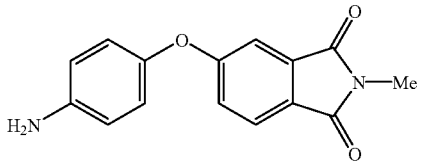

Step 2. Synthesis of 5-(4-Aminophenoxy)-2-methylisoindoline-1,3-dione

A slurry of nitrophenoxy)-2-methylisoindoline-1,3-dione (0.87 g, 2.78 mmol) and 10% Pd/C (0.10 g) in MeOH was stirred under 1 atm of $H_2$ (balloon) overnight. The resulting mixture was filtered through a pad of Celite® and concentrated under reduced pressure. The resulting yellow solids were dissolved in EtOAc (3 mL) and filtered through a plug of $SiO_2$ (60% EtOAc/40% hexane) to afford 5-(4-aminophenoxy)-2-methylisoindoline-1,3-dione as a yellow solid (0.67 g, 86%): TLC (40% EtOAc/60% hexane) $R_f$ 0.27.

A10. General Method for Synthesis of ω-Carbamoylaryl Anilines Through Reaction of ω-Alkoxycarbonylaryl Precursors with Amines. Synthesis of 4-(2-(N-(2-morpholin-4-ylethyl)carbamoyl)pyridyloxy)aniline

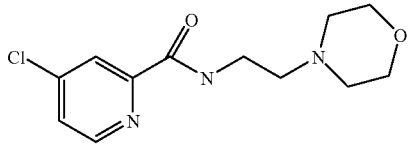

Step 1. Synthesis of 4-Chloro-2-(N-(2-morpholin-4-ylethyl)carbamoyl)pyridine

To a solution of methyl 4-chloropyridine-2-carboxylate HCl salt (Method A2, Step 2; 1.01 g, 4.86 mmol) in THF (20 mL) was added 4-(2-aminoethyl)morpholine (2.55 mL, 19.4 mmol) dropwise and the resulting solution was heated at the reflux temp. for 20 h, cooled to room temp., and treated with water (50 mL). The resulting mixture was extracted with EtOAc (50 mL). The organic layer was dried ($MgSO_4$) and concentrated under reduced pressure to afford 4-chloro-2-(N-(2-morpholin-4-ylethyl)carbamoyl)pyridine as a yellow oil (1.25 g, 95%): TLC (10% MeOH/90% EtOAc) $R_f$ 0.50.

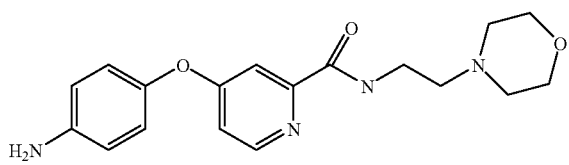

Step 2. Synthesis of 4-(2-(N-(2-Morpholin-4-ylethyl)carbamoyl)pyridyloxy)aniline A solution of 4-aminophenol (0.49 g, 4.52 mmol) and potassium tert-butoxide (0.53 g, 4.75 mol) in DMF (8 mL) was stirred at room temp. for 2 h, then was sequentially treated with 4-chloro-2-(N-(2-morpholin-4-ylethyl)carbamoyl)pyridine (1.22 g, 4.52 mmol) and $K_2CO_3$ (0.31 g, 2.26 mmol). The resulting mixture was heated at 75° C. overnight, cooled to room temp., and separated between EtOAc (25 mL) and a saturated NaCl solution (25 mL). The aqueous layer was back extracted with EtOAc (25 mL). The combined organic layers were washed with a saturated NaCl solution (3×25 mL) and concentrated under reduced pressure. The resulting brown solids were purified by column chromatography (58 g; gradient from 100% EtOAc to 25% MeOH/75% EtOAc) to afford 4-(2-(N-(2-morpholin-4-ylethyl)carbamoyl)pyridyloxy)aniline (1.0 g, 65%): TLC (10% MeOH/90% EtOAc) $R_f$ 0.32.

A11. General Method for the Reduction of Nitroarenes to Arylamines. Synthesis of 4-(3-Carboxyphenoxy)aniline

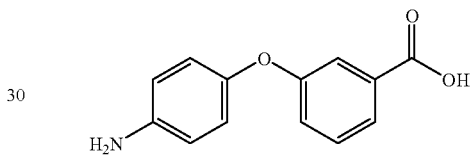

A slurry of 4-(3-carboxyphenoxy)-1-nitrobenzene (5.38 g, 20.7 mmol) and 10% Pd/C (0.50 g) in MeOH (120 mL) was stirred under an $H_2$ atmosphere (balloon) for 2 d. The resulting mixture was filtered through a pad of Celite®, then concentrated under reduced pressure to afford 4-(3-carboxyphenoxy)aniline as a brown solid (2.26 g, 48%): TLC (10% MeOH/90% $CH_2Cl_2$) $R_f$ 0.44 (streaking).

A12. General Method for the Synthesis of Isoindolinone-Containing Anilines. Synthesis of 4-(1-Oxoisoindolin-5-yloxy)aniline

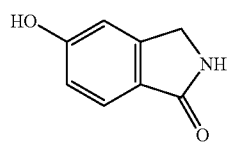

Step 1. Synthesis of 5-hydroxyisoindolin-1-one

To a solution of 5-hydroxyphthalimide (19.8 g, 121 mmol) in AcOH (500 mL) was slowly added zinc dust (47.6 g, 729 mmol) in portions, then the mixture was heated at the reflux temp. for 40 min., filtered hot, and concentrated under reduced pressure. The reaction was repeated on the same scale and the combined oily residue was purified by column chromatography (1.1 Kg $SiO_2$; gradient from 60% EtOAc/40% hexane to 25% MeOH/75% EtOAc) to give 5-hydroxyisoindolin-1-one (3.77 g): TLC (100% EtOAc) $R_f$ 0.17; HPLC ES-MS m/z 150 ((M+H)$^+$).

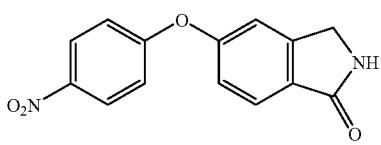

Step 2. Synthesis of 4-(1-isoindolinon-5-yloxy)-1-nitrobenzene

To a slurry of NaH (0.39 g, 16.1 mmol) in DMF at 0° C. was added 5-hydroxyisoindolin-1-one (2.0 g, 13.4 mmol) in portions. The resulting slurry was allowed to warm to room temp. and was stirred for 45 min., then 4-fluoro-1-nitrobenzene was added and then mixture was heated at 70° C. for 3 h. The mixture was cooled to 0° C. and treated with water dropwise until a precipitate formed. The resulting solids were collected to give 4-(1-isoindolinon-5-yloxy)-1-nitrobenzene as a dark yellow solid (3.23 g, 89%): TLC (100% EtOAc) $R_f$ 0.35.

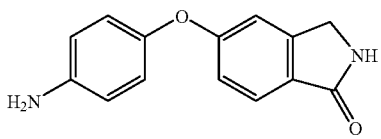

Step 3. Synthesis of 4-(1-oxoisoindolin-5-yloxy)aniline

A slurry of 4-(1-isoindolinon-5-yloxy)-1-nitrobenzene (2.12 g, 7.8 mmol) and 10% Pd/C (0.20 g) in EtOH (50 mL) was stirred under an $H_2$ atmosphere (balloon) for 4 h, then filtered through a pad of Celite®. The filtrate was concentrated under reduced pressure to afford 4-(1-oxoisoindolin-5-yloxy)aniline as a dark yellow solid: TLC (100% EtOAc) $R_f$ 0.15.

A13. General Method for the Synthesis of ω-Carbamoyl Anilines via EDCI-Mediated Amide Formation Followed by Nitroarene Reduction. Synthesis of 4-(3-N-Methylcarbamoylphenoxy)aniline

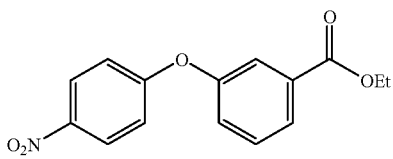

Step 1. Synthesis of 4-(3-ethoxycarbonylphenoxy)-1-nitrobenzene

A mixture of 4-fluoro-1-nitrobenzene (16 mL, 150 mmol), ethyl 3-hydroxybenzoate 25 g, 150 mmol) and $K_2CO_3$ (41 g, 300 mmol) in DMF (125 mL) was heated at the reflux temp. overnight, cooled to room temp. and treated with water (250 mL). The resulting mixture was extracted with EtOAc (3×150 mL). The combined organic phases were sequentially washed with water (3×100 mL) and a saturated NaCl solution (2×100 mL), dried ($Na_2SO_4$) and concentrated under reduced pressure. The residue was purified by column chromatography (10% EtOAc/90% hexane) to afford 4-(3-ethoxycarbonylphenoxy)-1-nitrobenzene as an oil (38 g).

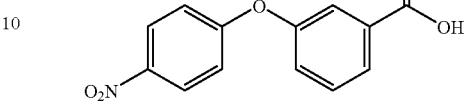

Step 2. Synthesis of 4-(3-carboxyphenoxy)-1-nitrobenzene

To a vigorously stirred mixture of 4-(3-ethoxycarbonylphenoxy)-1-nitrobenzene (5.14 g, 17.9 mmol) in a 3:1 THF/water solution (75 mL) was added a solution LiOH.$H_2O$ (1.50 g, 35.8 mmol) in water (36 mL). The resulting mixture was heated at 50° C. overnight, then cooled to room temp., concentrated under reduced pressure, and adjusted to pH 2 with a 1M HCl solution. The resulting bright yellow solids were removed by filtration and washed with hexane to give 4-(3-carboxyphenoxy)-1-nitrobenzene (4.40 g, 95%).

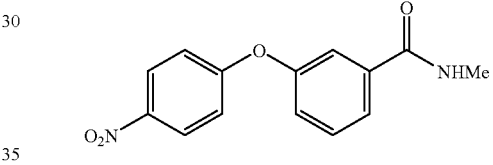

Step 3. Synthesis of 4-(3-(N-methylcarbamoyl)phenoxy)-1-nitrobenzene

A mixture of 4-(3-carboxyphenoxy)-1-nitrobenzene (3.72 g, 14.4 mmol), EDCI.HCl (3.63 g, 18.6 mmol), N-methylmorpholine (1.6 mL, 14.5 mmol) and methylamine (2.0M in THF; 8 mL, 16 mmol) in $CH_2Cl_2$ (45 mL) was stirred at room temp. for 3 d, then concentrated under reduced pressure. The residue was dissolved in EtOAc (50 mL) and the resulting mixture was extracted with a 1M HCl solution (50 mL). The aqueous layer was back-extracted with EtOAc (2×50 mL). The combined organic phases were washed with a saturated NaCl solution (50 mL), dried ($Na_2SO_4$), and concentrated under reduced pressure to give 4-(3-(N-methylcarbamoyl)phenoxy)-1-nitrobenzene as an oil (1.89 g).

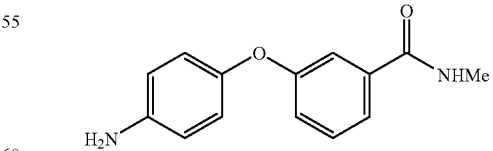

Step 4. Synthesis of 4-(3-(N-methylcarbamoyl)phenoxy)aniline

A slurry of 4-(3-(N-methylcarbamoyl)phenoxy)-1-nitrobenzene (1.89 g, 6.95 mmol) and 5% Pd/C (0.24 g) in EtOAc (20 mL) was stirred under an $H_2$ atm (balloon) overnight. The resulting mixture was filtered through a pad of Celite® and concentrated under reduced pressure. The residue was purified by column chromatography (5% MeOH/ 95% $CH_2Cl_2$). The resulting oil solidified under vacuum overnight to give 4-(3-(N-methylcarbamoyl)phenoxy)aniline as a yellow solid (0.95 g, 56%).

A14. General Method for the Synthesis of ω-Carbamoyl Anilines via EDCI-Mediated Amide Formation Followed by Nitroarene Reduction. Synthesis of 4-3-(5-Methylcarbamoyl)pyridyloxy)aniline

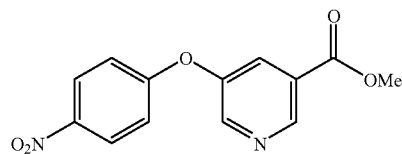

Step 1. Synthesis of 4-(3-(5-methoxycarbonyl)pyridyloxy)-1-nitrobenzene

To a slurry of NaH (0.63 g, 26.1 mmol) in DMF (20 mL) was added a solution of methyl 5-hydroxynicotinate (2.0 g, 13.1 mmol) in DMF (10 mL). The resulting mixture was added to a solution of 4-fluoronitrobenzene (1.4 mL, 13.1 mmol) in DMF (10 mL) and the resulting mixture was heated at 70° C. overnight, cooled to room temp., and treated with MeOH (5 mL) followed by water (50 mL). The resulting mixture was extracted with EtOAc (100 mL). The organic phase was concentrated under reduced pressure. The residue was purified by column chromatography (30% EtOAc/70% hexane) to afford 4-(3-(5-methoxycarbonyl)pyridyloxy)-1-nitrobenzene (0.60 g).

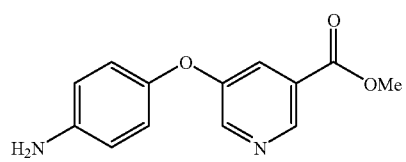

Step 2. Synthesis of 4-(3-(5-methoxycarbonyl)pyridyloxy)aniline

A slurry of 4-(3-(5-methoxycarbonyl)pyridyloxy)-1-nitrobenzene (0.60 g, 2.20 mmol) and 10% Pd/C in MeOH/ EtOAc was stirred under an $H_2$ atmosphere (balloon) for 72 h. The resulting mixture was filtered and the filtrate was concentrated under reduced pressure. The residue was purified by column chromatography (gradient from 10% EtOAc/90% hexane to 30% EtOAc/70% hexane to 50% EtOAc/50% hexane) to afford 4-(3-(5-methoxycarbonyl)pyridyloxy)aniline (0.28 g, 60%): $^1$H NMR (CDCl$_3$) δ3.92 (s, 3H), 6.71 (d, 2H), 6.89 (d, 2H), 7.73 (, 1H), 8.51 (d, 1H), 8.87 (d, 1H).

A15. Synthesis of an Aniline via Electrophilic Nitration Followed by Reduction. Synthesis of 4-(3-Methylsulfamoylphenoxy)aniline

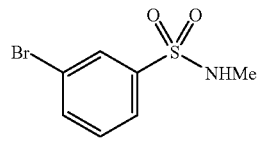

Step 1. Synthesis of N-methyl-3-bromobenzenesulfonamide

To a solution of 3-bromobenzenesulfonyl chloride (2.5 g, 11.2 mmol) in THF (15 mL) at 0° C. was added methylamine (2.0M in THF; 28 mL, 56 mmol). The resulting solution was allowed to warm to room temp. and was stirred at room temp. overnight. The resulting mixture was separated between EtOAc (25 mL) and a 1M HCl solution (25 mL). The aqueous phase was back-extracted with EtOAc (2×25 mL). The combined organic phases were sequentially washed with water (2×25 mL) and a saturated NaCl solution (25 mL), dried (MgSO$_4$) and concentrated under reduced pressure to give N-methyl-3-bromobenzenesulfonamide as a white solid (2.8 g, 99%).

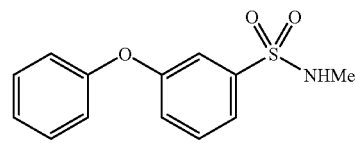

Step 2. Synthesis of 4-(3-(N-methylsulfamoyl)phenyloxy)benzene

To a slurry of phenol (1.9 g, 20 mmol), K$_2$CO$_3$ (6.0 g, 40 mmol), and CuI (4 g, 20 mmol) in DMF (25 mL) was added N-methyl-3-bromobenzenesulfonamide (2.5 g, 10 mmol), and the resulting mixture was stirred at the reflux temp. overnight, cooled to room temp., and separated between EtOAc (50 mL) and a 1N HCl solution (50 mL). The aqueous layer was back-extracted with EtOAc (2×50 mL). The combined organic phases were sequentially washed with water (2×50 mL) and a saturated NaCl solution (50 mL), dried (MgSO$_4$), and concentrated under reduced pressure. The residual oil was purified by column chromatography (30% EtOAc/70% hexane) to give 4-(3-(N-methylsulfamoyl)phenyloxy)benzene (0.30 g).

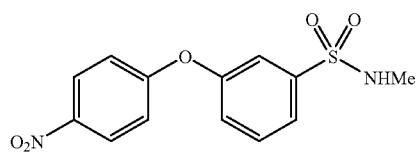

Step 3. Synthesis of 4-(3-(N-methylsulfamoyl)phenyloxy)-1-nitrobenzene

To a solution of 4-(3-(N-methylsulfamoyl)phenyloxy)benzene (0.30 g, 1.14 mmol) in TFA (6 mL) at −10° C. was added NaNO$_2$ (0.097 g, 1.14 mmol) in portions over 5 min. The resulting solution was stirred at −10° C. for 1 h, then was allowed to warm to room temp., and was concentrated under reduced pressure. The residue was separated between EtOAc (10 mL) and water (10 mL). The organic phase was sequentially washed with water (10 mL) and a saturated NaCl solution (10 mL), dried (MgSO$_4$) and concentrated under reduced pressure to give 4-(3-(N-methylsulfamoyl)phenyloxy)-1-nitrobenzene (0.20 g). This material carried on to the next step without further purification.

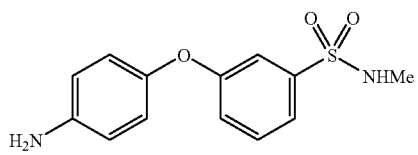

Step 4. Synthesis of 4-(3-(N-methylsulfamoyl)phenyloxy)aniline

A slurry of 4-(3-(N-methylsulfamoyl)phenyloxy)-1-nitrobenzene (0.30 g) and 10% Pd/C (0.030 g) in EtOAc (20 mL) was stirred under an H$_2$ atmosphere (balloon) overnight. The resulting mixture was filtered through a pad of Celite®. The filtrate was concentrated under reduced pressure. The residue was purified by column chromatography (30% EtOAc/70% hexane) to give 4-(3-(N-methylsulfamoyl)phenyloxy)aniline (0.070 g).

A16. Modification of ω-ketones. Synthesis of 4-(4-(1-(N-methoxy)iminoethyl)phenoxyaniline HCl salt

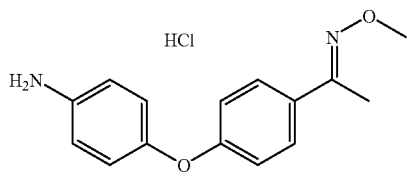

To a slurry of 4-(4-acetylphenoxy)aniline HCl salt (prepared in a manner analogous to Method A13, step 4; 1.0 g, 3.89 mmol) in a mixture of EtOH (10 mL) and pyridine (1.0 mL) was added O-methylhydroxylamine HCl salt (0.65 g, 7.78 mmol, 2.0 equiv.). The resulting solution was heated at the reflux temperature for 30 min, cooled to room temperature and concentrated under reduced pressure. The resulting solids were triturated with water (10 mL) and washed with water to give 4-(4-(1-(N-methoxy)iminoethyl)phenoxyaniline HCl salt as a yellow solid (0.85 g): TLC (50% EtOAc/50% pet. ether) R$_f$ 0.78; $^1$H NMR (DMSO-d$_6$) δ3.90 (s, 3H), 5.70 (s, 3H); HPLC-MS m/z 257 ((M+H)$^+$).

A17. Synthesis of N-(ω-Silyloxyalkyl)amides. Synthesis of 4-(4-(2-(N-(2-Triisopropylsilyloxy)ethylcarbamoyl)pyridyloxyaniline.

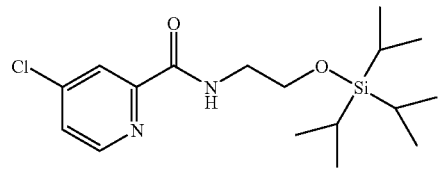

Step 1. 4-Chloro-N-(2-triisopropylsilyloxy)ethylpyridine-2-carboxamide

To a solution of 4-chloro-N-(2-hydroxyethyl)pyridine-2-carboxamide (prepared in a manner analogous to Method A2, Step 3b; 1.5 g, 7.4 mmol) in anh DMF (7 mL) was added triisopropylsilyl chloride (1.59 g, 8.2 mmol, 1.1 equiv.) and imidazole (1.12 g, 16.4 mmol, 2.2 equiv.). The resulting yellow solution was stirred for 3 h at room temp, then was concentrated under reduced pressure. The residue was separated between water (10 mL) and EtOAc (10 mL). The aqueous layer was extracted with EtOAc (3×10 mL). The combined organic phases were dried (MgSO$_4$), and concentrated under reduced pressure to afford 4-chloro-2-(N-(2-triisopropylsilyloxy)ethyl)pyridinecarboxamide as an orange oil (2.32 g, 88%). This material was used in the next step without further purification.

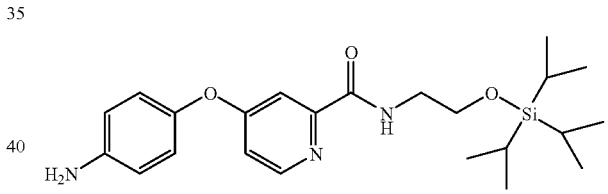

Step 2. 4-(4-(2-(N-(2-Triisopropylsilyloxy)ethylcarbamoyl)pyridyloxyaniline

To a solution of 4-hydroxyaniline (0.70 g, 6.0 mmol) in anh DMF (8 mL) was added potassium tert-butoxide (0.67 g, 6.0 mmol, 1.0 equiv) in one portion causing an exotherm. When this mixture had cooled to room temperature, a solution of 4-chloro-2-(N-(2-triisopropylsilyloxy)ethyl)pyridinecarboxamide (2.32 g, 6 mmol, 1 eq.) in DMF (4 mL) was added followed by K$_2$CO$_3$ (0.42 g, 3.0 mmol, 0.50 equiv). The resulting mixture was heated at 80° C. overnight. An additional portion of potassium tert-butoxide (0.34 g, 3 mmol, 0.5 equiv) was then added and the mixture was stirred at 80° C. an additional 4 h. The mixture was cooled to 0° C. with an ice/water bath, then water (approx. 1 mL) was slowly added dropwise. The organic layer was extracted with EtOAc (3×10 mL). The combined organic layers were washed with a saturated NaCl solution (20 mL), dried (MgSO$_4$) and concentrated under reduced pressure. The brown oily residue was purified by column chromatography (SiO$_2$; 30% EtOAc/70% pet ether) to afford 4-(4-(2-(N-(2-triisopropylsilyloxy)ethylcarbamoyl)pyridyloxyaniline as a clear light brown oil (0.99 g, 38%).

A18. Synthesis of 2-Pryidinecarboxylate Esters via Oxidation of 2-Methylpyridines. Synthesis of 4-(5-(2-methoxycarbonyl)pyridyloxy)aniline

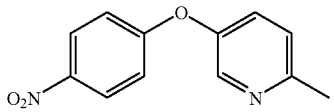

Step 1. 4-(5-(2-Methyl)pyridyloxy)-1-nitrobenzene

A mixture of 5-hydroxy-2-methylpyridine (10.0 g, 91.6 mmol), 1-fluoro-4-nitrobenzene (9.8 mL, 91.6 mmol, 1.0 equiv), K₂CO₃ (25 g, 183 mmol, 2.0 equiv) in DMF (100 mL) was heated at the reflux temperature overnight. The resulting mixture was cooled to room temperature, treated with water (200 mL), and extracted with EtOAc (3×100 mL). The combined organic layers were sequentially washed with water (2×100 mL) and a saturated NaCl solution ((100 mL), dried (MgSO₄, and concentrated under reduced pressure to give 4-(5-(2-methyl)pyridyloxy)-1-nitrobenzene as a brown solid (12.3 g).

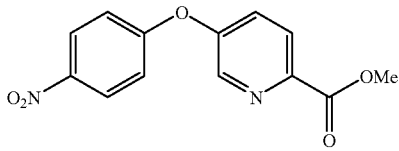

Step 2. Synthesis of 4-(5-(2-Methoxycarbonyl)pyridyloxy)-1-nitrobenzene

A mixture of 4-(5-(2-methyl)pyridyloxy)-1-nitrobenzene (1.70 g, 7.39 mmol) and selenium dioxide (2.50 g, 22.2 mmol, 3.0 equiv) in pyridine (20 mL) was heated at the reflux temperature for 5 h, then cooled to room temperature. The resulting slurry was filtered, then concentrated under reduced pressure. The residue was dissolved in MeOH (100 mL). The solution was treated with a conc HCl solution (7 mL), then heated at the reflux temperature for 3 h, cooled to room temperature and concentrated under reduced pressure. The residue was separated between EtOAc (50 mL) and a 1N NaOH solution (50 mL). The aqueous layer was extracted with EtOAc (2×50 mL). The combined organic layers were sequentially washed with water (2×50 mL) and a saturated NaCl solution (50 mL), dried (MgSO₄) and concentrated under reduced pressure. The residue was purified by column chromatography (SiO₂; 50% EtOAc/50% hexane) to afford 4-(5-(2-methoxycarbonyl)pyridyloxy)-1-nitrobenzene (0.70 g).

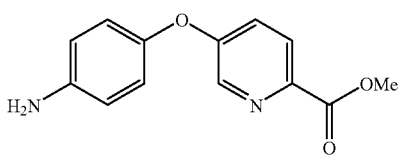

Step 3. Synthesis of 4-(5-(2-Methoxycarbonyl)pyridyloxy)aniline

A slurry of 4-(5-(2-methoxycarbonyl)pyridyloxy)-1-nitrobenzene (0.50 g) and 10% Pd/C (0.050 g) in a mixture of EtOAc (20 mL) and MeOH (5 mL) was placed under a H₂ atmosphere (balloon) overnight. The resulting mixture was filtered through a pad of Celite®, and the filtrate was concentrated under reduced pressure. The residue was purified by column chromatography (SiO₂; 70% EtOAc/30% hexane) to give 4-(5-(2-methoxycarbonyl)pyridyloxy)aniline (0.40 g).

A19. Synthesis of ω-Sulfonylphenyl Anilines. Synthesis of 4-(4-Methylsulfonylphenyoxy)aniline

Step 2. 4-(4-Methylsulfonylphenoxy)-1-aniline 4-(4-Methylsulfonylphenoxy)-1-nitrobenzene was reduced to the aniline in a manner analogous to that described in Method A17, step 3.

B. Synthesis of Urea Precursors

B1. General Method for the Synthesis of Isocyanates from Anilines Using CDI. Synthesis of 4-Bromo-3-(trifluoromethyl)phenyl Isocyanate.

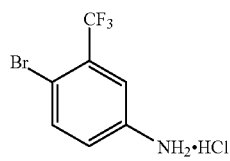

Step 1. Synthesis of 4-bromo-3-(trifluoromethyl)aniline HCl salt

To a solution of 4-bromo-3-(trifluoromethyl)aniline (64 g, 267 mmol) in Et₂O (500 mL) was added an HCl solution (1M in Et₂O; 300 mL) dropwise and the resulting mixture was stirred at room temp. for 16 h. The resulting pink-white precipitate was removed by filtration and washed with Et₂O (50 mL) and to afford 4-bromo-3-(trifluoromethyl)aniline HCl salt (73 g, 98%).

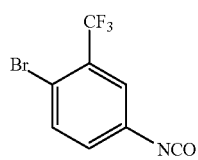

Step 2. Synthesis of 4-bromo-3-(trifluoromethyl)phenyl isocyanate

A suspension of 4-bromo-3-(trifluoromethyl)aniline HCl salt (36.8 g, 133 mmol) in toluene (278 mL) was treated with trichloromethyl chloroformate dropwise and the resulting mixture was heated at the reflux temp. for 18 h. The resulting mixture was concentrated under reduced pressure. The residue was treated with toluene (500 mL), then concentrated under reduced pressure. The residue was treated with CH$_2$Cl$_2$ (500 mL), then concentrated under reduced pressure. The CH$_2$Cl$_2$ treatment/concentration protocol was repeated and resulting amber oil was stored at −20° C. for 16 h, to afford 4-bromo-3-(trifluoromethyl)phenyl isocyanate as a tan solid (35.1 g, 86%): GC-MS m/z 265 (M$^+$).

C. Methods of Urea Formation

C1a. General Method for the Synthesis of Ureas by Reaction of an Isocyanate with an Aniline. Synthesis of N-(4-Chloro-3-(trifluoromethyl)phenyl)-N'-(4-(2-(N-methylcarbamoyl)-4-pyridyloxy)phenyl) Urea

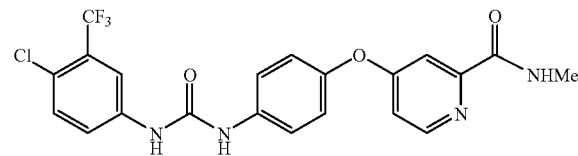

A solution of 4-chloro-3-(trifluoromethyl)phenyl isocyanate (14.60 g, 65.90 mmol) in CH$_2$Cl$_2$ (35 mL) was added dropwise to a suspension of 4-(2-(N-methylcarbamoyl)-4-pyridyloxy)aniline (Method A2, Step 4; 16.0 g, 65.77 mmol) in CH$_2$Cl$_2$ (35 mL) at 0° C. The resulting mixture was stirred at room temp. for 22 h. The resulting yellow solids were removed by filtration, then washed with CH$_2$Cl$_2$ (2×30 mL) and dried under reduced pressure (approximately 1 mmHg) to afford N-(4-chloro-3-(trifluoromethyl)phenyl)-N'-(4-(2-(N-methylcarbamoyl)-4-pyridyloxy)phenyl) urea as an off-white solid (28.5 g, 93%): mp 207-209° C.; $^1$H-NMR (DMSO-d$_6$) δ2.77 (d, J=4.8 Hz, 3H), 7.16 (m, 3H), 7.37 (d, J=2.5 Hz, 1H), 7.62 (m, 4H), 8.11 (d, J=2.5 Hz, 1H), 8.49 (d, J=5.5 Hz, 1H), 8.77 (br d, 1H), 8.99 (s, 1H), 9.21 (s, 1H); HPLC ES-MS m/z 465 ((M+H)$^+$).

C1b. General Method for the Synthesis of Ureas by Reaction of an Isocyanate with an Aniline. Synthesis of N-(4-Bromo-3-(trifluoromethyl)phenyl)-N'-(4-(2-(N-methylcarbamoyl)-4-pyridyloxy)phenyl) Urea

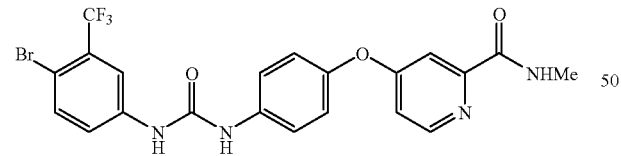

A solution of 4-bromo-3-(trifluoromethyl)phenyl isocyanate (Method B1, Step 2; 8.0 g, 30.1 mmol) in CH$_2$Cl$_2$ (80 mL) was added dropwise to a solution of 4-(2-(N-methylcarbamoyl)-4-pyridyloxy)aniline (Method A2, Step 4; 7.0 g, 28.8 mmol) in CH$_2$Cl$_2$ (40 mL) at 0° C. The resulting mixture was stirred at room temp. for 16 h. The resulting yellow solids were removed by filtration, then washed with CH$_2$Cl$_2$ (2×50 mL) and dried under reduced pressure (approximately 1 mmHg) at 40° C. to afford N-(4-bromo-3-(trifluoromethyl)phenyl)-N'-(4-(2-(N-methylcarbamoyl)-4-pyridyloxy)phenyl) urea as a pale-yellow solid (13.2 g, 90%): mp 203-205° C.; $^1$H-NMR (DMSO-d$_6$) δ2.77 (d, J=4.8 Hz, 3H), 7.16 (m, 3H), 7.37 (d, J=2.5 Hz, 1H), 7.58 (m, 3H), 7.77 (d, J=8.8 Hz, 1H), 8.11 (d, J=2.5 Hz, 1H), 8.49 (d, J=5.5 Hz, 1H), 8.77 (br d, 1H), 8.99 (s, 1H), 9.21 (s, 1H); HPLC ES-MS m/z 509 ((M+H)$^+$).

C1c. General Method for the Synthesis of Ureas by Reaction of an Isocyanate with an Aniline. Synthesis of N-(4-Chloro-3-(trifluoromethyl)phenyl)-N'-(2-methyl-4-(2-(N-methylcarbamoyl)(4-pyridyloxy)) phenyl) Urea

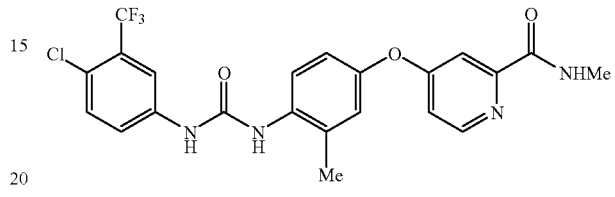

A solution of 2-methyl-4-(2-(N-methylcarbamoyl)(4-pyridyloxy))aniline (Method A5; 0.11 g, 0.45 mmol) in CH$_2$Cl$_2$ (1 mL) was treated with Et$_3$N (0.16 mL) and 4-chloro-3-(trifluoromethyl)phenyl isocyanate (0.10 g, 0.45 mmol). The resulting brown solution was stirred at room temp. for 6 d, then was treated with water (5 mL). The aqueous layer was back-extracted with EtOAc (3×5 mL). The combined organic layers were dried (MgSO$_4$) and concentrated under reduced pressure to yield N-(4-chloro-3-(trifluoromethyl)phenyl)-N'-(2-methyl-4-(2-(N-methylcarbamoyl)(4-pyridyloxy))phenyl) urea as a brown oil (0.11 g, 0.22 mmol): $^1$H NMR (DMSO-d$_6$) δ2.27 (s, 3H), 2.77 (d, J=4.8 Hz, 3H), 7.03 (dd, J=8.5, 2.6 Hz, 1H), 7.11 (d, J=2.9 Hz, 1H), 7.15 (dd, J=5.5, 2.6, Hz, 1H), 7.38 (d, J=2.6 Hz, 1H), 7.62 (app d, J=2.6 Hz, 2H), 7.84 (d, J=8.8 Hz, 1H), 8.12 (s, 1H), 8.17 (s, 1H); 8.50 (d, J=5.5 Hz, 1H), 8.78 (q, J=5.2, 1H), 9.52 (s, 1H); HPLC ES-MS m/z 479 ((M+H)$^+$).

C1d. General Method for the Synthesis of Ureas by Reaction of an Isocyanate with an Aniline. Synthesis of N-(4-Chloro-3-(trifluoromethyl)phenyl)-N'-(4-aminophenyl) Urea

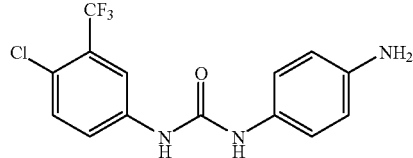

To a solution of 4-chloro-3-(trifluoromethyl)phenyl isocyanate (2.27 g, 10.3 mmol) in CH$_2$Cl$_2$ (308 mL) was added p-phenylenediamine (3.32 g, 30.7 mmol) in one part. The resulting mixture was stirred at room temp. for 1 h, treated with CH$_2$Cl$_2$ (100 mL), and concentrated under reduced pressure. The resulting pink solids were dissolved in a mixture of EtOAc (110 mL) and MeOH (15 mL), and the clear solution was washed with a 0.05N HCl solution. The organic layer was concentrated under reduced pressure to afford impure N-(4-chloro-3-(trifluoromethyl)phenyl)-N'-(4-aminophenyl) urea (3.3 g): TLC (100% EtOAc) R$_f$ 0.72.

C1e. General Method for the Synthesis of Ureas by Reaction of an Isocyanate with an Aniline. Synthesis of N-(4-Chloro-3-(trifluoromethyl)phenyl)-N'-(4-ethoxycarbonylphenyl) Urea

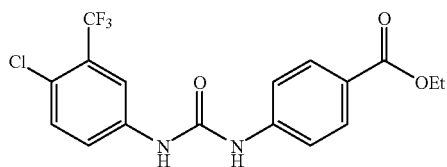

To a solution of ethyl 4-isocyanatobenzoate (3.14 g, 16.4 mmol) in $CH_2Cl_2$ (30 mL) was added 4-chloro-3-(trifluoromethyl)aniline (3.21 g, 16.4 mmol), and the solution was stirred at room temp. overnight. The resulting slurry was diluted with $CH_2Cl_2$ (50 mL) and filtered to afford N-(4-chloro-3-(trifluoromethyl)phenyl)-N'-(4-ethoxycarbonylphenyl) urea as a white solid (5.93 g, 97%): TLC (40% EtOAc/60% hexane) $R_f$ 0.44.

C1f. General Method for the Synthesis of Ureas by Reaction of an Isocyanate with an Aniline. Synthesis of N-(4-Chloro-3-(trifluoromethyl)phenyl)-N'-(3-carboxyphenyl) Urea

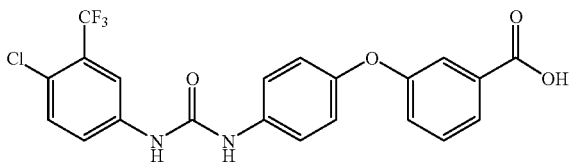

To a solution of 4-chloro-3-(trifluoromethyl)phenyl isocyanate (1.21 g, 5.46 mmol) in $CH_2Cl_2$ (8 mL) was added 4-(3-carboxyphenoxy)aniline (Method A11; 0.81 g, 5.76 mmol) and the resulting mixture was stirred at room temp. overnight, then treated with MeOH (8 mL), and stirred an additional 2 h. The resulting mixture was concentrated under reduced pressure. The resulting brown solids were triturated with a 1:1 EtOAc/hexane solution to give N-(4-chloro-3-(trifluoromethyl)phenyl)-N'-(3-carboxyphenyl) urea as an off-white solid (1.21 g, 76%).

C2a. General Method for Urea Synthesis by Reaction of an Aniline with N,N'-Carbonyl Diimidazole Followed by Addition of a Second Aniline. Synthesis of N-(2-Methoxy-5-(trifluoromethyl)phenyl)-N'-(4-(2-(N-methylcarbamoyl)-4-pyridyloxy)phenyl) Urea

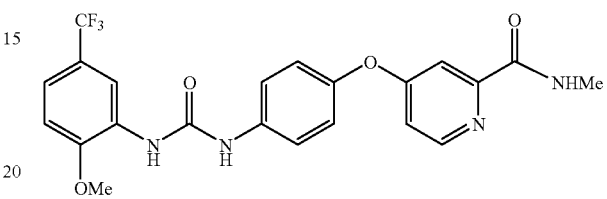

To a solution of 2-methoxy-5-(trifluoromethyl)aniline (0.15 g) in anh $CH_2Cl_2$ (15 mL) at 0° C. was added CDI (0.13 g). The resulting solution was allowed to warm to room temp. over 1 h, was stirred at room temp. for 16 h, then was treated with 4-(2-(N-methylcarbamoyl)-4-pyridyloxy)aniline (0.18 g). The resulting yellow solution was stirred at room temp. for 72 h, then was treated with $H_2O$ (125 mL). The resulting aqueous mixture was extracted with EtOAc (2×150 mL). The combined organics were washed with a saturated NaCl solution (100 mL), dried ($MgSO_4$) and concentrated under reduced pressure. The residue was triturated (90% EtOAc/10% hexane). The resulting white solids were collected by filtration and washed with EtOAc. The filtrate was concentrated under reduced pressure and the residual oil purified by column chromatography (gradient from 33% EtOAc/67% hexane to 50% EtOAc/50% hexane to 100% EtOAc) to give N-(2-methoxy-5-(trifluoromethyl)phenyl)-N'-(4-(2-(N-methylcarbamoyl)-4-pyridyloxy)phenyl) urea as a light tan solid (0.098 g, 30%): TLC (100% EtOAc) $R_f$ 0.62; $^1$H NMR (DMSO-$d_6$) δ2.76 (d, J=4.8 Hz, 3H), 3.96 (s, 3H), 7.1-7.6 and 8.4-8.6 (m, 11H), 8.75 (d, J=4.8 Hz, 1H), 9.55 (s, 1H); FAB-MS m/z 461 ((M+H)$^+$).

C2b. General Method for Urea Synthesis by Reaction of an Aniline with N,N'-Carbonyl Diimidazole Followed by Addition of a Second Aniline. Symmetrical Urea's as Side Products of a N,N'-Carbonyl Diimidazole Reaction Procedure. Synthesis of Bis(4-(2-(N-methylcarbamoyl)-4-pyridyloxy)phenyl) Urea

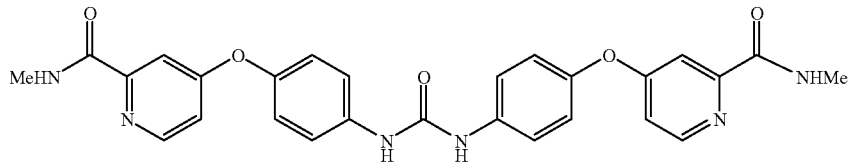

To a stirring solution of 3-amino-2-methoxyquinoline (0.14 g) in anhydrous CH$_2$Cl$_2$ (15 mL) at 0 C was added CDI (0.13 g). The resulting solution was allowed to warm to room temp. over 1 h then was stirred at room temp. for 16 h. The resulting mixture was treated with 4-(2-(N-methylcarbamoyl)-4-pyridyloxy)aniline (0.18 g). The resulting yellow solution stirred at room temp. for 72 h, then was treated with water (125 mL). The resulting aqueous mixture was extracted with EtOAc (2×150 mL). The combined organic phases were washed with a saturated NaCl solution (100 ml), dried (MgSO$_4$) and concentrated under reduced pressure. The residue was triturated (90% EtOAc/10% hexane). The resulting white solids were collected by filtration and washed with EtOAc to give bis(4-(2-(N-methylcarbamoyl)-4-pyridyloxy) phenyl) urea (0.081 g, 44%): TLC (100% EtOAc) R$_f$ 0.50; $^1$H NMR (DMSO-d$_6$) δ 2.76 (d, J=5.1 Hz, 6H), 7.1-7.6 (m, 12H), 8.48 (d, J=5.4 Hz, 1H), 8.75 (d, J=4.8 Hz, 2H), 8.86 (s, 2H); HPLC ES-MS m/z 513 ((M+H)$^+$).

C2c. General Method for the Synthesis of Ureas by Reaction of an Isocyanate with an Aniline. Synthesis of N-(2-Methoxy-5-(trifluoromethyl)phenyl-N'-(4-(1,3-dioxoisoindolin-5-yloxy)phenyl) Urea

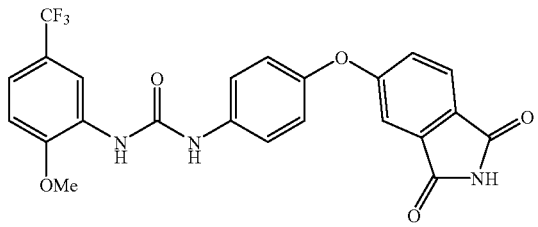

To a stirring solution of 2-methoxy-5-(trifluoromethyl) phenyl isocyanate (0.10 g, 0.47 mmol) in CH$_2$Cl$_2$ (1.5 mL) was added 5-(4-aminophenoxy)isoindoline-1,3-dione (Method A3, Step 3; 0.12 g, 0.47 mmol) in one portion. The resulting mixture was stirred for 12 h, then was treated with CH$_2$Cl$_2$ (10 mL) and MeOH (5 mL). The resulting mixture was sequentially washed with a 1N HCl solution (15 mL) and a saturated NaCl solution (15 mL), dried (MgSO$_4$) and concentrated under reduced pressure to afford N-(2-methoxy-5-(trifluoromethyl)phenyl-N'-(4-(1,3-dioxoisoindolin-5-yloxy)phenyl) urea as a white solid (0.2 g, 96%): TLC (70% EtOAc/30% hexane) R$_f$ 0.50; $^1$H NMR (DMSO-d$_6$) δ 3.95 (s, 3H), 7.31-7.10 (m, 6H), 7.57 (d, J=9.3 Hz, 2H), 7.80 (d, J=8.7 Hz, 1H), 8.53 (br s, 2H), 9.57 (s, 1H), 11.27 (br s, 1H); HPLC ES-MS 472.0 ((M+H)$^+$, 100%).

C2d. General Method for Urea Synthesis by Reaction of an Aniline with N,N'-Carbonyl Diimidazole Followed by Addition of a Second Aniline. Synthesis of N-(5-(tert-Butyl)-2-(2,5-dimethylpyrrolyl)phenyl)-N'-(4-(2-(N-methylcarbamoyl)-4-pyridyloxy) phenyl) Urea

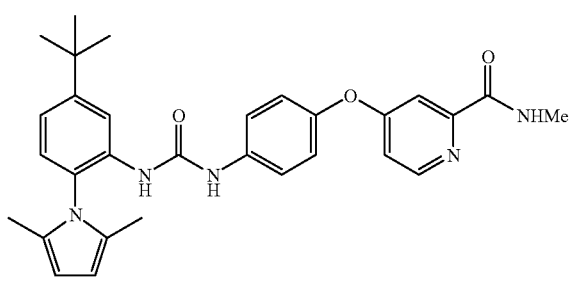

To a stirring solution of CDI (0.21 g, 1.30 mmol) in CH$_2$Cl$_2$ (2 mL) was added 5-(tert-butyl)-2-(2,5-dimethylpyrrolyl) aniline (Method A4, Step 2; 0.30 g, 1.24 mmol) in one portion. The resulting mixture was stirred at room temp. for 4 h, then 4-(2-(N-methylcarbamoyl)-4-pyridyloxy)aniline (0.065 g, 0.267 mmol) was then added in one portion. The resulting mixture was heated at 36° C. overnight, then cooled to room temp. and diluted with EtOAc (5 mL). The resulting mixture was sequentially washed with water (15 mL) and a 1N HCl solution (15 mL), dried (MgSO$_4$), and filtered through a pad of silica gel (50 g) to afford N-(5-(tert-butyl)-2-(2,5-dimethylpyrrolyl)phenyl)-N'-(4-(2-(N-methylcarbamoyl)-4-pyridyloxy)phenyl) urea as a yellowish solid (0.033 g, 24%): TLC (40% EtOAc/60% hexane) R$_f$ 0.24; $^1$H NMR (acetone-d$_6$) δ 1.37 (s, 9H), 1.89 (s, 6H), 2.89 (d, J=4.8 Hz, 3H), 5.83 (s, 2H), 6.87-7.20 (m, 6H), 7.17 (dd, 1H), 7.51-7.58 (m, 3H), 8.43 (d, J=5.4 Hz, 1H), 8.57 (d, J=2.1 Hz, 1H), 8.80 (br s, 1H); HPLC ES-MS 512 ((M+H)$^+$, 100%).

C2e. General Method for Urea Synthesis by Reaction of an Aniline with N,N'-Carbonyl Diimidazole Followed by Addition of a Second Aniline. Synthesis of N-(4-tert-Butylpyridyl)-N'-(4-(4-chlorophenoxy) phenyl) Urea

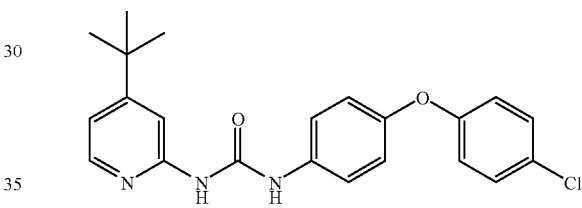

A solution of 4-tert-butyl-2-aminopyridine (0.177 g, 1.18 mmol, 1 equiv.) in 1.2 mL of anh. CH$_2$Cl$_2$ (1.2 mL) was added to CDI (0.200 g, 1.24 mmol, 1.05 equiv) and the mixture was allowed to stir under argon at room temperature 1 d. To the resulting solution was added 4-(4-chlorophenoxy)aniline (0.259 g, 1.18 mmol, 1 equiv.) in one portion. The resulting mixture was stirred at room temperature for 1 d, then was treated with a 10% citric acid solution (2 mL) and allowed to stir for 1 h. The resulting organic layer was extracted with EtOAc (3×5 mL). The combined organic layers were dried (MgSO$_4$) and concentrated in vacuo. The resultant residue was treated with CH$_2$Cl$_2$ (10 mL) and a 1 N aqueous NaOH solution. This mixture was allowed to stir overnight. The resulting organic layer was extracted with CH$_2$Cl$_2$ (3×5 mL). The combined organic layers were dried (MgSO$_4$) and concentrated in vacuo. The resultant solids were suspended in diethyl ether (10 mL) and sonicated for 15 minutes. The resulting white solid were dried to give N-(4-tert-butylpyridyl)-N'-(4-(4-chlorophenoxy)phenyl)urea (42 mg, 9%): mp 198-199° C.

One of the anilines to be coupled was dissolved in dichloroethane (0.10 M). This solution was added to a 8 mL vial (0.5 mL) containing dichloroethane (1 mL). To this was added a bis(trichloromethyl) carbonate solution (0.12 M in dichloroethane, 0.2 mL, 0.4 equiv.), followed by diisopropylethylamine (0.35 M in dichloroethane, 0.2 mL, 1.2 equiv.). The vial was capped and heated at 80° C. for 5 h, then allowed to cool to room temp for approximately 10 h. The second aniline was added (0.10 M in dichloroethane, 0.5 mL, 1.0 equiv.), followed by diisopropylethylamine (0.35 M in dichloroethane, 0.2 mL, 1.2 equiv.). The resulting mixture was heated at 80° C. for 4 h, cooled to room temperature and treated with MeOH (0.5 mL). The resulting mixture was concentrated under reduced pressure and the products were purified by reverse phase HPLC.

C4. General Method for Urea Synthesis by Reaction of an Aniline with Phosgene Followed by Addition of a Second Aniline. Synthesis of N-(2-Methoxy-5-(trifluoromethyl)phenyl)-N'L(4-(2-(N-methylcarbamoyl)-4-pyridyloxy) phenyl) Urea

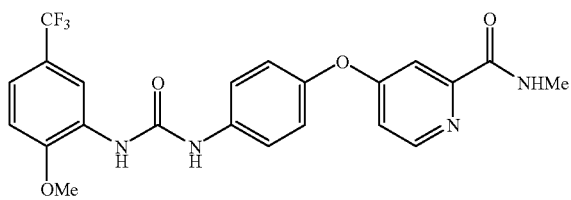

To a stirring solution of phosgene (1.9 M in toluene; 2.07 mL 0.21 g, 1.30 mmol) in CH$_2$Cl$_2$ (20 mL) at 0° C. was added anh pyridine (0.32 mL) followed by 2-methoxy-5-(trifluoromethyl)aniline (0.75 g). The yellow solution was allowed to warm to room temp during which a precipitate formed. The yellow mixture was stirred for 1 h, then concentrated under reduced pressure. The resulting solids were treated with anh toluene (20 mL) followed by 4-(2-(N-methylcarbamoyl)-4-pyridyloxy)aniline (prepared as described in Method A2; 0.30 g) and the resulting suspension was heated at 80° C. for 20 h, then allowed to cool to room temp. The resulting mixture was diluted with water (100 mL), then was made basic with a saturated NaHCO$_3$ solution (2-3 mL). The basic solution was extracted with EtOAc (2×250 mL). The organic layers were separately washed with a saturated NaCl solution, combined, dried (MgSO$_4$), and concentrated under reduced pressure. The resulting pink-brown residue was dissolved in MeOH and absorbed onto SiO$_2$ (100 g). Column chromatography (300 g SiO$_2$; gradient from 1% Et$_3$N/33% EtOAc/66% hexane to 1% Et$_3$N/99% EtOAc to 1% Et$_3$N/20% MeOH/79% EtOAc) followed by concentration under reduced pressure at 45° C. gave a warm concentrated EtOAc solution, which was treated with hexane (10 mL) to slowly form crystals of N-(2-methoxy-5-(trifluoromethyl)phenyl)-N'-(4-(2-(N-methylcarbamoyl)-4-pyridyloxy)phenyl)urea (0.44 g): TLC (1% Et$_3$N/99% EtOAc) R$_f$ 0.40.

C5. General Method for Urea Synthesis by Reaction of an Aniline with Phosgene Followed by Addition of a Second Aniline. Synthesis of N-(3-(2-methoxyquinolinyl)-N'-(4-(4-(2-N-Methylcarbamyl-4-pyridyloxy)phenyl) Urea

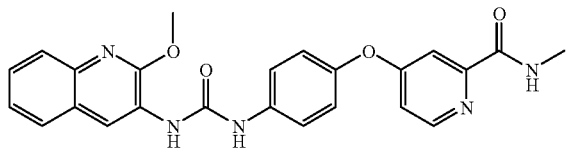

To a stirring solution of phosgene (20% in toluene, 1.38 mL) in anh. CH$_2$Cl$_2$ (20 ml) at 0° C. under argon was added anh. pyridine (207 mg) followed by 3-amino-2-methoxyquinoline (456 mg). The resulting solution was warmed to ambient temperature over 1 h, then concentrated in vacuo at ambient temperature to give a white solid. The solid was dried under vacuum for 15 min then suspended in anh toluene (20 mL). To the resulting slurry was added 4-(4-(2-(methylcarbamoyl)pyridyloxy)aniline (prepared according to Method A2, 300 mg) and the reaction heated under argon at 80° C. for 20 h. The resulting mixture was diluted with water (200 mL), then treated with a saturated NaHCO$_3$ solution (10 mL) and extracted with EtOAc (2×300 mL). The combined organic layers were washed with a saturated NaCl solution (100 mL), dried (MgSO$_4$) and concentrated under reduced pressure. The solid yellow residue was purified by chromatography (SiO$_2$, gradient from 50% EtOAc/50% hexane to 100% EtOAc), followed by recrystallization from diethyl ether and hexane to give N-(3-(2-methoxyquinolinyl)-N'-(4-(4-(2-N-Methylcarbamyl-4-pyridyloxy)phenyl) urea as a white solid (140 mg, 25%): TLC (EtOAc) R$_f$ 0.52; FAB-MS m/z 430 ((M+H)$^+$).

D. Interconversion of Ureas

D1a. Conversion of ω-Aminophenyl Ureas into ω-(Arylamino)phenyl Ureas. Synthesis of N-(4-Chloro-3-((trifluoromethyl)phenyl)-N'-(4-(3-methoxycarbonylphenyl)carboxyaminophenyl) Urea

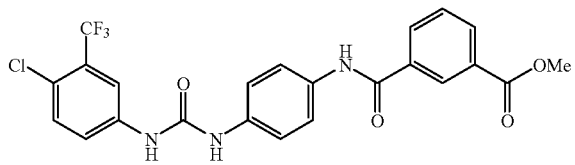

To a solution of N-(4-chloro-3-((trifluoromethyl)phenyl)-N'-(4-aminophenyl) urea (Method C1d; 0.050 g, 1.52 mmol), mono-methyl isophthalate (0.25 g, 1.38 mmol), HOBT.H$_2$O (0.41 g, 3.03 mmol) and N-methylmorpholine (0.33 mL, 3.03 mmol) in DMF (8 mL) was added EDCI.HCl (0.29 g, 1.52 mmol). The resulting mixture was stirred at room temp. overnight, diluted with EtOAc (25 mL) and sequentially washed with water (25 mL) and a saturated NaHCO$_3$ solution (25 mL). The organic layer was dried (Na$_2$SO$_4$) and concentrated under reduced pressure. The resulting solids were triturated with an EtOAc solution (80% EtOAc/20% hexane) to give N-(4-chloro-3-((trifluoromethyl)phenyl)-N'-(4-(3-methoxycarbonylphenyl)carboxyaminophenyl) urea (0.27 g, 43%): mp 121-122; TLC (80% EtOAc/20% hexane) R$_f$ 0.75.

D1b. Conversion of ω-Carboxyphenyl Ureas into ω-(Arylcarbamoyl)phenyl Ureas. Synthesis of N-(4-Chloro-3-((trifluoromethyl)phenyl)-N'-(4-(3-methylcarbamoylphenyl)carbamoylphenyl) Urea

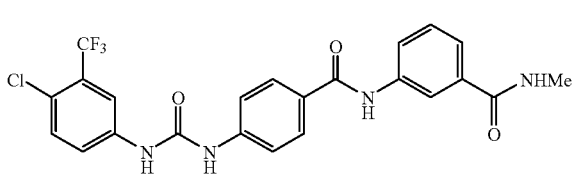

To a solution of N-(4-chloro-3-((trifluoromethyl)phenyl)-N'-(4-(3-methylcarbamoylphenyl)carboxyaminophenyl) urea (0.14 g, 0.48 mmol), 3-methylcarbamoylaniline (0.080 g, 0.53 mmol), HOBT·H₂O (0.14 g, 1.07 mmol), and N-methylmorpholine (0.5 mL, 1.07 mmol) in DMF (3 mL) at 0° C. was added EDCI·HCl (0.10 g, 0.53 mmol). The resulting mixture was allowed to warm to room temp. and was stirred overnight. The resulting mixture was treated with water (10 mL), and extracted with EtOAc (25 mL). The organic phase was concentrated under reduced pressure. The resulting yellow solids were dissolved in EtOAc (3 mL) then filtered through a pad of silica gel (17 g, gradient from 70% EtOAc/30% hexane to 10% MeOH/90% EtOAc) to give N-(4-chloro-3-((trifluoromethyl)phenyl)-N'-(4-(3-methylcarbamoylphenyl)carbamoylphenyl) urea as a white solid (0.097 g, 41%): mp 225-229; TLC (100% EtOAc) R$_f$ 0.23.

D1c. Combinatorial Approach to the Conversion of ω-Carboxyphenyl Ureas into ω-(Arylcarbamoyl)phenyl Ureas. Synthesis of N-(4-Chloro-3-((trifluoromethyl)phenyl)-N'-(4-(N-(3-(N-(3-pyridyl)carbamoyl)phenyl)carbamoyl)phenyl) Urea

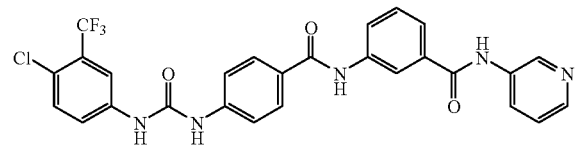

A mixture of N-(4-chloro-3-((trifluoromethyl)phenyl)-N'-(3-carboxyphenyl) urea (Method C1f; 0.030 g, 0.067 mmol) and N-cyclohexyl-N'-(methylpolystyrene)carbodiimide (55 mg) in 1,2-dichloroethane (1 mL) was treated with a solution of 3-aminopyridine in CH₂Cl₂ (1M; 0.074 mL, 0.074 mmol). (In cases of insolubility or turbidity, a small amount of DMSO was also added.) The resulting mixture was heated at 36° C. overnight. Turbid reactions were then treated with THF (1 mL) and heating was continued for 18 h. The resulting mixtures were treated with poly(4-(isocyanatomethyl)styrene) (0.040 g) and the resulting mixture was stirred at 36° C. for 72 h, then cooled to room temp. and filtered. The resulting solution was filtered through a plug of silica gel (1 g). Concentration under reduced pressure afforded N-(4-chloro-3-((trifluoromethyl)phenyl)-N'-(4-(N-(3-(N-(3-pyridyl) carbamoyl) phenyl)carbamoyl)phenyl) urea (0.024 g, 59%): TLC (70% EtOAc/30% hexane) R$_f$ 0.12.

D2. Conversion of ω-Carboalkoxyaryl Ureas into ω-Carbamoylaryl Ureas. Synthesis of N-(4-Chloro-3-((trifluoromethyl)phenyl)-N'-(4-(3-methylcarbamoylphenyl)carboxyaminophenyl) Urea

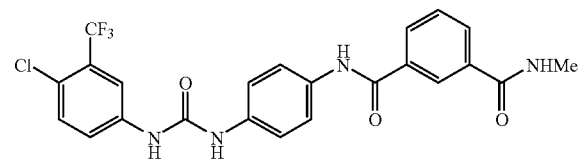

To a sample of N-(4-chloro-3-((trifluoromethyl)phenyl)-N'-(4-(3-carbomethoxyphenyl)carboxyaminophenyl) urea (0.17 g, 0.34 mmol) was added methylamine (2M in THF; 1 mL, 1.7 mmol) and the resulting mixture was stirred at room temp. overnight, then concentrated under reduced pressure to give N-(4-chloro-3-((trifluoromethyl)phenyl)-N'-(4-(3-methylcarbamoylphenyl)carboxyaminophenyl) urea as a white solid: mp 247; TLC (100% EtOAc) R$_f$ 0.35.

D3. Conversion of ω-Carboalkoxyaryl Ureas into ω-Carboxyaryl Ureas. Synthesis of N-(4-Chloro-3-((trifluoromethyl)phenyl)-N'-(4-carboxyphenyl) Urea

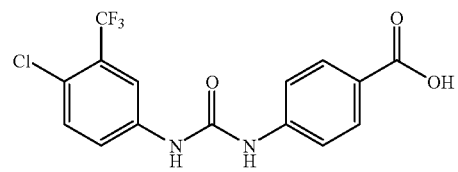

To a slurry of N-(4-chloro-3-((trifluoromethyl)phenyl)-N'-(4-ethoxycarbonylphenyl) urea (Method C1e; 5.93 g, 15.3 mmol) in MeOH (75 mL) was added an aqueous KOH solution (2.5N, 10 mL, 23 mmol). The resulting mixture was heated at the reflux temp. for 12 h, cooled to room temp., and concentrated under reduced pressure. The residue was diluted with water (50 mL), then treated with a 1N HCl solution to adjust the pH to 2 to 3. The resulting solids were collected and dried under reduced pressure to give N-(4-chloro-3-((trifluoromethyl)phenyl)-N'-(4-carboxyphenyl) urea as a white solid (5.05 g, 92%).

D4. General Method for the Conversion of ω-Alkoxy Esters into ω-Alkyl Amides. Synthesis of N-(4-Chloro-3-((trifluoromethyl)phenyl)-N'-((4-(3-(5-(2-dimethylaminoethyl)carbamoyl)pyridyl)oxyphenyl) Urea

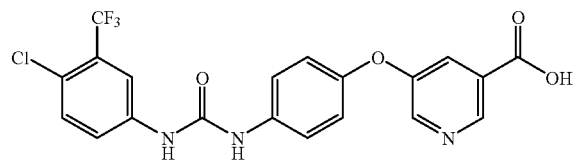

Step 1. Synthesis of N-(4-Chloro-3-(trifluoromethyl)phenyl)-N-((4-(3-(5-carboxypyridyl)oxyphenyl) Urea N-(4-Chloro-3-(trifluoromethyl)phenyl)-N'-((4-(3-(5-methoxycarbonylpyridyl)oxyphenyl)urea was synthesized from 4-chloro-3-(trifluoromethyl)phenyl isocyanate and 4-(3-(5-methoxycarbonylpyridyl)oxyaniline (Method A14, Step 2) in a manner analogous to Method C1a. A suspension of N-(4-Chloro-3-(trifluoromethyl)phenyl)-N'-((4-(3-(5-methoxycarbonylpyridyl)oxyphenyl)urea (0.26 g, 0.56 mmol) in MeOH (10 mL) was treated with a solution of KOH (0.14 g, 2.5 mmol) in water (1 mL) and was stirred at room temp. for 1 h. The resulting mixture was adjusted to pH 5 with a 1 N HCl solution. The resulting precipitate was removed by filtration and washed with water. The resulting solids were dissolved in EtOH (10 mL) and the resulting solution was concentrated under reduced pressure. The EtOH/concentration procedure was repeated twice to give N-(4-chloro-3-(trifluoromethyl)phenyl)-N'-((4-(3-(5-carboxypyridyl)oxyphenyl)urea (0.18 g, 71%).

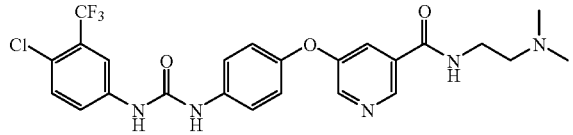

Step 2. Synthesis of N-(4-chloro-3-(trifluoromethyl) phenyl)-N'-((4-(3-(5-(2-dimethylaminoethyl) carbamoyl)pyridyl)oxyphenyl) urea A mixture of N-(4-chloro-3-(trifluoromethyl)phenyl)-N'-((4-(3-(5-carboxypyridyl)oxyphenyl) urea (0.050 g, 0.011 mmol), N,N-dimethylethylenediamine (0.22 mg, 0.17 mmol), HOBT (0.028 g, 0.17 mmol), N-methylmorpholine (0.035 g, 0.28 mmol), and EDCI.HCl (0.032 g, 0.17 mmol) in DMF (2.5 mL) was stirred at room temp. overnight. The resulting solution was separated between EtOAc (50 mL) and water (50 mL). The organic phase was washed with water (35 mL), dried (MgSO$_4$) and concentrated under reduced pressure. The residue was dissolved in a minimal amount of CH$_2$Cl$_2$ (approximately 2 mL). The resulting solution was treated with Et$_2$O dropwise to give N-(4-chloro-3-(trifluoromethyl)phenyl)-N'-((4-(3-(5-(2-dimethylaminoethyl)carbamoyl)pyridyl)oxyphenyl) urea as a white precipitate (0.48 g, 84%: $^1$H NMR (DMSO-d$_6$) δ2.10 s, 6H), 3.26 (s, H), 7.03 (d, 2H), 7.52 (d, 2H), 7.60 (m, 3H), 8.05 (s, 1H), 8.43 (s, 1H), 8.58 (t, 1H), 8.69 (s, 1H), 8.90 (s, 1H), 9.14 (s, 1H); HPLC ES-MS m/z 522 ((M+H)$^+$).

D5. General Method for the Deprotection of N-(ω-Silyloxyalkyl)amides. Synthesis of N-(4-Chloro-3-((trifluoromethyl)phenyl)-N'-(4-(4-(2-(N-(2-hydroxy) ethylcarbamoyl)pyridyloxyphenyl) Urea

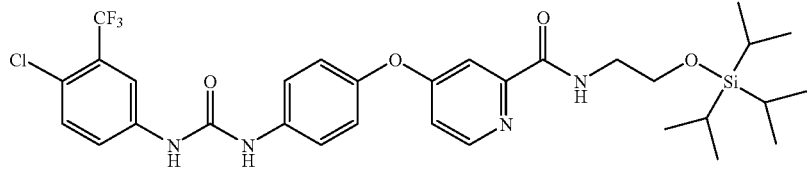

To a solution of N-(4-chloro-3-((trifluoromethyl)phenyl)-N'-(4-(4-(2-(N-(2-triisopropylsilyloxy)ethylcarbamoyl)pyridyloxyphenyl)urea (prepared in a manner analogous to Method C1a; 0.25 g, 0.37 mmol) in anh THF (2 mL) was tetrabutylammonium fluoride (1.0 M in THF; 2 mL). The mixture was stirred at room temperature for 5 min, then was treated with water (10 mL). The aqueous mixture was extracted with EtOAc (3×10 mL). The combined organic layers were dried (MgSO$_4$) and concentrated under reduced pressure. The residue was purified by column chromatography (SiO$_2$; gradient from 100% hexane to 40% EtOAc/60% hexane) to give N-(4-chloro-3-((trifluoromethyl)phenyl)-N'-(4-(4-(2-(N-(2-hydroxy)ethylcarbamoyl)pyridyloxyphenyl) urea as a white solid (0.019 g, 10%).

SYNTHESES OF EXEMPLIFIED COMPOUNDS

See Tables for Compound Characterization

Entry 1: 4-(3-N-Methylcarbamoylphenoxy)aniline was prepared according to Method A13. According to Method C3, 3-tert-butylaniline was reacted with bis(trichloromethyl)carbonate followed by 4-(3-N-Methylcarbamoylphenoxy)aniline to afford the urea.

Entry 2: 4-Fluoro-1-nitrobenzene and p-hydroxyacetophenone were reacted according to Method A13, Step 1 to afford the 4-(4-acetylphenoxy)-1-nitrobenzene. 4-(4-Acetylphenoxy)-1-nitrobenzene was reduced according to Method A13, Step 4 to afford 4-(4-acetylphenoxy)aniline. According to Method C3, 3-tert-butylaniline was reacted with bis(trichloromethyl) carbonate followed by 4-(4-acetylphenoxy)aniline to afford the urea.

Entry 3: According to Method C2d, 3-tert-butylaniline was treated with CDI, followed by 4-(3-N-methylcarbamoyl)-4-methoxyphenoxy)aniline, which had been prepared according to Method A8, to afford the urea.

Entry 4: 5-tert-Butyl-2-methoxyaniline was converted to 5-tert-butyl-2-methoxyphenyl isocyanate according to Method B 1. 4-(3-N-Methylcarbamoylphenoxy)aniline, prepared according to Method A13, was reacted with the isocyanate according to Method C1a to afford the urea.

Entry 5: According to Method C2d, 5-tert-butyl-2-methoxyaniline was reacted with CDI followed by 4-(3-N-methylcarbamoyl)-4-methoxyphenoxy)aniline, which had been prepared according to Method A8, to afford the urea.

Entry 6: 5-(4-Aminophenoxy)isoindoline-1,3-dione was prepared according to Method A3. According to Method 2d, 5-tert-butyl-2-methoxyaniline was reacted with CDI followed by 5-(4-aminophenoxy)isoindoline-1,3-dione to afford the urea.

Entry 7: 4-(1-Oxoisoindolin-5-yloxy)aniline was synthesized according to Method A12. According to Method 2d, 5-tert-butyl-2-methoxyaniline was reacted with CDI followed by 4-(1-oxoisoindolin-5-yloxy)aniline to afford the urea.

Entry 8: 4-(3-N-Methylcarbamoylphenoxy)aniline was synthesized according to Method A13. According to Method C2a, 2-methoxy-5-(trifluoromethyl)aniline was reacted with CDI followed by 4-(3-N-methylcarbamoylphenoxy)aniline to afford the urea.

Entry 9: 4-Hydroxyacetophenone was reacted with 2-chloro-5-nitropyridine to give 4-(4-acetylphenoxy)-5-nitropyridine according to Method A3, Step 2. According to Method A8, Step 4, 4-(4-acetylphenoxy)-5-nitropyridine was reduced to 4-(4-acetylphenoxy)-5-aminopyridine. 2-Methoxy-5-(trifluoromethyl)aniline was converted to 2-methoxy-5-(trifluoromethyl)phenyl isocyanate according to Method B1. The isocyanate was reacted with 4-(4-acetylphenoxy)-5-aminopyridine according to Method C1a to afford the urea.

Entry 10: 4-Fluoro-1-nitrobenzene and p-hydroxyacetophenone were reacted according to Method A13, Step 1 to afford the 4-(4-acetylphenoxy)-1-nitrobenzene. 4-(4-Acetylphenoxy)-1-nitrobenzene was reduced according to Method A13, Step 4 to afford 4-(4-acetylphenoxy)aniline. According to Method C3, 5-(trifluoromethyl)-2-methoxybutylaniline was reacted with bis(trichloromethyl) carbonate followed by 4-(4-acetylphenoxy)aniline to afford the urea.

Entry 11: 4-Chloro-N-methyl-2-pyridinecarboxamide, which was synthesized according to Method A2, Step 3a, was reacted with 3-aminophenol according to Method A2, Step 4 using DMAC in place of DMF to give 3-(-2-(N-methylcarbamoyl)-4-pyridyloxy)aniline. According to Method C4, 2-methoxy-5-(trifluoromethyl)aniline was reacted with phosgene followed by 3-(-2-(N-methylcarbamoyl)-4-pyridyloxy) aniline to afford the urea.

Entry 12: 4-Chloropyridine-2-carbonyl chloride HCl salt was reacted with ammonia according to Method A2, Step 3b to form 4-chloro-2-pyridinecarboxamide. 4-Chloro-2-pyridinecarboxamide was reacted with 3-aminophenol according to Method A2, Step 4 using DMAC in place of DMF to give 3-(2-carbamoyl-4-pyridyloxy)aniline. According to Method C2a, 2-methoxy-5-(trifluoromethyl)aniline was reacted with phosgene followed by 3-(2-carbamoyl-4-pyridyloxy)aniline afford the urea.

Entry 13: 4-Chloro-N-methyl-2-pyridinecarboxamide was synthesized according to Method A2, Step 3b. 4-Chloro-N-methyl-2-pyridinecarboxamide was reacted with 4-aminophenol according to Method A2, Step 4 using DMAC in place of DMF to give 4-(2-(N-methylcarbamoyl)-4-pyridyloxy)aniline. According to Method C2a, 2-methoxy-5-(trifluoromethyl)aniline was reacted with CDI followed by 4-(2-(N-methylcarbamoyl)-4-pyridyloxy)aniline to afford the urea.

Entry 14: 4-Chloropyridine-2-carbonyl chloride HCl salt was reacted with ammonia according to Method A2, Step 3b to form 4-chloro-2-pyridinecarboxamide. 4-Chloro-2-pyridinecarboxamide was reacted with 4-aminophenol according to Method A2, Step 4 using DMAC in place of DMF to give 4-(2-carbamoyl-4-pyridyloxy)aniline. According to Method C4, 2-methoxy-5-(trifluoromethyl)aniline was reacted with phosgene followed by 4-(2-carbamoyl-4-pyridyloxy)aniline afford the urea.

Entry 15: According to Method C2d, 5-(trifluoromethyl)-2-methoxyaniline was reacted with CDI followed by 4-(3-N-methylcarbamoyl)-4-methoxyphenoxy)aniline, which had been prepared according to Method A8, to afford the urea.

Entry 16: 4-(2-(N-Methylcarbamoyl)-4-pyridyloxy)-2-methylaniline was synthesized according to Method A5. 5-(Trifluoromethyl)-2-methoxyaniline was converted into 5-(trifluoromethyl)-2-methoxyphenyl isocyanate according to Method B1. The isocyanate was reacted with 4-(2-(N-methylcarbamoyl)-4-pyridyloxy)-2-methylaniline according to Method C1c to afford the urea.

Entry 17: 4-(2-(N-Methylcarbamoyl)-4-pyridyloxy)-2-chloroaniline was synthesized according to Method A6. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(2-(N-methylcarbamoyl)-4-pyridyloxy)-2-chloroaniline according to Method C1a to afford the urea.

Entry 18: According to Method A2, Step 4, 5-amino-2-methylphenol was reacted with 4-chloro-N-methyl-2-pyridinecarboxamide, which had been synthesized according to Method A2, Step 3b, to give 3-(2-(N-methylcarbamoyl)-4-pyridyloxy)-4-methylaniline. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 3-(2-(N-methylcarbamoyl)-4-pyridyloxy)-4-methylaniline according to Method C1a to afford the urea.

Entry 19: 4-Chloropyridine-2-carbonyl chloride was reacted with ethylamine according to Method A2, Step 3b. The resulting 4-chloro-N-ethyl-2-pyridinecarboxamide was reacted with 4-aminophenol according to Method A2, Step 4 to give 4-(2-(N-ethylcarbamoyl)-4-pyridyloxy)aniline. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(2-(N-ethylcarbamoyl)-4-pyridyloxy)aniline according to Method C1a to afford the urea.

Entry 20: According to Method A2, Step 4, 4-amino-2-chlorophenol was reacted with 4-chloro-N-methyl-2-pyridinecarboxamide, which had been synthesized according to Method A2, Step 3b, to give 4-(2-(N-methylcarbamoyl)-4-pyridyloxy)-3-chloroaniline. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(2-(N-methylcarbamoyl)-4-pyridyloxy)-3-chloroaniline. according to Method C1a to afford the urea.

Entry 21: 4-(4-Methylthiophenoxy)-1-nitrobenzene was oxidized according to Method A19, Step 1 to give 4-(4-methylsulfonylphenoxy)-1-nitrobenzene. The nitrobenzene was reduced according to Method A19, Step 2 to give 4-(4-methylsulfonylphenoxy)-1-aniline. According to Method C1a, 5-(trifluoromethyl)-2-methoxyphenyl isocyanate was reacted with 4-(4-methylsulfonylphenoxy)-1-aniline to afford the urea.

Entry 22: 4-(3-Carbamoylphenoxy)-1-nitrobenzene was reduced to 4-(3-carbamoylphenoxy)aniline according to Method A15, Step 4. According to Method C1a, 5-(trifluoromethyl)-2-methoxyphenyl isocyanate was reacted with 4-(3-carbamoylphenoxy)aniline to afford the urea.

Entry 23: 5-(4-Aminophenoxy)isoindoline-1,3-dione was synthesized according to Method A3. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 5-(4-aminophenoxy)isoindoline-1,3-dione according to Method C1a to afford the urea.

Entry 24: 4-Chloropyridine-2-carbonyl chloride was reacted with dimethylamine according to Method A2, Step 3b. The resulting 4-chloro-N,N-dimethyl-2-pyridinecarboxamide was reacted with 4-aminophenol according to Method A2, Step 4 to give 4-(2-(N,N-dimethylcarbamoyl)-4-pyridyloxy)aniline. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(2-(N,N-dimethylcarbamoyl)-4-pyridyloxy)aniline according to Method C1a to afford the urea.

Entry 25: 4-(1-Oxoisoindolin-5-yloxy)aniline was synthesized according to Method A12. 5-(Trifluoromethyl)-2-methoxyaniline was treated with CDI, followed by 4-(1-oxoisoindolin-5-yloxy) aniline according to Method C2d to afford the urea.

Entry 26: 4-Hydroxyacetophenone was reacted with 4-fluoronitrobenzene according to Method A13, Step 1 to give 4-(4-acetylphenoxy)nitrobenzene. The nitrobenzene was reduced according to Method 13, Step 4 to afford 4-(4- acetylphenoxy)aniline, which was converted to the 4-(4-(1-(N-methoxy)iminoethyl)phenoxyaniline HCl salt according to Method A16. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(4-(1-(N-methoxy)iminoethyl)phenoxyaniline HCl salt to Method C1a to afford the urea.

Entry 27: 4-Chloro-N-methylpyridinecarboxamide was synthesized as described in Method A2, Step 3b. The chloropyridine was reacted with 4-aminothiophenol according to Method A2, Step 4 to give 4-(4-(2-(N-methylcarbamoyl)phenylthio)aniline. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(4-(2-(N-methylcarbamoyl)phenylthio)aniline according to Method C1a to afford the urea.

Entry 28: 5-(4-Aminophenoxy)-2-methylisoindoline-1,3-dione was synthesized according to Method A9. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 5-(4-aminophenoxy)-2-methylisoindoline-1,3-dione according to Method C1a to afford the urea.

Entry 29: 4-Chloro-N-methylpyridinecarboxamide was synthesized as described in Method A2, Step 3b. The chloropyridine was reacted with 3-aminothiophenol according to Method A2, Step 4 to give 3-(4-(2-(N-methylcarbamoyl)phenylthio)aniline. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 3-(4-(2-(N-methylcarbamoyl)phenylthio)aniline according to Method C1a to afford the urea.

Entry 30: 4-Chloropyridine-2-carbonyl chloride was reacted with isopropylamine according to Method A2, Step 3b. The resulting 4-chloro-N-isopropyl-2-pyridinecarboxamide was reacted with 4-aminophenol according to Method A2, Step 4 to give 4-(2-(N-isopropylcarbamoyl)-4-pyridyloxy) aniline. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(2-(N-isopropylcarbamoyl)-4-pyridyloxy)aniline according to Method C1a to afford the urea.

Entry 31: 4-(3-(5-Methoxycarbonyl)pyridyloxy)aniline was synthesized according to Method A14. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(3-(5-methoxycarbonyl)pyridyloxy)aniline according to Method C1a to afford the urea. N-(5-(Trifluoromethyl)-2-methoxyphenyl)-N'-(4-(3-(5-methoxycarbonylpyridyl) oxy)phenyl) urea was saponified according to Method D4, Step 1, and the corresponding acid was coupled with 4-(2-aminoethyl)morpholine to afford the amide according to Method D4, Step 2.

Entry 32: 4-(3-(5-Methoxycarbonyl)pyridyloxy)aniline was synthesized according to Method A14. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(3-(5-methoxycarbonyl)pyridyloxy)aniline according to Method C1a to afford the urea. N-(5-(Trifluoromethyl)-2-methoxyphenyl)-N'-(4-(3-(5-methoxycarbonylpyridyl) oxy)phenyl) urea was saponified according to Method D4, Step 1, and the corresponding acid was coupled with methylamine according to Method D4, Step 2 to afford the amide.

Entry 33: 4-(3-(5-Methoxycarbonyl)pyridyloxy)aniline was synthesized according to Method A14. 5-(Trifluoromethyl)-2-methoxyaniline was converted into 5-(trifluoromethyl)-2-methoxyphenyl isocyanate according to Method B1. 5-(Trifluoromethyl)-2-methoxyphenyl isocyanate was reacted with 4-(3-(5-methoxycarbonyl)pyridyloxy)aniline according to Method C1a to afford the urea. N-(5-(Trifluoromethyl)-2-methoxyphenyl)-N'-(4-(3-(5-methoxycarbonylpyridyl) oxy)phenyl) urea was saponified according to Method D4, Step 1, and the corresponding acid was coupled with N,N-dimethylethylenediamine according to Method D4, Step 2 to afford the amide.

Entry 34: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N'-(3-carboxyphenyl) urea, which was coupled with 3-aminopyridine according to Method D1c.

Entry 35: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N'-(3-carboxyphenyl) urea, which was coupled with N-(4-fluorophenyl) piperazine according to Method D1c.

Entry 36: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N'-(3-carboxyphenyl) urea, which was coupled with 4-fluoroaniline according to Method D1c.

Entry 37: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N'-(3-carboxyphenyl) urea, which was coupled with 4-(dimethylamino) aniline according to Method D1c.

Entry 38: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N'-(3-carboxyphenyl) urea, which was coupled with 5-amino-2-methoxypyridine according to Method D1c.

Entry 39: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N'-(3-carboxyphenyl) urea, which was coupled with 4-morpholinoaniline according to Method D1c.

Entry 40: 4-(3-Carboxyphenoxy)aniline was synthesized according to Method A11. 5-(Trifluoromethyl)-2-methoxyaniline was converted into 5-(trifluoromethyl)-2-methoxyphenyl isocyanate according to Method B1. 4-(3-Carboxyphenoxy)aniline was reacted with 5-(trifluoromethyl)-2-methoxyphenyl isocyanate according to Method C1f to afford N-(5-(trifluoromethyl)-2-methoxyphenyl)-N'-(3-carboxyphenyl) urea, which was coupled with N-(2-pyridyl)piperazine according to Method D1c.

Entry 41: 4-(3-(N-Methylcarbamoyl)phenoxy)aniline was synthesized according to Method A13. According to Method C3, 4-chloro-3-(trifluoromethyl)aniline was converted to the isocyanate, then reacted with 4-(3-(N-Methylcarbamoyl) phenoxy)aniline to afford the urea.

Entry 42: 4-(2-N-Methylcarbamyl-4-pyridyloxy)aniline was synthesized according to Method A2. 4-Chloro-3-(trifluoromethyl)phenyl isocyanate was reacted with 4-(2-N-methylcarbamyl-4-pyridyloxy)aniline according to Method C1a to afford the urea.

Entry 43: 4-Chloropyridine-2-carbonyl chloride HCl salt was reacted with ammonia according to Method A2, Step 3b to form 4-chloro-2-pyridinecarboxamide. 4-Chloro-2-pyridinecarboxamide was reacted with 4-aminophenol according to Method A2, Step 4 to form 4-(2-carbamoyl-4-pyridyloxy) aniline. According to Method C1a, 4-chloro-3-(trifluoromethyl)phenyl isocyanate was reacted with 4-(2-carbamoyl-4-pyridyloxy)aniline to afford the urea.

Entry 44: 4-Chloropyridine-2-carbonyl chloride HCl salt was reacted with ammonia according to Method A2, Step 3b to form 4-chloro-2-pyridinecarboxamide. 4-Chloro-2-pyridinecarboxamide was reacted with 3-aminophenol according to Method A2, Step 4 to form 3-(2-carbamoyl-4-pyridyloxy) aniline. According to Method C1a, 4-chloro-3-(trifluoromethyl)phenyl isocyanate was reacted with 3-(2-carbamoyl-4-pyridyloxy)aniline. afford the urea.

Entry 45: 4-Chloro-N-methyl-2-pyridinecarboxamide, which was synthesized according to Method A2, Step 3a, was reacted with 3-aminophenol according to Method A2, Step 4 to form 3-(-2-(N-methylcarbamoyl)-4-pyridyloxy)aniline. According to Method C1a, 4-chloro-3-(trifluoromethyl)phenyl isocyanate was reacted with 3-(2-(N-methylcarbamoyl)-4-pyridyloxy)aniline to afford the urea.

Entry 46: 5-(4-Aminophenoxy)isoindoline-1,3-dione was synthesized according to Method A3. According to Method C1a, 4-chloro-3-(trifluoromethyl)phenyl isocyanate was reacted with 5-(4-aminophenoxy)isoindoline-1,3-dione to afford the urea.

Entry 47: 4-(2-(N-Methylcarbamoyl)-4-pyridyloxy)-2-methylaniline was synthesized according to Method A5. According to Method C1c, 4-chloro-3-(trifluoromethyl)phenyl isocyanate was reacted with 5-(4-aminophenoxy)isoindoline-1,3-dione to afford the urea.

Entry 48: 4-(3-N-Methylsulfamoyl)phenyloxy)aniline was synthesized according to Method A15. According to Method C1a, 4-chloro-3-(trifluoromethyl)phenyl isocyanate was reacted with 4-(3-N-methylsulfamoyl)phenyloxy) aniline to afford the urea.

Entry 49: 4-(2-(N-Methylcarbamoyl)-4-pyridyloxy)-2-chloroaniline was synthesized according to Method A6. According to Method C1a, 4-chloro-3-(trifluoromethyl)phenyl isocyanate was reacted with 4-(2-(N-methylcarbamoyl)-4-pyridyloxy)-2-chloroaniline to afford the urea.

Entry 50: According to Method A2, Step 4, 5-amino-2-methylphenol was reacted with 4-chloro-N-methyl-2-pyridinecarboxamide, which had been synthesized according to Method A2, Step 3b, to give 3-(2-(N-methylcarbamoyl)-4-pyridyloxy)-4-methylaniline. According to Method C1a, 4-chloro-3-(trifluoromethyl)phenyl isocyanate was reacted with 3-(2-(N-methylcarbamoyl)-4-pyridyloxy)-4-methylaniline to afford the urea.

Entry 51: 4-Chloropyridine-2-carbonyl chloride was reacted with ethylamine according to Method A2, Step 3b. The resulting 4-chloro-N-ethyl-2-pyridinecarboxamide was reacted with 4-aminophenol according to Method A2, Step 4 to give 4-(2-(N-ethylcarbamoyl)-4-pyridyloxy)aniline. According to Method C1a, 4-chloro-3-(trifluoromethyl)phenyl isocyanate was reacted with 4-(2-(N-ethylcarbamoyl)-4-pyridyloxy)aniline to afford the urea.

Entry 52: According to Method A2, Step 4, 4-amino-2-chlorophenol was reacted with 4-chloro-N-methyl-2-pyridinecarboxamide, which had been synthesized according to Method A2, Step 3b, to give 4-(2-(N-methylcarbamoyl)-4-pyridyloxy)-3-chloroaniline. According to Method C1a, 4-chloro-3-(trifluoromethyl)phenyl isocyanate was reacted with 4-(2-(N-methylcarbamoyl)-4-pyridyloxy)-3-chloroaniline to afford the urea.

Entry 53: 4-(4-Methylthiophenoxy)-1-nitrobenzene was oxidized according to Method A19, Step 1 to give 4-(4-methylsulfonylphenoxy)-1-nitrobenzene. The nitrobenzene was reduced according to Method A18, Step 2 to give 4-(4-methylsulfonylphenoxy)-1-aniline. According to Method C1a, 4-chloro-3-(trifluoromethyl)phenyl isocyanate was reacted with 4-(4-methylsulfonylphenoxy)-1-aniline afford the urea.

Entry 54: 4-Bromobenzenesulfonyl chloride was reacted with methylamine according to Method A15, Step 1 to afford N-methyl-4-bromobenzenesulfonamide. N-Methyl-4-bromobenzenesulfonamide was coupled with phenol according to Method 15, Step 2 to afford 4-(4-(N-methylsulfamoyl) phenoxy)benzene. 4-(4-(N-Methylsulfamoyl)phenoxy)benzene was converted into 4-(4-(N-methylsulfamoyl)phenoxy)-1-nitrobenzene according to Method A15, Step 3. 4-(4-(N-Methylsulfamoyl)phenoxy)-1-nitrobenzene was reduced to 4-(4-N-methylsulfamoyl)phenyloxy)aniline according to Method A15, Step 4. According to Method C1a, 4-chloro-3-(trifluoromethyl)phenyl isocyanate was reacted with 4-(3-N-methylsulfamoyl)phenyloxy)aniline to afford the urea.

Entry 55: 5-Hydroxy-2-methylpyridine was coupled with 1-fluoro-4-nitrobenzene according to Method A18, Step 1 to give 4-(5-(2-methyl)pyridyloxy)-1-nitrobenzene. The methylpyridine was oxidized the carboxylic acid, then esterified according to Method A18, Step 2 to give 4-(5-(2-methoxycarbonyl)pyridyloxy)-1-nitrobenzene. The nitrobenzene was reduced according the Method A18, Step 3 to give 4-(5-(2-methoxycarbonyl) pyridyloxy)aniline. The aniline was reacted with 4-chloro-3-(trifluoromethyl)phenyl isocyanate according to Method C1a to afford the urea.

Entry 56: 5-Hydroxy-2-methylpyridine was coupled with 1-fluoro-4-nitrobenzene according to Method A18, Step 1 to give 4-(5-(2-methyl)pyridyloxy)-1-nitrobenzene. The methylpyridine was oxidized the carboxylic acid, then esterified according to Method A18, Step 2 to give 4-(5-(2-methoxycarbonyl)pyridyloxy)-1-nitrobenzene. The nitrobenzene was reduced according the Method A18, Step 3 to give 4-(5-(2-methoxycarbonyl) pyridyloxy)aniline. The aniline was reacted with 4-chloro-3-(trifluoromethyl)phenyl isocyanate according to Method C1a to give N-(4-chloro-3-(trifluoromethyl) phenyl)-N'-(4-(2-(methoxycarbonyl)-5-pyridyloxy) phenyl) urea. The methyl ester was reacted with methylamine according to Method D2 to afford N-(4-chloro-3-(trifluoromethyl) phenyl)-N'-(4-(2-(N-methylcarbamoyl)-5-pyridyloxy) phenyl) urea.

Entry 57: N-(4-Chloro-3-(trifluoromethyl)phenyl-N'-(4-aminophenyl) urea was prepared according to Method C1d. N-(4-Chloro-3-(trifluoromethyl)phenyl-N'-(4-aminophenyl) urea was coupled with mono-methyl isophthalate according to Method D1a to afford the urea.

Entry 58: N-(4-Chloro-3-(trifluoromethyl)phenyl-N'-(4-aminophenyl) urea was prepared according to Method C1d. N-(4-Chloro-3-(trifluoromethyl)phenyl-N'-(4-aminophenyl) urea was coupled with mono-methyl isophthalate according to Method D1a to afford N-(4-chloro-3-(trifluoromethyl)phenyl-N'-(4-(3-methoxycarbonylphenyl)carboxyaminophenyl) urea. According to Method D2, N-(4-chloro-3-(trifluoromethyl)phenyl-N'-(4-(3-methoxycarbonylphenyl) carboxyaminophenyl) urea was reacted with methylamine to afford the corresponding methyl amide.

Entry 59: 4-Chloropyridine-2-carbonyl chloride was reacted with dimethylamine according to Method A2, Step 3b. The resulting 4-chloro-N,N-dimethyl-2-pyridinecarboxamide was reacted with 4-aminophenol according to Method A2, Step 4 to give 4-(2-(N,N-dimethylcarbamoyl)-4-pyridyloxy)aniline. According to Method C1a, 4-chloro-3-(trifluoromethyl)phenyl isocyanate was reacted with 4-(2-(N,N-dimethylcarbamoyl)-4-pyridyloxy)aniline to afford the urea.

Entry 60: 4-Hydroxyacetophenone was reacted with 4-fluoronitrobenzene according to Method A13, Step 1 to give 4-(4-acetylphenoxy)nitrobenzene. The nitrobenzene was reduced according to Method 13, Step 4 to afford 4-(4-acetylphenoxy)aniline, which was converted to the 4-(4-(1-(N-methoxy)iminoethyl)phenoxyaniline HCl salt according to Method A16. According to Method C1a, 4-chloro-3-(trifluoromethyl)phenyl isocyanate was reacted with 4-(4-acetylphenoxy)aniline afford the urea.

Entry 61: 4-(3-Carboxyphenoxy)-1-nitrobenzene was synthesized according to Method A13, Step 2. 4-(3-Carboxyphenoxy)-1-nitrobenzene was coupled with 4-(2-aminoethyl) morpholine according to Method A13, Step 3 to give 4-(3-(N-(2-morpholinylethyl) carbamoyl)phenoxy)-1-nitrobenzene. According to Method A13 Step 4, 4-(3-(N-(2-morpholinylethyl)carbamoyl)phenoxy)-1-nitrobenzene was reduced to 4-(3-(N-(2-morpholinylethyl) carbamoyl)phenoxy)aniline. According to Method C1a, 4-chloro-3-(trifluoromethyl)phenyl isocyanate was reacted with 4-(3-(N-(2-morpholinylethyl) carbamoyl)phenoxy)aniline to afford the urea.

Entry 62: 4-(3-Carboxyphenoxy)-1-nitrobenzene was synthesized according to Method A13, Step 2. 4-(3-Carboxyphenoxy)-1-nitrobenzene was coupled with 1-(2-aminoethyl)piperidine according to Method A13, Step 3 to give 4-(3-(N-(2-piperidylethyl)carbamoyl)phenoxy)-1-nitrobenzene. According to Method A13 Step 4, 4-(3-(N-(2-piperidylethyl) carbamoyl)phenoxy)-1-nitrobenzene was reduced to 4-(3-(N-(2-piperidylethyl) carbamoyl)phenoxy)aniline. According to Method C1a, 4-chloro-3-(trifluoromethyl)phenyl isocyanate was reacted with 4-(3-(N-(2-piperidylethyl) carbamoyl)phenoxy)aniline to afford the urea.

Entry 63: 4-(3-Carboxyphenoxy)-1-nitrobenzene was synthesized according to Method A13, Step 2. 4-(3-Carboxyphenoxy)-1-nitrobenzene was coupled with tetrahydrofurfurylamine according to Method A13, Step 3 to give 4-(3-(N-(tetrahydrofurylmethyl) carbamoyl)phenoxy)-1-nitrobenzene. According to Method A13 Step 4, 4-(3-(N-(tetrahydrofurylmethyl)carbamoyl)phenoxy)-1-nitrobenzene was reduced to 4-(3-(N-(tetrahydrofurylmethyl) carbamoyl)phenoxy)aniline. According to Method C1a, 4-chloro-3-(trifluoromethyl)phenyl isocyanate was reacted with 4-(3-(N-(tetrahydrofurylmethyl) carbamoyl)phenoxy) aniline to afford the urea.

Entry 64: 4-(3-Carboxyphenoxy)-1-nitrobenzene was synthesized according to Method A13, Step 2. 4-(3-Carboxyphenoxy)-1-nitrobenzene was coupled with 2-aminomethyl-1-ethylpyrrolidine according to Method A13, Step 3 to give 4-(3-(N-((1-methylpyrrolidinyl) methyl)carbamoyl)phenoxy)-1-nitrobenzene. According to Method A13 Step 4, 4-(3-(N-((1-methylpyrrolidinyl)methyl)carbamoyl)phenoxy)-1-nitrobenzene was reduced to 4-(3-(N-((1-methylpyrrolidinyl)methyl)carbamoyl)phenoxy)aniline. According to Method C1a, 4-chloro-3-(trifluoromethyl)phenyl isocyanate was reacted with 4-(3-(N-((1-methylpyrrolidinyl) methyl)carbamoyl)phenoxy)aniline to afford the urea.

Entry 65: 4-Chloro-N-methylpyridinecarboxamide was synthesized as described in Method A2, Step 3b. The chloropyridine was reacted with 4-aminothiophenol according to Method A2, Step 4 to give 4-(4-(2-(N-methylcarbamoyl)phenylthio)aniline. According to Method C1a, 4-chloro-3-(trifluoromethyl)phenyl isocyanate was reacted with 4-(4-(2-(N-methylcarbamoyl) phenylthio)aniline to afford the urea.

Entry 66: 4-Chloropyridine-2-carbonyl chloride was reacted with isopropylamine according to Method A2, Step 3b. The resulting 4-chloro-N-isopropyl-2-pyridinecarboxamide was reacted with 4-aminophenol according to Method A2, Step 4 to give 4-(2-(N-isopropylcarbamoyl)-4-pyridyloxy) aniline. According to Method C1a, 4-chloro-3-(trifluoromethyl)phenyl isocyanate was reacted with 4-(2-(N-isopropylcarbamoyl)-4-pyridyloxy)aniline to afford the urea.

Entry 67: N-(4-Chloro-3-(trifluoromethyl)phenyl-N'-(4-ethoxycarbonylphenyl) urea was synthesized according to Method C1e. N-(4-Chloro-3-(trifluoromethyl)phenyl-N'-(4-ethoxycarbonylphenyl) urea was saponified according to Method D3 to give N-(4-chloro-3-(trifluoromethyl)phenyl-N'-(4-carboxyphenyl) urea. N-(4-Chloro-3-(trifluoromethyl) phenyl-N'-(4-carboxyphenyl) urea was coupled with 3-methylcarbamoylaniline according to Method D1b to give N-(4-chloro-3-(trifluoromethyl)phenyl-N'-(4-(3-methylcarbamoylphenyl) carbamoylphenyl) urea.

Entry 68: 5-(4-Aminophenoxy)-2-methylisoindoline-1,3-dione was synthesized according to Method A9. According to Method C1a, 4-chloro-3-(trifluoromethyl)phenyl isocyanate was reacted with 5-(4-aminophenoxy)-2-methylisoindoline-1,3-dione to afford the urea.

Entry 69: 4-Chloro-N-methylpyridinecarboxamide was synthesized as described in Method A2, Step 3b. The chloropyridine was reacted with 3-aminothiophenol according to Method A2, Step 4 to give 3-(4-(2-(N-methylcarbamoyl)phenylthio)aniline. According to Method C1a, 4-chloro-3-(trifluoromethyl)phenyl isocyanate was reacted with 3-(4-(2-(N-methylcarbamoyl) phenylthio)aniline to afford the urea.

Entry 70: 4-(2-(N-(2-Morpholin-4-ylethyl)carbamoyl)pyridyloxy)aniline was synthesized according to Method A10. According to Method C1a, 4-chloro-3-(trifluoromethyl)phenyl isocyanate was reacted with 4-(2-(N-(2-morpholin-4-ylethyl)carbamoyl)pyridyloxy)aniline to afford the urea.

Entry 71: 4-(3-(5-Methoxycarbonyl)pyridyloxy)aniline was synthesized according to Method A14. 4-Chloro-3-(trifluoromethyl)-2-methoxyphenyl isocyanate was reacted with 4-(3-(5-methoxycarbonyl)pyridyloxy)aniline according to Method C1a to afford the urea. N-(4-Chloro-3-(trifluoromethyl)phenyl)-N'-(4-(3-(5-methoxycarbonylpyridyl)oxy) phenyl)urea was saponified according to Method D4, Step 1, and the corresponding acid was coupled with 4-(2-aminoethyl)morpholine to afford the amide.

Entry 72: 4-(3-(5-Methoxycarbonyl)pyridyloxy)aniline was synthesized according to Method A14. 4-Chloro-3-(trifluoromethyl)phenyl isocyanate was reacted with 4-(3-(5-methoxycarbonyl) pyridyloxy)aniline according to Method C1a to afford the urea. N-(5-(Trifluoromethyl)-2-methoxyphenyl)-N'-(4-(3-(5-methoxycarbonylpyridyl)oxy)phenyl) urea was saponified according to Method D4, Step 1, and the corresponding acid was coupled with methylamine according to Method D4, Step 2 to afford the amide.

Entry 73: 4-(3-(5-Methoxycarbonyl)pyridyloxy)aniline was synthesized according to Method A14. 4-Chloro-3-(trifluoromethyl)phenyl isocyanate was reacted with 4-(3-(5-methoxycarbonyl) pyridyloxy)aniline according to Method C1a to afford the urea. N-(5-(Trifluoromethyl)-2-methoxyphenyl)-N'-(4-(3-(5-methoxyaarbonylpyridyl)oxy)phenyl) urea was saponified according to Method D4, Step 1, and the corresponding acid was coupled with N,N-dimethylethylenediamine according to Method D4, Step 2 to afford the amide.

Entry 74: 4-Chloropyridine-2-carbonyl chloride HCl salt was reacted with 2-hydroxyethylamine according to Method A2, Step 3b to form 4-chloro-N-(2-triisopropylsilyloxy) ethylpyridine-2-carboxamide. 4-Chloro-N-(2-triisopropylsilyloxy) ethylpyridine-2-carboxamide was reacted with triisopropylsilyl chloride, followed by 4-aminophenol according to Method A17 to form 4-(4-(2-(N-(2-Triisopropylsilyloxy) ethylcarbamoyl)pyridyloxyaniline. According to Method C1a, 4-chloro-3-(trifluoromethyl)phenyl isocyanate was reacted with 4-(4-(2-(N-(2-Triisopropylsilyloxy) ethylcarbamoyl)pyridyloxyaniline to afford N-(4-chloro-3-((trifluoromethyl)phenyl)-N'-(4-(4-(2-(N-(2-triisopropylsilyloxy) ethylcarbamoyl)pyridyloxyphenyl) urea.

Entry 75: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with 3-aminopyridine according to Method D 1 c.

Entry 76: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with N-(4-acetylphenyl)piperazine according to Method D1c.

Entry 77: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with 4-fluoroaniline according to Method D1c.

Entry 78: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with 4-(dimethylamino)aniline according to Method D1c.

Entry 79: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with N-phenylethylenediamine according to Method D1c.

Entry 80: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with 2-methoxyethylamine according to Method D1c.

Entry 81: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with 5-amino-2-methoxypyridine according to Method D1c.

Entry 82: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with 4-morpholinoaniline according to Method D1c.

Entry 83: 4-(3-Carboxyphenoxy)aniline was synthesized according to Method A11. 4-Chloro-3-(trifluoromethyl)phenyl isocyanate was reacted with 4-(3-carboxyphenoxy) aniline according to Method C1f to afford the urea, which was coupled with N-(2-pyridyl)piperazine according to Method D1c.

Entry 84: 4-Chloropyridine-2-carbonyl chloride HCl salt was reacted with 2-hydroxyethylamine according to Method A2, Step 3b to form 4-chloro-N-(2-triisopropylsilyloxy)ethylpyridine-2-carboxamide. 4-Chloro-N-(2-triisopropylsilyloxy) ethylpyridine-2-carboxamide was reacted with triisopropylsilyl chloride, followed by 4-aminophenol according to Method A17 to form 4-(4-(2-(N-(2-Triisopropylsilyloxy) ethylcarbamoyl)pyridyloxyaniline. According to Method C1a, 4-chloro-3-(trifluoromethyl)phenyl isocyanate was reacted with 4-(4-(2-(N-(2-Triisopropylsilyloxy) ethylcarbamoyl)pyridyloxyaniline to give N-(4-chloro-3-((trifluoromethyl)phenyl)-N'-(4-(4-(2-(N-(2-triisopropylsilyloxy) ethylcarbamoyl)pyridyloxyphenyl) urea. The urea was deprotected according to Method D5 to afford N-(4-chloro-3-((trifluoromethyl)phenyl)-N'-(4-(4-(2-(N-(2-hydroxy) ethylcarbamoyl)pyridyloxyphenyl) urea.

Entry 85: 4-(2-(N-Methylcarbamoyl)-4-pyridyloxy) aniline was synthesized according to Method A2. 4-Bromo-3-(trifluoromethyl)aniline was converted to 4-bromo-3-(trifluoromethyl)phenyl isocyanate according to Method B1. According to Method C1a, 4-bromo-3-(trifluoromethyl)phenyl isocyanate was reacted with 4-(2-(N-methylcarbamoyl)-4-pyridyloxy)aniline to afford the urea.

Entry 86: 4-(2-(N-Methylcarbamoyl)-4-pyridyloxy)-2-chloroaniline was synthesized according to Method A6. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 4-(2-(N-methylcarbamoyl)-4-pyridyloxy)-2-chloroaniline to afford the urea.

Entry 87: According to Method A2, Step 4, 4-amino-2-chlorophenol was reacted with 4-chloro-N-methyl-2-pyridinecarboxamide, which had been synthesized according to Method A2, Step 3b, to give 4-(2-(N-methylcarbamoyl)-4-pyridyloxy)-3-chloroaniline. 4-Bromo-3-(trifluoromethyl) aniline was converted into 4-bromo-3-(trifluoromethyl)phenyl isocyanate according to Method B1. According to Method C1a, 4-bromo-3-(trifluoromethyl)phenyl isocyanate was reacted with 4-(2-(N-methylcarbamoyl)-4-pyridyloxy)-3-chloroaniline to afford the urea.

Entry 88: 4-Chloropyridine-2-carbonyl chloride was reacted with ethylamine according to Method A2, Step 3b. The resulting 4-chloro-N-ethyl-2-pyridinecarboxamide was reacted with 4-aminophenol according to Method A2, Step 4 to give 4-(2-(N-ethylcarbamoyl)-4-pyridyloxy)aniline. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 4-(2-(N-ethylcarbamoyl)-4-pyridyloxy)aniline to afford the urea.

Entry 89: 4-Chloro-N-methyl-2-pyridinecarboxamide, which was synthesized according to Method A2, Step 3a, was reacted with 3-aminophenol according to Method A2, Step 4 to form 3-(-2-(N-methylcarbamoyl)-4-pyridyloxy)aniline. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 3-(-2-(N-methylcarbamoyl)-4-pyridyloxy)aniline to afford the urea.

Entry 90: According to Method A2, Step 4, 5-amino-2-methylphenol was reacted with 4-chloro-N-methyl-2-pyridinecarboxamide, which had been synthesized according to Method A2, Step 3b, to give 3-(2-(N-methylcarbamoyl)-4-pyridyloxy)-4-methylaniline. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 3-(2-(N-methylcarbamoyl)-4-pyridyloxy)-4-methylaniline to afford the urea.

Entry 91: 4-Chloropyridine-2-carbonyl chloride was reacted with dimethylamine according to Method A2, Step 3b. The resulting 4-chloro-N,N-dimethyl-2-pyridinecarboxamide was reacted with 4-aminophenol according to Method A2, Step 4 to give 4-(2-(N,N-dimethylcarbamoyl)-4-pyridyloxy)aniline. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 4-(2-(N,N-dimethylcarbamoyl)-4-pyridyloxy)aniline to afford the urea.

Entry 92: 4-Chloro-N-methylpyridinecarboxamide was synthesized as described in Method A2, Step 3b. The chloropyridine was reacted with 4-aminothiophenol according to Method A2, Step 4 to give 4-(4-(2-(N-methylcarbamoyl)phenylthio)aniline. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 4-(4-(2-(N-methylcarbamoyl)phenylthio)aniline to afford the urea.

Entry 93: 4-Chloro-N-methylpyridinecarboxamide was synthesized as described in Method A2, Step 3b. The chloropyridine was reacted with 3-aminothiophenol according to Method A2, Step 4 to give 3-(4-(2-(N-methylcarbamoyl)phenylthio)aniline. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 3-(4-(2-(N-methylcarbamoyl)phenylthio)aniline to afford the urea.

Entry 94: 4-(2-(N-(2-Morpholin-4-ylethyl)carbamoyl)pyridyloxy)aniline was synthesized according to Method A10. 4-Bromo-3-(trifluoromethyl)aniline was converted into 4-bromo-3-(trifluoromethyl)phenyl isocyanate according to Method B1. According to Method C1a, 4-bromo-3-(trifluoromethyl)phenyl isocyanate was reacted with 4-(2-(N-(2-Morpholin-4-ylethyl) carbamoyl)pyridyloxy)aniline to afford the urea.

Entry 95: 4-(2-(N-Methylcarbamoyl)-4-pyridyloxy)aniline was synthesized according to Method A2. 4-Chloro-2-methoxy-5-(trifluoromethyl)aniline was synthesized according to Method A7. 4-Chloro-2-methoxy-5-(trifluoromethyl)aniline was converted into 4-chloro-2-methoxy-5-(trifluoromethyl)phenyl isocyanate according to Method B1. According to Method C1a, 4-chloro-2-methoxy-5-(trifluoromethyl)phenyl isocyanate was reacted with 4-(2-(N-methylcarbamoyl)-4-pyridyloxy)aniline to afford the urea.

Entry 96: 4-(2-(N-Methylcarbamoyl)-4-pyridyloxy)-2-chloroaniline was synthesized according to Method A6. 4-Chloro-2-methoxy-5-(trifluoromethyl)aniline was synthesized according to Method A7. 4-Chloro-2-methoxy-5-(trifluoromethyl)aniline was converted into 4-chloro-2-methoxy-5-(trifluoromethyl)phenyl isocyanate according to Method B 1. According to Method C1a, 4-chloro-2-methoxy-5-(trifluoromethyl)phenyl isocyanate was reacted with 4-(2-(N-methylcarbamoyl)-4-pyridyloxy)-2-chloroaniline afford the urea.

Entry 97: According to Method A2, Step 4, 4-amino-2-chlorophenol was reacted with 4-chloro-N-methyl-2-pyridinecarboxamide, which had been synthesized according to Method A2, Step 3b, to give 4-(2-(N-methylcarbamoyl)-4-pyridyloxy)-3-chloroaniline. 4-Chloro-2-methoxy-5-(trifluoromethyl)aniline was synthesized according to Method A7. 4-Chloro-2-methoxy-5-(trifluoromethyl)aniline was converted into 4-chloro-2-methoxy-5-(trifluoromethyl)phenyl isocyanate according to Method B1. According to Method C1a, 4-chloro-2-methoxy-5-(trifluoromethyl)phenyl isocyanate was reacted with 4-(2-(N-methylcarbamoyl)-4-pyridyloxy)-3-chloroaniline to afford the urea.

Entry 98: 4-Chloro-N-methyl-2-pyridinecarboxamide, which was synthesized according to Method A2, Step 3a, was reacted with 3-aminophenol according to Method A2, Step 4 to form 3-(-2-(N-methylcarbamoyl)-4-pyridyloxy)aniline. 4-Chloro-2-methoxy-5-(trifluoromethyl)aniline was synthesized according to Method A7. 4-Chloro-2-methoxy-5-(trifluoromethyl)aniline was converted into 4-chloro-2-methoxy-5-(trifluoromethyl)phenyl isocyanate according to Method B1. According to Method C1a, 4-chloro-2-methoxy-5-(trifluoromethyl)phenyl isocyanate as was reacted with 3-(-2-(N-methylcarbamoyl)-4-pyridyloxy)aniline to afford the urea.

Entry 99: 4-Chloropyridine-2-carbonyl chloride was reacted with ethylamine according to Method A2, Step 3b. The resulting 4-chloro-N-ethyl-2-pyridinecarboxamide was reacted with 4-aminophenol according to Method A2, Step 4 to give 4-(2-(N-ethylcarbamoyl)-4-pyridyloxy)aniline. 4-Chloro-2-methoxy-5-(trifluoromethyl)aniline was synthesized according to Method A7. 4-Chloro-2-methoxy-5-(trifluoromethyl)aniline was converted into 4-chloro-2-methoxy-5-(trifluoromethyl)phenyl isocyanate according to Method B1. According to Method C1a, 4-chloro-2-methoxy-5-(trifluoromethyl)phenyl isocyanate was reacted with 4-(2-(N-ethylcarbamoyl)-4-pyridyloxy)aniline to afford the urea.

Entry 100: 4-Chloropyridine-2-carbonyl chloride was reacted with isopropylamine according to Method A2, Step 3b. The resulting 4-chloro-N-isopropyl-2-pyridinecarboxamide was reacted with 4-aminophenol according to Method A2, Step 4 to give 4-(2-(N-isopropylcarbamoyl)-4-pyridyloxy) aniline. 4-Chloro-2-methoxy-5-(trifluoromethyl)aniline was synthesized according to Method A7. 4-Chloro-2-methoxy-5-(trifluoromethyl)aniline was converted into 4-chloro-2-methoxy-5-(trifluoromethyl)phenyl isocyanate according to Method B 1. According to Method C1a, 4-chloro-2-methoxy-5-(trifluoromethyl)phenyl isocyanate was reacted with 4-(2-(N-isopropylcarbamoyl)-4-pyridyloxy)aniline afford the urea.

Entry 101: 4-(3-N-Methylcarbamoylphenoxy)aniline was prepared according to Method A13. 2-Amino-3-methoxynaphthalene was synthesized as described Method A1. According to Method C3, 2-amino-3-methoxynaphthalene was reacted with bis(trichloromethyl) carbonate followed by 4-(3-N-methylcarbamoylphenoxy)aniline to form the urea.

Entry 102: 4-(2-(N-Methylcarbamoyl)-4-pyridyloxy) aniline was synthesized according to Method A2. 5-tert-Butyl-2-(2,5-dimethylpyrrolyl)aniline was synthesized according to Method A4. 5-tert-Butyl-2-(2,5-dimethylpyrrolyl) aniline was reacted with CDI followed by 4-(2-(N-methylcarbamoyl)-4-pyridyloxy)aniline according to Method C2d to afford the urea.

Entry 103: 4-Chloro-N-methyl-2-pyridinecarboxamide was synthesized according to Method A2, Step 3b. 4-Chloro- N-methyl-2-pyridinecarboxamide was reacted with 4-aminophenol according to Method A2, Step 4 using DMAC in place of DMF to give 4-(2-(N-methylcarbamoyl)-4-pyridyloxy)aniline. According to Method C2b, reaction of 3-amino-2-methoxyquinoline with CDI followed by 4-(2-(N-methylcarbamoyl)-4-pyridyloxy)aniline afforded bis(4-(2-(N-methylcarbamoyl)-4-pyridlyoxy)phenyl)urea.

Entry 104: 4-(4-(2-(N-Methylcarbamoyl)pyridyloxy)aniline was prepared according to Method A2. 3-Amino-2-methoxyquinoline was reacted with 4-(4-(2-(N-methylcarbamoyl) pyridyloxy)aniline according to Method C5 to afford the urea.

Entry 105: 4-(3-N-Methylcarbamoylphenoxy)aniline was prepared according to Method A13. 3-Amino-2-methoxyquinoline was reacted with 4-(3-N-methylcarbamoylphenoxy)aniline according to Method C2c to afford the urea.

Entry 106: 4-Chloropyridine-2-carbonyl chloride was reacted with isopropylamine according to Method A2, Step 3b. The resulting 4-chloro-N-isopropyl-2-pyridinecarboxamide was reacted with 4-aminophenol according to Method A2, Step 4 to give 4-(2-(N-isopropylcarbamoyl)-4-pyridyloxy)aniline. 3-Amino-2-methoxyquinoline was reacted with 4-(2-(N-isopropylcarbamoyl)-4-pyridyloxy)aniline according to Method C2c to afford the urea.

Entry 107: 4-Chloropyridine-2-carbonyl chloride HCl salt was reacted with ammonia according to Method A2, Step 3b to form 4-chloro-2-pyridinecarboxamide. 4-Chloro-2-pyridinecarboxamide was reacted with 4-aminophenol according to Method A2, Step 4 using DMAC in place of DMF to give 4-(2-carbamoyl-4-pyridyloxy)aniline. 4-(2-Carbamoyl-4-pyridyloxy)aniline was reacted with 4-(2-(N-isopropylcarbamoyl)-4-pyridyloxy)aniline according to Method C5 to afford the urea.

Entry 108: 4-Chloro-N-methyl-2-pyridinecarboxamide was synthesized according to Method A2, Step 3b. 4-Chloro-N-methyl-2-pyridinecarboxamide was reacted with 4-aminophenol according to Method A2, Step 4 using DMAC in place of DMF to give 4-(2-(N-methylcarbamoyl)-4-pyridyloxy)aniline. 3-Amino-2-methoxyquinoline was reacted with 4-(2-(N-methylcarbamoyl)-4-pyridyloxy)aniline according to Method C5 to afford the urea.

Entry 109: 4-Chloropyridine-2-carbonyl chloride HCl salt was reacted with ammonia according to Method A2, Step 3b to form 4-chloro-2-pyridinecarboxamide. 4-Chloro-2-pyridinecarboxamide was reacted with 3-aminophenol according to Method A2, Step 4 using DMAC in place of DMF to give 3-(2-carbamoyl-4-pyridyloxy)aniline. 3-Amino-2-methoxyquinoline was reacted with 3-(2-carbamoyl-4-pyridyloxy)aniline according to Method C5 to afford the urea.

Entry 110: 4-Chloro-N-methyl-2-pyridinecarboxamide, which was synthesized according to Method A2, Step 3a, was reacted with 3-aminophenol according to Method A2, Step 4 using DMAC in place of DMF to give 3-(-2-(N-methylcarbamoyl)-4-pyridyloxy)aniline. 3-Amino-2-methoxyquinoline was reacted with 3-(-2-(N-methylcarbamoyl)-4-pyridyloxy)aniline according to Method C5 to afford the urea.

Entry 111: 4-(4-(3-(N-Methylcarbamoyl)-2-methoxyphenoxy)aniline was prepared according to Method A8. 3-Amino-2-methoxyquinoline was reacted with 4-(4-(3-(N-Methylcarbamoyl)-2-methoxyphenoxy)aniline was according to Method C5 to afford the urea.

Entry 112: 5-(4-Aminophenoxy)isoindoline-1,3-dione was prepared according to Method A3. 3-Amino-2-methoxyquinoline was reacted with 5-(4-Aminophenoxy)isoindoline-1,3-dione was according to Method C2c to afford the urea.

TABLE 1

3-tert-Butylphenyl Ureas

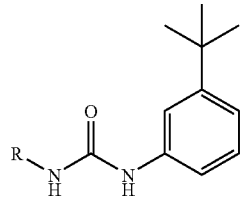

| Entry | R | mp (°C.) | HPLC (min.) | TLC $R_f$ | TLC Solvent System | Mass Spec. [Source] | Synth. Method |
|---|---|---|---|---|---|---|---|
| 1 | 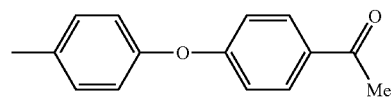 | | | 0.22 | 50% EtOAc/ 50% hexane | 418 (M + H) + (HPLC ES-MS) | A13 C3 |
| 2 | | | | 0.58 | 50% EtOAc/ 50% hexane | 403 (M + H) + (HPLC ES-MS) | A13 C3 |

TABLE 1-continued 3-tert-Butylphenyl Ureas

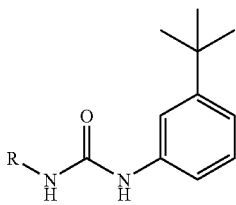

| Entry | R | mp (° C.) | HPLC (min.) | TLC $R_f$ | TLC Solvent System | Mass Spec. [Source] | Synth. Method |
|---|---|---|---|---|---|---|---|
| 3 | 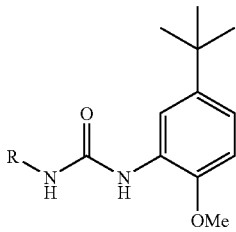 | 133-135 | | 0.68 | 100% EtOAc | 448 (M + H) + (FAB) | A8 C2d |

TABLE 2

5-tert-Butyl-2-methoxyphenyl Ureas

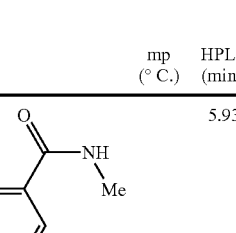

| Entry | R | mp (° C.) | HPLC (min.) | TLC $R_f$ | TLC Solvent System | Mass Spec. [Source] | Synth. Method |
|---|---|---|---|---|---|---|---|
| 4 | 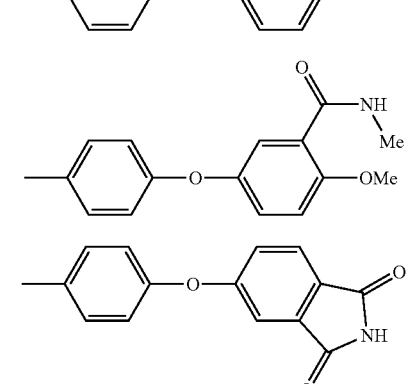 | | 5.93 | | | 448 (M + H) + (HPLC ES-MS) | A13 B1 C1a |
| 5 | 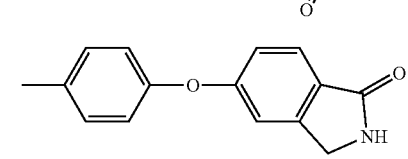 | 120-122 | | 0.67 | 100% EtOAc | 478 (M + H) + (FAB) | A8 C2d |
| 6 | | | | 0.40 | 50% EtOAc/ 50% hexane | 460 (M + H) + (HPLC ES-MS) | A3 C2d |
| 7 | | | | 0.79 | 50% EtOAc/ 50% hexane | 446 (M + H) + (HPLC ES-MS) | A12 C2d |

TABLE 3
5-(Trifluoromethyl)-2-methoxyphenyl Ureas
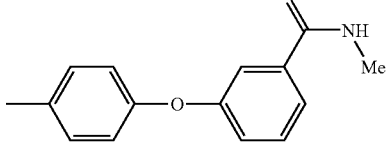
| Entry | R | mp (° C.) | HPLC (min.) | TLC $R_f$ | TLC Solvent System | Mass Spec. [Source] | Synth. Method |
|---|---|---|---|---|---|---|---|
| 8 | 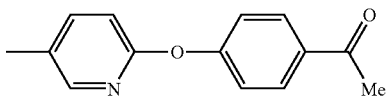 | 250 (dec) | | | | 460 (M + H) + (FAB) | A13 C2a |
| 9 | 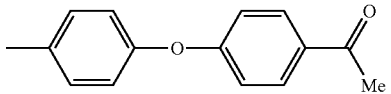 | 206-208 | | 0.54 | 10% MeOH/ 90% CH2Cl2 | 446 (M + H) + (HPLC ES-MS) | A3 step 2, A8 step 4, B1, C1a |
| 10 | 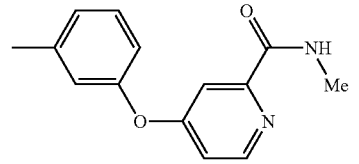 | | | 0.33 | 50% EtOAc/ 50% pet ether | 445 (M + H) + (HPLC ES-MS) | A13 C3 |
| 11 | 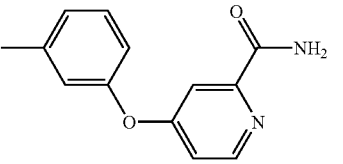 | | | 0.20 | 2% Et3N/ 98% EtOAc | 461 (M + H) + (HPLC ES-MS) | A2 C4 |
| 12 | 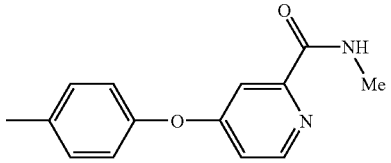 | | | 0.27 | 1% Et3N/ 99% EtOAc | 447 (M + H) + (HPLC ES-MS) | A2 C4 |
| 13 | 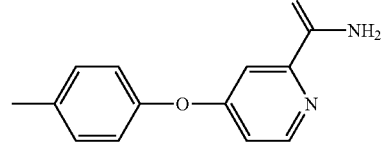 | | | 0.62 | 100% EtOAc | 461 (M + H) + (FAB) | A2 C2a |
| 14 |  | 114-117 | | 0.40 | 1% Et3N/ 99% EtOAc | 447 (M + H) + (FAB) | A2 C4 |

TABLE 3-continued 5-(Trifluoromethyl)-2-methoxyphenyl Ureas

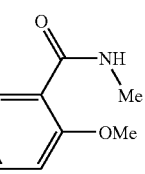

| Entry | R | mp (° C.) | HPLC (min.) | TLC R$_f$ | TLC Solvent System | Mass Spec. [Source] | Synth. Method |
|---|---|---|---|---|---|---|---|
| 15 | 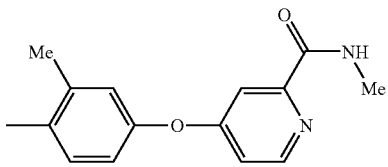 | 232-235 | | 0.54 | 100% EtOAc | 490 (M + H) + (FAB) | A8 C2d |
| 16 | 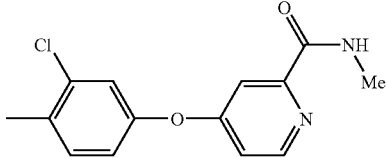 | 210-213 | | 0.29 | 5% MeOH/ 45% EtOAc/ 50% pet ether | 475 (M + H) + (HPLC ES-MS) | A5 B1 C1c |
| 17 | 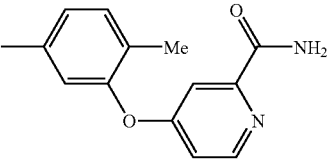 | 187-188 | | 0.17 | 50% EtOAc/ 50% pet ether | 495 (M + H) + (HPLC ES-MS) | A6 B1 C1a |
| 18 | 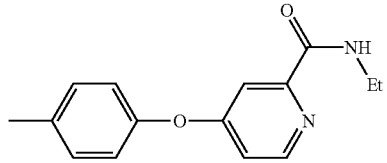 | | | 0.48 | 100% EtOAc | 475 (M + H) + (HPLC ES-MS) | A2 step 4, B1 C1a |
| 19 | 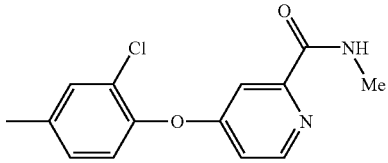 | 194-196 | | 0.31 | 5% MeOH/ 45% EtOAc/ 50% pet ether | 475 (M + H) + (HPLC ES-MS) | A2 B1 C1a |
| 20 | 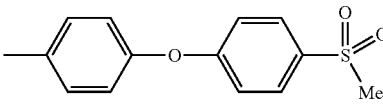 | 214-216 | | 0.25 | 5% MeOH/ 45% EtOAc/ 50% pet ether | 495 (M + H) + (HPLC ES-MS) | A2 C1a |
| 21 |  | 208-210 | | 0.30 | 50% EtOAc/ 50% hexane | 481 (M + H) + (HPLC ES-MS) | A18 C2a |

TABLE 3-continued 5-(Trifluoromethyl)-2-methoxyphenyl Ureas

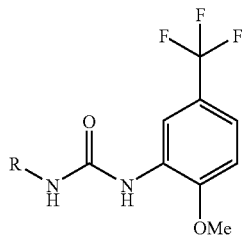

| Entry | R | mp (° C.) | HPLC (min.) | TLC R_f | TLC Solvent System | Mass Spec. [Source] | Synth. Method |
|---|---|---|---|---|---|---|---|
| 22 | 3-(4-methylphenoxy)benzamide | 188-190 | | 0.30 | 70% EtOAc/ 50% hexane | 447 (M + H) + (HPLC ES-MS) | A15, step 4, C1a |
| 23 | 5-(4-methylphenoxy)isoindoline-1,3-dione | | | 0.50 | 70% EtOAc/ 30% hexane | 472 (M + H) + (FAB) | A3 B1 C1a |
| 24 | 4-(4-methylphenoxy)-N,N-dimethylpyridine-2-carboxamide | 203-205 | | 0.13 | 100% EtOAc | 479 (M + H) + (HPLC ES-MS) | A2 B1 C1a |
| 25 | 5-(4-methylphenoxy)isoindolin-1-one | | | 0.09 | 75% EtOAc/ 25% hexane | 458 (M + H) + (HPLC ES-MS) | A12 C2d |
| 26 | 4-(4-methylphenoxy)acetophenone O-methyloxime | 169-171 | | 0.67 | 50% EtOAc/ 50% pet ether | 474 (M + H) + (HPLC ES-MS) | A13 step 1, A13 step 4, A16, B1 C1a |
| 27 | 4-(4-methylphenylthio)-N-methylpyridine-2-carboxamide | 218-219 | | 0.40 | 50% EtOAc/ 50% pet ether | 477 (M + H) + (HPLC ES-MS) | A2 step 3b, A2 step 4, B1, C1a |
| 28 | 5-(4-methylphenoxy)-N-methylisoindoline-1,3-dione | 212-214 | | 0.30 | 40% EtOAc/ 60% hexane | | A9 B1 C1a |

TABLE 3-continued
5-(Trifluoromethyl)-2-methoxyphenyl Ureas
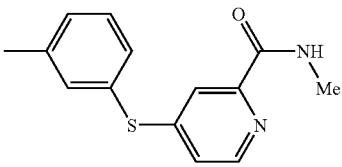
| Entry | R | mp (° C.) | HPLC (min.) | TLC $R_f$ | TLC Solvent System | Mass Spec. [Source] | Synth. Method |
|---|---|---|---|---|---|---|---|
| 29 | 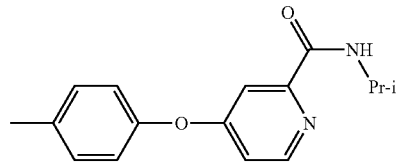 | | | 0.33 | 50% EtOAc/ 50% pet ether | 474 (M + H) + (HPLC ES-MS) | A2 step 3b, A2 step 4, B1, C1a |
| 30 | 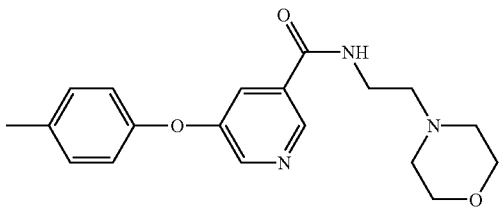 | 210-211 | | | | | A2 B1 C1a |
| 31 | 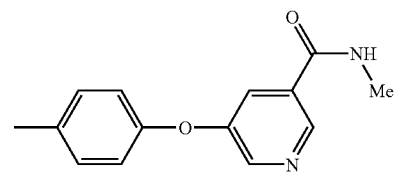 | 210-204 | | 0.43 | 10% MeOH/ CH2Cl2 | | A14 B1 C1a D4 |
| 32 | | 247-249 | | 0.57 | 10% MeOH/ CH2Cl2 | | A14 B1 C1a D4 |
| 33 | 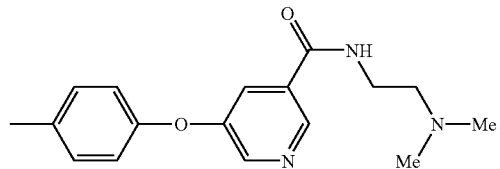 | 217-219 | | 0.07 | 10% MeOH/ CH2Cl2 | | A14 B1 C1a D4 |
| 34 | 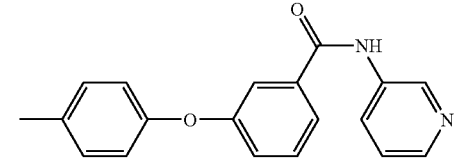 | | | 0.11 | 70% EtOAc/ 30% hexane | | A11 B1 C1f D1c |

TABLE 3-continued 5-(Trifluoromethyl)-2-methoxyphenyl Ureas

| Entry | R | mp (° C.) | HPLC (min.) | TLC R$_f$ | TLC Solvent System | Mass Spec. [Source] | Synth. Method |
|---|---|---|---|---|---|---|---|
| 35 | | | | 0.38 | 70% EtOAc/ 30% hexane | | A11 B1 C1f D1c |
| 36 | | | | 0.77 | 70% EtOAc/ 30% hexane | | A11 B1 C1f D1c |
| 37 | | | | 0.58 | 70% EtOAc/ 30% hexane | | A11 B1 C1f D1c |
| 38 | | | | 0.58 | 70% EtOAc/ 30% hexane | | A11 B1 C1f D1c |
| 39 | | | | 0.17 | 70% EtOAc/ 30% hexane | | A11 B1 C1f D1c |

TABLE 3-continued 5-(Trifluoromethyl)-2-methoxyphenyl Ureas

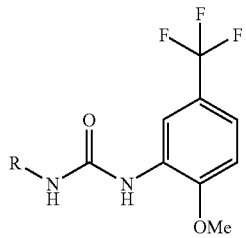

| Entry | R | mp (° C.) | HPLC (min.) | TLC $R_f$ | TLC Solvent System | Mass Spec. [Source] | Synth. Method |
|---|---|---|---|---|---|---|---|
| 40 | | | | 0.21 | 70% EtOAc/ 30% hexane | | A11 B1 C1f D1c |

TABLE 4

3-(Trifluoromethyl)-4-chlorophenyl Ureas

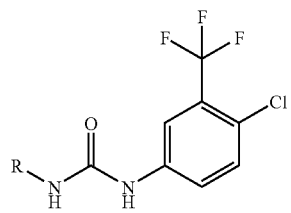

| Entry | R | mp (° C.) | HPLC (min.) | TLC $R_f$ | TLC Solvent System | Mass Spec. [Source] | Synth. Method |
|---|---|---|---|---|---|---|---|
| 41 | | 163-165 | | 0.08 | 50% EtOAc/ 50% pet ether | 464 (M + H) + (HPLC ES-MS) | A13 C3 |
| 42 | | 215 | | 0.06 | 50% EtOAc/ 50% pet ether | 465 (M + H) + (HPLC ES-MS) | A2 C1a |
| 43 | | | | 0.10 | 50% EtOAc/ 50% pet ether | 451 (M + H) + (HPLC ES-MS) | A2 C1a |

TABLE 4-continued 3-(Trifluoromethyl)-4-chlorophenyl Ureas

| Entry | R | mp (° C.) | HPLC (min.) | TLC R$_f$ | TLC Solvent System | Mass Spec. [Source] | Synth. Method |
|---|---|---|---|---|---|---|---|
| 44 | | | | 0.25 | 30% EtOAc/ 70% pet ether | 451 (M + H) + (HPLC ES-MS) | A2 C1a |
| 45 | | | | 0.31 | 30% EtOAc/ 70% pet ether | 465 (M + H) + (HPLC ES-MS) | A2 C1a |
| 46 | | 176-179 | | 0.23 | 40% EtOAc/ 60% hexane | 476 (M + H) + (FAB) | A3 C1a |
| 47 | | | | 0.29 | 5% MeOH/ 45% EtOAc/ 50% pet ether | 478 (M + H) + (HPLC ES-MS) | A5 C1c |
| 48 | | 206-209 | | 0.30 | 70% EtOAc/ 30% hexane | 500 (M + H) + (HPLC ES-MS) | A15 C1a |
| 49 | | 147-151 | | 0.22 | 50% EtOAc/ 50% pet ether | 499 (M + H) + (HPLC ES-MS) | A6 C1a |
| 50 | | | | 0.54 | 100% EtOAc | 479 (M + H) + (HPLC ES-MS) | A2 step 4, C1a |

TABLE 4-continued 3-(Trifluoromethyl)-4-chlorophenyl Ureas

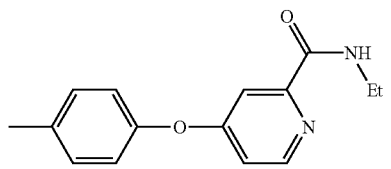

| Entry | R | mp (° C.) | HPLC (min.) | TLC R$_f$ | TLC Solvent System | Mass Spec. [Source] | Synth. Method |
|---|---|---|---|---|---|---|---|
| 51 | 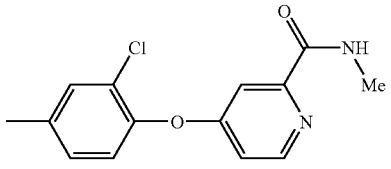 | 187-189 | | 0.33 | 5% MeOH/ 45% EtOAc/ 50% pet ether | 479 (M + H)+ (HPLC ES-MS) | A2 C1a |
| 52 | 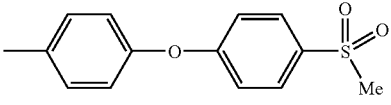 | 219 | | 0.18 | 5% MeOH/ 45% EtOAc/ 50% pet ether | 499 (M + H)+ (HPLC ES-MS) | A2 C1a |
| 53 | 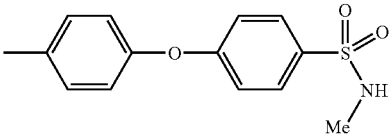 | 246-248 | | 0.30 | 50% EtOAc/ 50% hexane | 485 (M + H)+ (HPLC ES-MS) | A18 C1a |
| 54 | 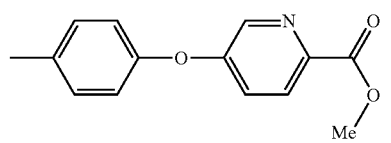 | 196-200 | | 0.30 | 70% EtOAc/ 30% hexane) | 502 (M + H)+ (HPLC ES-MS) | A15 C1a |
| 55 | 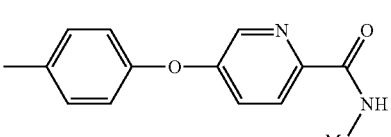 | 228-230 | | 0.30 | 30% EtOAc/ 70% CH2Cl2 | 466 (M + H)+ (HPLC ES-MS) | A18, C1a |
| 56 | 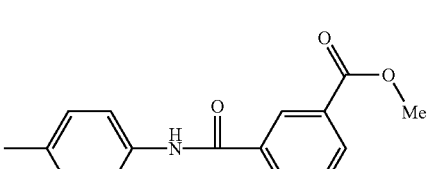 | 238-245 | | | | 465 (M + H)+ (HPLC ES-MS) | A18, C1a, D2 |
| 57 | 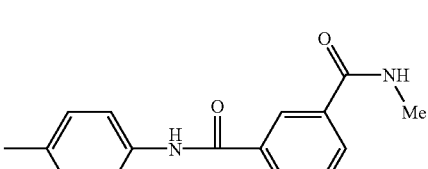 | 221-222 | | 0.75 | 80% EtOAc/ 20% hexane | 492 (M + H)+ (FAB) | C1d D1a |
| 58 | | 247 | | 0.35 | 100% EtOAc | | C1d D1a D2 |

TABLE 4-continued 3-(Trifluoromethyl)-4-chlorophenyl Ureas

| Entry | R | mp (° C.) | HPLC (min.) | TLC R$_f$ | TLC Solvent System | Mass Spec. [Source] | Synth. Method |
|---|---|---|---|---|---|---|---|
| 59 | *4-methylphenoxy-pyridine-2-carboxylic acid N,N-dimethylamide* | 198-200 | | 0.09 | 100% EtOAc | 479 (M + H) + (HPLC ES-MS) | A2 C1a |
| 60 | *1-[4-(4-methylphenoxy)phenyl]ethanone O-methyloxime* | 158-160 | | 0.64 | 50% EtOAc/ 50% pet ether | | A13 step 1, A13 step 4, A16, C1a |
| 61 | *3-(4-methylphenoxy)-N-(2-morpholinoethyl)benzamide* | 195-197 | | 0.39 | 10% MeOH/ CH2Cl2 | | A13 C1a |
| 62 | *3-(4-methylphenoxy)-N-(2-piperidinoethyl)benzamide* | 170-172 | | 0.52 | 10% MeOH/ CH2Cl2 | | A13 C1a |
| 63 | *3-(4-methylphenoxy)-N-(tetrahydrofurfuryl)benzamide* | 168-171 | | 0.39 | 10% MeOH/ CH2Cl2 | | A13 C1a |
| 64 | *3-(4-methylphenoxy)-N-((1-ethylpyrrolidin-2-yl)methyl)benzamide* | 176-177 | | 0.35 | 10% MeOH/ CH2Cl2 | | A13 C1a |
| 65 | *4-(4-methylphenylthio)-pyridine-2-carboxylic acid N-methylamide* | 130-133 | | | | 487 (M + H) + (HPLC ES-MS) | A2 C1a |

TABLE 4-continued

3-(Trifluoromethyl)-4-chlorophenyl Ureas

| Entry | R | mp (° C.) | HPLC (min.) | TLC R$_f$ | TLC Solvent System | Mass Spec. [Source] | Synth. Method |
|---|---|---|---|---|---|---|---|
| 66 | | 155 | | | | | A2<br>C1a |
| 67 | | 225-229 | | 0.23 | 100% EtOAc | | C1e<br>D3<br>D1b |
| 68 | | 234-236 | | 0.29 | 40% EtOAc/ 60% hexane | | A9<br>C1a |
| 69 | | | | 0.48 | 50% EtOAc/ 50% pet ether | 481 (M + H) + (HPLC ES-MS) | A2 step 3b,<br>A2 step 4,<br>C1a |
| 70 | | | | 0.46 | 5% MeOH/ 95% CH2Cl2 | 564 (M + H) + (HPLC ES-MS) | A10<br>C1a |
| 71 | | 199-201 | | 0.50 | 10% MeOH/ CH2Cl2 | | A14<br>C1a<br>D4 |

TABLE 4-continued
3-(Trifluoromethyl)-4-chlorophenyl Ureas
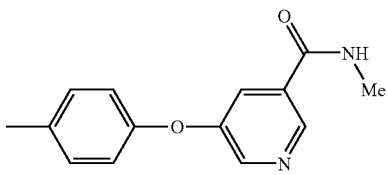
| Entry | R | mp (° C.) | HPLC (min.) | TLC R$_f$ | TLC Solvent System | Mass Spec. [Source] | Synth. Method |
|---|---|---|---|---|---|---|---|
| 72 | 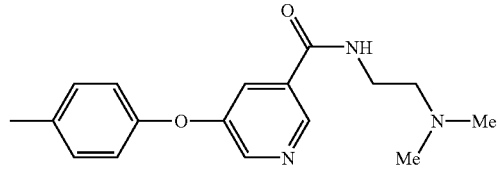 | 235-237 | | 0.55 | 10% MeOH/ CH2Cl2 | | A14 C1a D4 |
| 73 | 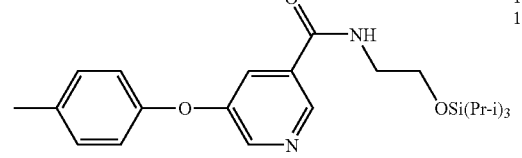 | 200-201 | | 0.21 | 50% MeOH/ CH2Cl2 | | A14 C1a D4 |
| 74 | 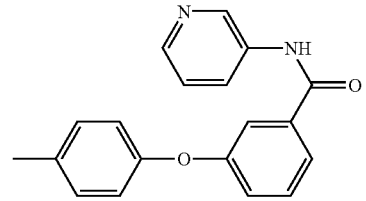 | 145-148 | | | | | A2 step 1-3b, A17, C1a |
| 75 | 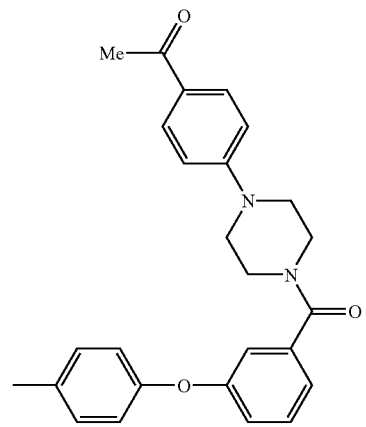 | | | 0.12 | 70% EtOAc/ 30% hexane | 527 (M + H) + (HPLC ES-MS) | A11 C1f D1c |
| 76 |  | | | 0.18 | 70% EtOAc/ 30% hexane | | A11 C1f D1c |

TABLE 4-continued
3-(Trifluoromethyl)-4-chlorophenyl Ureas
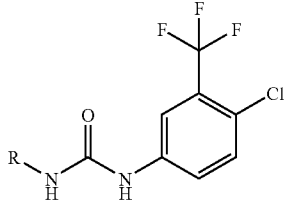
| Entry | R | mp (° C.) | HPLC (min.) | TLC R$_f$ | TLC Solvent System | Mass Spec. [Source] | Synth. Method |
|---|---|---|---|---|---|---|---|
| 77 | 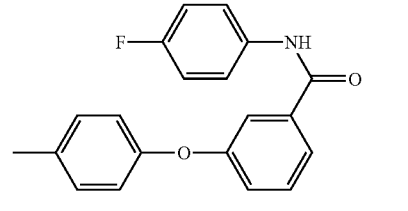 | | | 0.74 | 70% EtOAc/ 30% hexane | | A11 C1f D1c |
| 78 | 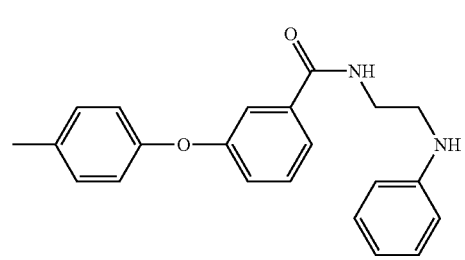 | | | 0.58 | 70% EtOAc/ 30% hexane | | A11 C1f D1c |
| 79 | 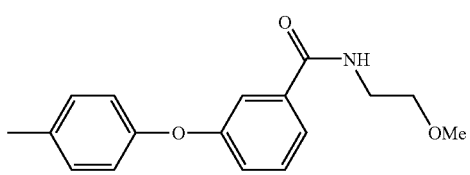 | | | 0.47 | 70% EtOAc/ 30% hexane | 569 (M + H) + (HPLC ES-MS) | A11 C1f D1c |
| 80 | 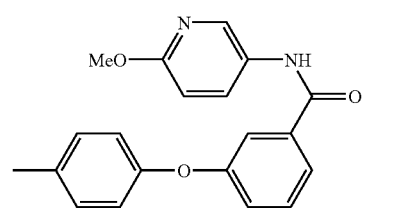 | | | 0.18 | 70% EtOAc/ 30% hexane | 508 (M + H) + (HPLC ES-MS) | A11 C1f D1c |
| 81 | 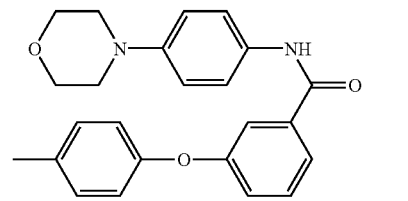 | | | 0.58 | 70% EtOAc/ 30% hexane | 557 (M + H) + (HPLC ES-MS) | A11 C1f D1c |
| 82 | | | | 0.37 | 70% EtOAc/ 30% hexane | 611 (M + H) + (HPLC ES-MS) | A11 C1f D1c |

TABLE 4-continued

3-(Trifluoromethyl)-4-chlorophenyl Ureas

| Entry | R | mp (° C.) | HPLC (min.) | TLC $R_f$ | TLC Solvent System | Mass Spec. [Source] | Synth. Method |
|---|---|---|---|---|---|---|---|
| 83 | (2-pyridyl-piperazinyl-carbonyl-phenoxy-tolyl) | | | 0.19 | 70% EtOAc/ 30% hexane | | A11 C1f D1c |
| 84 | (tolyloxy-pyridyl-carboxamide-ethanol) | 179-183 | | | | | A2 step 1-3b, A17, C1a, D5 |

TABLE 5

3-(Trifluoromethyl)-4-bromophenyl Ureas

| Entry | R | mp (° C.) | HPLC (min.) | TLC $R_f$ | TLC Solvent System | Mass Spec. [Source] | Synth. Method |
|---|---|---|---|---|---|---|---|
| 85 | (tolyloxy-pyridyl-N-Me-carboxamide) | 186-187 | | 0.13 | 50% EtOAc/ 50% pet ether | 509 (M + H) + (HPLC ES-MS) | A2 B1 C1a |
| 86 | (chloro-tolyloxy-pyridyl-N-Me-carboxamide) | 150-152 | | 0.31 | 50% EtOAc/ 50% pet ether | 545 (M + H) + (HPLC ES-MS) | A6 B1 C1a |

TABLE 5-continued

| | Structure | mp (°C) | | MS | Method |
|---|---|---|---|---|---|
| 87 | 2-Cl-4-Me-phenoxy-pyridine-2-C(O)NHMe | 217-219 | 0.16 50% EtOAc/ 50% pet ether | 545 (M + H)+ (HPLC ES-MS) | A2 B1 C1a |
| 88 | 4-Me-phenoxy-pyridine-2-C(O)NHEt | 183-184 | 0.31 50% EtOAc/ 50% pet ether | 525 (M + H)+ (HPLC ES-MS) | A2 B1 C1a |
| 89 | 3-Me-phenoxy-pyridine-2-C(O)NHMe | | 0.21 50% EtOAc/ 50% pet ether | 511 (M + H)+ (HPLC ES-MS) | A2 B1 C1a |
| 90 | 2-Me-4-Me-phenoxy-pyridine-2-C(O)NHMe | | 0.28 50% EtOAc/ 50% pet ether | 525 (M + H)+ (HPLC ES-MS) | A2 B1 C1a |
| 91 | 4-Me-phenoxy-pyridine-2-C(O)NMe2 | 214-216 | 0.28 50% EtOAc/ 50% pet ether | 522 (M + H)+ (HPLC ES-MS) | A2 B1 C1a |
| 92 | 4-Me-phenylthio-pyridine-2-C(O)NHMe | | 0.47 50% EtOAc/ 50% pet ether | 527 (M + H)+ (HPLC ES-MS) | A2 step 3b, A2 step 4, B1, C1a |
| 93 | 3-Me-phenylthio-pyridine-2-C(O)NHMe | | 0.46 50% EtOAc/ 50% pet ether | 527 (M + H)+ (HPLC ES-MS) | A2 step 3b, A2 step 4, B1, C1a |
| 94 | 4-Me-phenoxy-pyridine-2-C(O)NH-CH2CH2-morpholine | 145-150 | 0.41 5% MeOH/ 95% CH2Cl2 | | A10 B1 C1a |

TABLE 5-continued 5-(Trifluoromethyl)-4-chloro-2-methoxyphenyl Ureas

| Entry | R | mp (°C.) | HPLC (min.) | TLC $R_f$ | TLC Solvent System | Mass Spec. [Source] | Synth. Method |
|---|---|---|---|---|---|---|---|
| 95 | 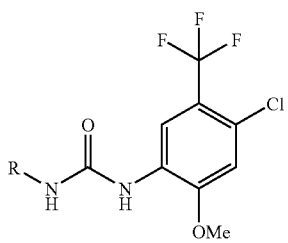 | 140-144 | | 0.29 | 5% MeOH/ 45% EtOAc/ 50% pet ether | 495 (M + H) + (HPLC ES-MS) | A2 A7 B1 C1a |
| 96 | 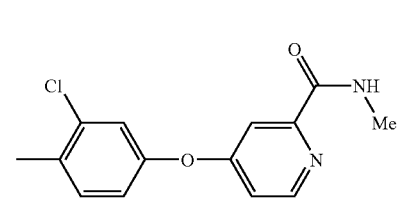 | 244-245 | | 0.39 | 5% MeOH/ 45% EtOAc/ 50% pet ether | 529 (M + H) + (HPLC ES-MS) | A6 A7 B1 C1a |
| 97 | 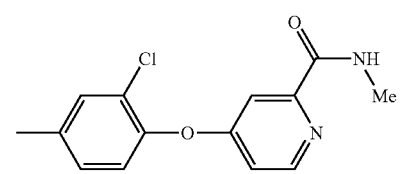 | 220-221 | | 0.25 | 5% MeOH/ 45% EtOAc/ 50% pet ether | 529 (M + H) + (HPLC ES-MS) | A2 A7 B1 C1a |
| 98 | 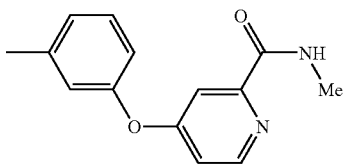 | | | 0.27 | 5% MeOH/ 45% EtOAc/ 50% pet ether | 495 (M + H) + (HPLC ES-MS) | A2 A7 B1 C1a |
| 99 | 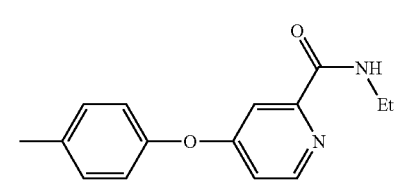 | 180-181 | | 0.52 | 5% MeOH/ 45% EtOAc/ 50% pet ether | 509 (M + H) + (HPLC ES-MS) | A2 A7 B1 C1a |
| 100 | 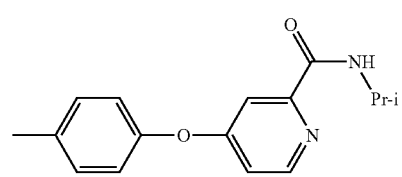 | 162-165 | | | | | A2 A7 B1 C1a |

TABLE 6

| | | | | | TLC | Mass | |
| --- | --- | --- | --- | --- | --- | --- | --- |
| | | mp | HPLC | TLC | Solvent | Spec. | Synth. |
| Entry | R | (° C.) | (min.) | R_f | System | [Source] | Method |
| 101 | (structure) | 162-165 | | | | | A13 A1 C3 |
| 102 | (structure) | | | 0.10 | 50% EtOAc/ 50% hexane | 442 (M + H) + (HPLC ES-MS) | A2 A4 C2d |
| 103 | (structure) | 125-130 | | 0.24 | 40% EtOAc/ 60% hexane | 512 (M + H) + (FAB) | A2 C2b |
| 104 | (structure) | | | 0.30 | 1% Et3N/ 99% EtOAc | 414 (M + H) + (HPLC ES-MS) | A2 C5 |

TABLE 7
2-Methoxyquinolyl Ureas
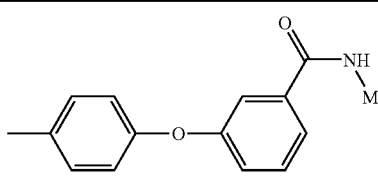
| Entry | R | mp (° C.) | HPLC (min.) | TLC $R_f$ | TLC Solvent System | Mass Spec. [Source] | Synth. Method |
|---|---|---|---|---|---|---|---|
| 105 | 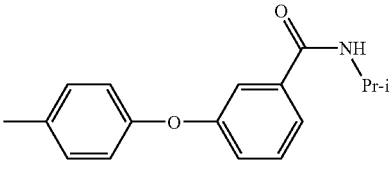 | 213-214 | | 0.20 | 5% MeOH/ 95% CHCl3 | 443 (M+H)+ (FAB) | A13 C2c |
| 106 | 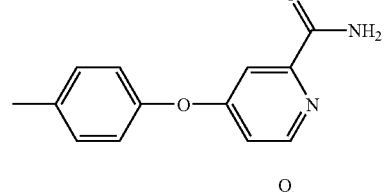 | 244-245 | | | | | A2 C2c |
| 107 | 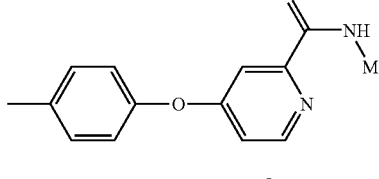 | | | 0.52 | 100% EtOAc | 430 (M+H)+ (FAB) | A2 C5 |
| 108 | 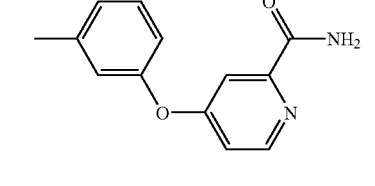 | | | 0.55 | 100% EtOAc | 444 (M+H)+ (FAB) | A2 C5 |
| 109 | 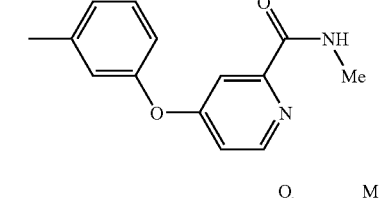 | | | 0.30 | 100% EtOAc | 430 (M+H)+ (FAB) | A2 C5 |
| 110 | 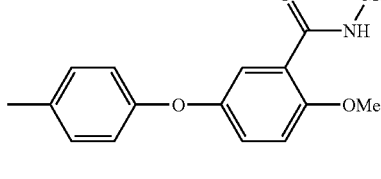 | | | 0.60 | 100% EtOAc | 444 (M+H)+ (FAB) | A2 C5 |
| 111 | | 144-146 | | | | | A8 C5 |

TABLE 7-continued

2-Methoxyquinolyl Ureas

| Entry | R | mp (° C.) | HPLC (min.) | TLC $R_f$ | TLC Solvent System | Mass Spec. [Source] | Synth. Method |
|---|---|---|---|---|---|---|---|
| 112 | | | | | | | A3 C2c |

Biological Examples

In Vitro raf Kinase Assay

In an in vitro kinase assay, raf was incubated with MEK in 20 mM Tris-HCl, pH 8.2 containing 2 mM 2-mercaptoethanol and 100 mM NaCl. This protein solution (20 µL) was mixed with water (5 µL) or with compounds diluted with distilled water from 10 mM stock solutions of compounds dissolved in DMSO. The kinase reaction was initiated by adding 25 µL [$\lambda$-$^{33}$P]ATP (1000-3000 dpm/pmol) in 80 mM Tris-HCl, pH 7.5, 120 mM NaCl, 1.6 mM DTT, 16 mM MgCl$_2$. The reaction mixtures were incubated at 32° C., usually for 22 min. Incorporation of $^{33}$P into protein was assayed by harvesting the reaction onto phosphocellulose mats, washing away free counts with a 1% phosphoric acid solution and quantitating phosphorylation by liquid scintillation counting. For high throughput screening, 10 µM ATP and 0.4 µM MEK was used. In some experiments, the kinase reaction was stopped by adding an equal amount of Laemmli sample buffer. Samples were boiled 3 min and the proteins resolved by electrophoresis on 7.5% Laemmli gels. Gels were fixed, dried and exposed to an imaging plate (Fuji). Phosphorylation was analyzed using a Fujix Bio-Imaging Analyzer System.

All compounds exemplified displayed IC$_{50}$s of between 1 nM and 10 µM.

Cellular Assay:

For in vitro growth assay, human tumor cell lines, including but not limited to HCT116 and DLD-1, containing mutated K-ras genes were used in standard proliferation assays for anchorage dependent growth on plastic or anchorage independent growth in soft agar. Human tumor cell lines were obtained from ATCC (Rockville, Md.) and maintained in RPMI with 10% heat inactivated fetal bovine serum and 200 mM glutamine. Cell culture media and additives were obtained from Gibco/BRL (Gaithersburg, Md.) except for fetal bovine serum (JRH Biosciences, Lenexa, Kans.). In a standard proliferation assay for anchorage dependent growth, 3×10$^3$ cells were seeded into 96-well tissue culture plates and allowed to attach overnight at 37° C. in a 5% CO$_2$ incubator. Compounds were titrated in media in dilution series and added to 96-well cell cultures. Cells were allowed to grow 5 days typically with a feeding of fresh compound containing media on day three. Proliferation was monitored by measuring metabolic activity with standard XTT calorimetric assay (Boehringer Mannheim) measured by standard ELISA plate reader at OD 490/560, or by measuring $^3$H-thymidine incorporation into DNA following an 8 h culture with 1 µCu $^3$H-thymidine, harvesting the cells onto glass fiber mats using a cell harvester and measuring $^3$H-thymidine incorporation by liquid scintillant counting.

For anchorage independent cell growth, cells were plated at 1×10$^3$ to 3×10$^3$ in 0.4% Seaplaque agarose in RPMI complete media, overlaying a bottom layer containing only 0.64% agar in RPMI complete media in 24-well tissue culture plates. Complete media plus dilution series of compounds were added to wells and incubated at 37° C. in a 5% CO$_2$ incubator for 10-14 days with repeated feedings of fresh media containing compound at 3-4 day intervals. Colony formation was monitored and total cell mass, average colony size and number of colonies were quantitated using image capture technology and image analysis software (Image Pro Plus, media Cybernetics).

In Vivo Assay:

An in vivo assay of the inhibitory effect of the compounds on tumors (e.g., solid cancers) mediated by raf kinase can be performed as follows:

CDI nu/nu mice (6-8 weeks old) are injected subcutaneously into the flank at 1×10$^6$ cells with human colon adenocarcinoma cell line. The mice are dosed i.p., i.v. or p.o. at 10, 30, 100, or 300 mg/Kg beginning on approximately day 10, when tumor size is between 50-100 mg. Animals are dosed for 14 consecutive days once a day; tumor size was monitored with calipers twice a week.

The inhibitory effect of the compounds on raf kinase and therefore on tumors (e.g., solid cancers) mediated by raf kinase can further be demonstrated in vivo according to the technique of Monia et al. (*Nat. Med.* 1996, 2, 668-75).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of Formula I

A-D-B    (I)

or a pharmaceutically acceptable salt thereof, wherein:
D is —NH—C(O)—NH—,
A is of the formula: -L-(M-L$^1$)$_q$, where
L is substituted or unsubstituted phenyl bound directly to D,
L$^1$ is phenyl substituted by —C(O)R$_x$, or pyridinyl substituted by —C(O)R$_x$,
M is oxygen,
q is 1 and
B is a substituted or unsubstituted pyridyl group, a substituted or unsubstituted quinolinyl group or a substituted or unsubstituted isoquinolinyl group,
where B is substituted, L is substituted or L$^1$ is additionally substituted, the substituents are selected from the group consisting of halogen, up to per-halo, and Wn, where n is 0-3;
R$_x$, is NR$_a$R$_b$ where R$_a$ and R$_b$ are,
a) independently hydrogen, C$_1$-C$_{10}$ alkyl, C$_{3-10}$ cycloalkyl, C$_{2-10}$ alkenyl, C$_{1-10}$ alkenoyl, phenyl, pyridinyl, piperazinyl, morpholinyl, piperidinyl, pyrrolidinyl, tetrahydrofuryl, substituted C$_{1-10}$ alkyl, substituted C$_{3-10}$ cycloalkyl, substituted phenyl, substituted pyridinyl, substituted piperazinyl, substituted morpholinyl, substituted piperidinyl, substituted pyrrolidinyl, or substituted tetrahydrofuryl, where R$_a$ and R$_b$ are a substituted group, they are substituted by halogen up to per halo, hydroxy, C$_{1-10}$ alkyl, C$_{1-10}$ alkoxy, C$_{3-10}$ cycloalkyl, phenyl, pyridinyl, piperazinyl, morpholinyl, piperidinyl, pyrrolidinyl, tetrahydrofuryl, halo-substituted C$_{1-6}$ alkyl up to per halo alkyl, halo-substituted phenyl up to per halo phenyl, halo-substituted pyridinyl, up to per halo pyridinyl, halo-substituted morpholinyl, up to per halo morpholinyl, halo-substituted piperidinyl, up to per halo piperidinyl, halo-substituted pyrrolidinyl, up to per halo pyrrolidinyl, or halo-substituted tetrahydrofuryl up to per halo tetrahydrofuryl,
each W is independently —CN, —CO$_2$R$^7$, —C(O)NR$^7$R$^7$, —C(O)—R$^7$, —NO$_2$, —OR', —SR$^7$, —NR$^7$R$^7$, —NR$^7$C(O)OR$^7$, —NR$^7$C(O)R$^7$, C$_1$-C$_{10}$ alkyl, C$_1$-C$_{10}$ alkoxy, C$_2$-C$_{10}$ alkenyl, C$_1$-C$_{10}$ alkenoyl, C$_3$-C$_{10}$ cycloalkyl, phenyl, pyridinyl, pyrazolyl, piperazinyl, morpholinyl, piperidinyl, pyrrolidinyl, or tetrahydrofuryl, substituted C$_1$-C$_{10}$ alkyl, substituted C$_1$-C$_{10}$ alkoxy, substituted C$_2$-C$_{10}$ alkenyl, substituted C$_1$-C$_{10}$ alkenoyl, substituted C$_3$-C$_{10}$ cycloalkyl substituted phenyl, substituted pyridinyl, substituted pyrazolyl substituted piperazinyl, substituted morpholinyl, substituted piperidinyl, substituted pyrrolidinyl, or substituted tetrahydrofuryl, where W is a substituted group, it is substituted by one or more substituents which are each, independently, —CN, —CO$_2$R$^7$, —C(O)R$^7$, —C(O)NR$^7$R$^7$, —OR', —SR', —NR$^7$R$^7$, —NO$_2$, —NR$^7$C(O)R$^7$, —NR$^7$C(O)OR$^7$ or halogen,
each R$^7$ is independently H, C$_1$-C$_{10}$ alkyl, C$_1$-C$_{10}$ alkoxy, C$_2$-C$_{10}$ alkenyl, C$_1$-C$_{10}$ alkenoyl, C$_3$-C$_{10}$ cycloalkyl, phenyl or pyridinyl up to per-halosubstituted C$_1$-C$_{10}$ alkyl, up to per-halosubstituted C$_3$-C$_{10}$ cycloalkyl or up to per-halo substituted phenyl.

2. A compound as in claim 1 wherein the cyclic structures of B and L bound directly to D are substituted in the ortho position by hydrogen.

3. A compound of claim 1 wherein B of Formula I is a substituted pyridyl, substituted quinolinyl or substituted isoquinolinyl group substituted 1 to 3 times by one or more substituents which are each, independently, —CN, halogen, C$_1$-C$_{10}$ alkyl, C$_1$-C$_{10}$ alkoxy, —OH, up to per halo substituted C$_1$-C$_{10}$ alkyl, up to per halo substituted C$_1$-C$_{10}$ alkoxy or phenyl substituted by halogen up to per halo.

4. A compound of claim 1 wherein L$^1$ is additionally substituted 1 to 3 times by one or more substituents which are each, independently, C$_1$-C$_{10}$ alkyl, up to per halo substituted C$_1$-C$_{10}$ alkyl, —CN, —OH, halogen, C$_1$-C$_{10}$ alkoxy or up to per halo substituted C$_1$-C$_{10}$ alkoxy.

5. A compound of claim 1 wherein L$^1$ is substituted only by —C(O)R$_x$.

6. A compound of claim 1 wherein L$^1$ is substituted by —C(O)R$_x$ wherein R$_x$ is NR$_a$R$_b$ and R$_a$ and R$_b$ are independently hydrogen or C$_1$-C$_{10}$ alkyl.

7. A compound of claim 1 which is a pharmaceutically acceptable salt of a compound of formula I which is
a) a basic salt of an organic acid or inorganic acid which is hydrochloric acid, hydrobromic acid, sulphuric acid, phosphoric acid, methanesulfonic acid, trifluorosulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, or mandelic acid; and
b) an acid salt of an organic or inorganic base containing a cation which is an alkaline cation, alkaline earth cation, the ammonium cation, an aliphatic substituted ammonium cation or an aromatic substituted ammonium cation.

8. A pharmaceutical composition comprising a compound of Formula I of claim 1 or a pharmaceutically acceptable salt of a compound of formula I, and a physiologically acceptable carrier.

9. A compound which is

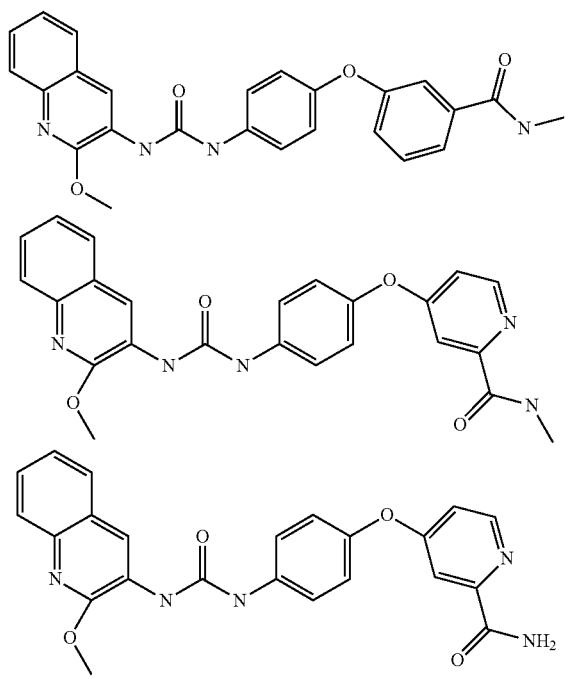

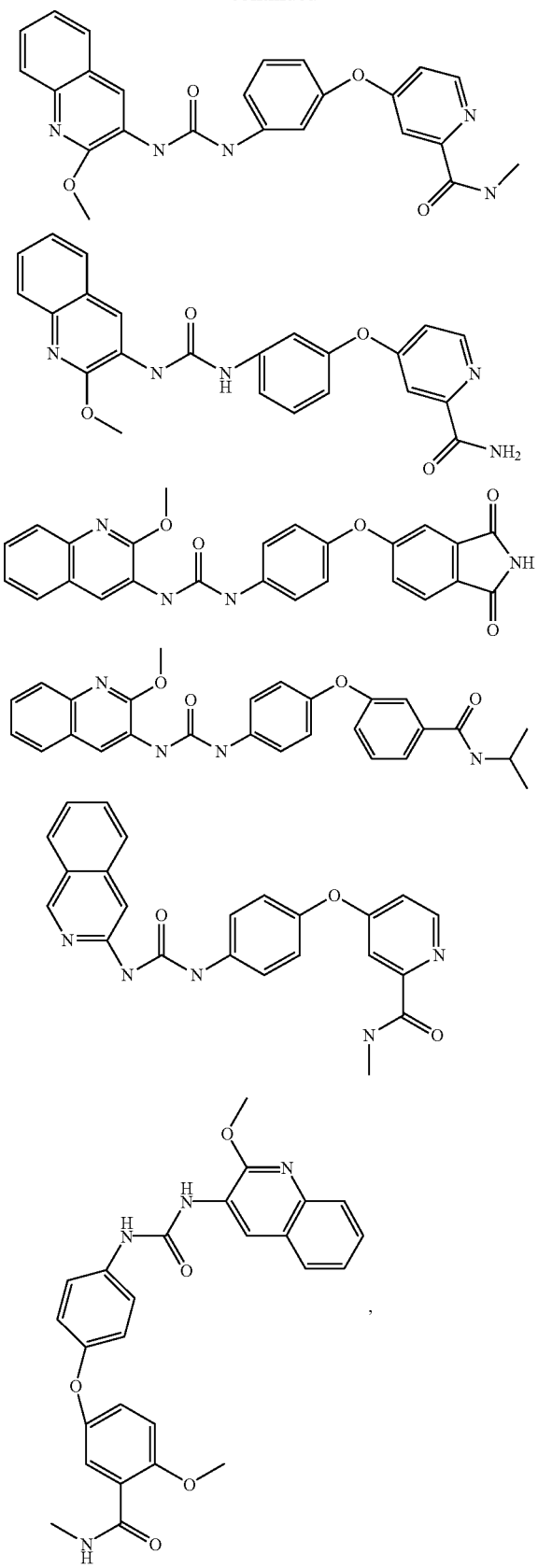
or a pharmaceutically acceptable salt thereof.
10. A pharmaceutical composition comprising a compound which is
or a pharmaceutically acceptable salt thereof.

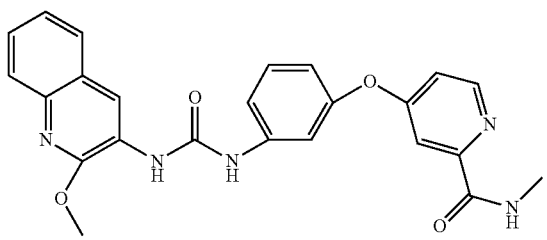
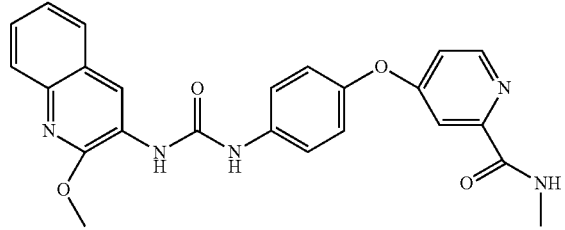
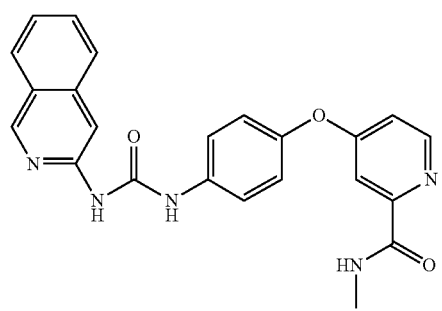
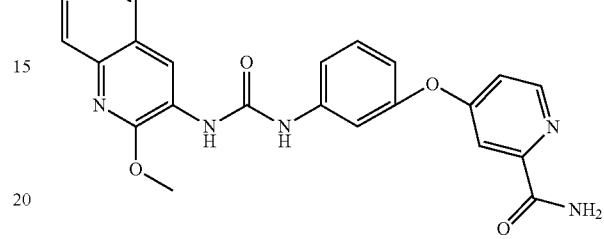
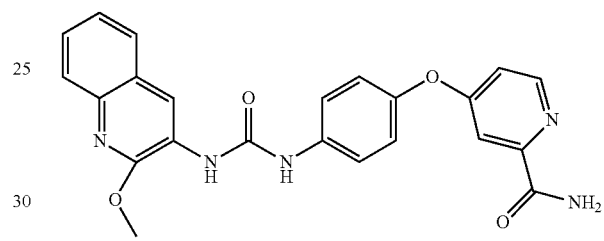
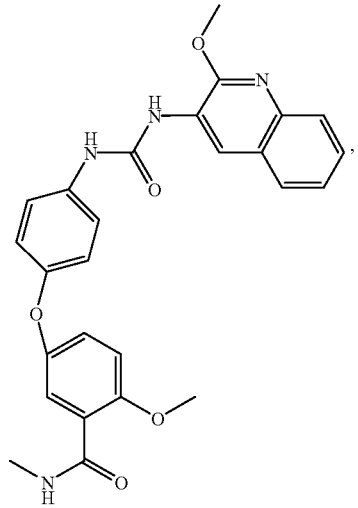
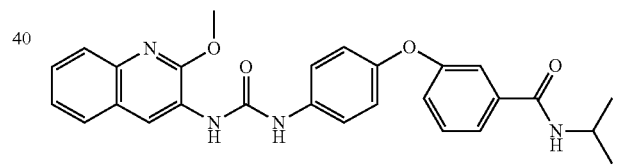
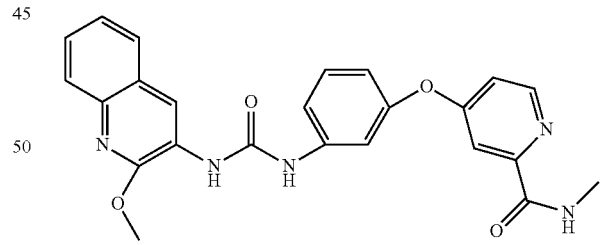
or a pharmaceutically acceptable salt thereof, and a physiologically acceptable carrier.
11. A method for treating colorectal cancer in a host, comprising administering to a host in need thereof an effective amount of a compound which is
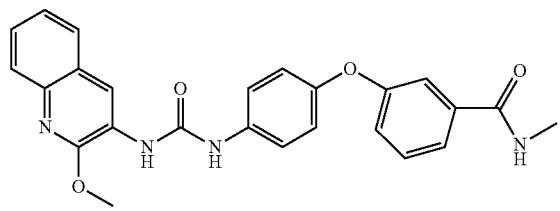
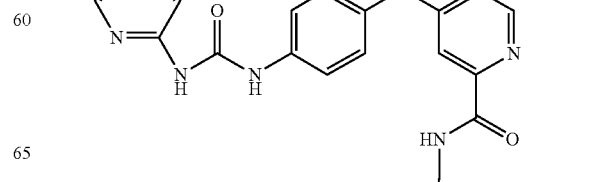

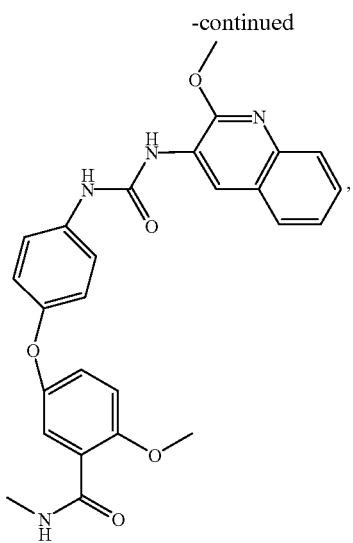

or a pharmaceutically acceptable salt thereof.

12. A compound of Formula I:

A-D-B    (I)

or a pharmaceutically acceptable salt thereof, wherein
D is —NH—C(O)—NH—,
A is of the formula: -L-(M-L$^1$)$_q$, where L is phenyl bound directly to D, L$^1$ is pyridinyl, M is oxygen and q is 1; and
B is a substituted or unsubstituted pyridyl, quinolinyl or isoquinolinyl group,
wherein L$^1$ is substituted by —C(O)R$_x$,
R$_x$ is NR$_a$R$_b$ where R$_a$ and R$_b$ are independently hydrogen or C$_1$-C$_{10}$ alkyl,
where B is substituted, L is substituted or L$^1$ is additionally substituted, the substituents are selected from the group consisting of halogen, up to per-halo, and Wn, where n is 0-3;
wherein each W is independently —CN, —CO$_2$R$^7$, —C(O)NR$^7$R$^7$, —C(O)—R$^7$, —NO$_2$, —OW, —SR$^7$, —NR$^7$R$^7$, —NR$^7$C(O)OR$^7$, —NR$^7$C(O)R$^7$, C$_1$-C$_{10}$ alkyl, C$_1$-C$_{10}$ alkoxy, C$_2$-C$_{10}$ alkenyl, C$_1$-C$_{10}$ alkenoyl, C$_3$-C$_{10}$ cycloalkyl, phenyl, pyridinyl, pyrazolyl, piperazinyl, morpholinyl, piperidinyl, pyrrolidinyl, tetrahydrofuryl, substituted C$_1$-C$_{10}$ alkyl, substituted C$_1$-C$_{10}$ alkoxy, substituted C$_2$-C$_{10}$ alkenyl, substituted C$_1$-C$_{10}$ alkenoyl, substituted C$_3$-C$_{10}$ cycloalkyl substituted phenyl, substituted pyridinyl, substituted pyrazolyl substituted piperazinyl, substituted morpholinyl, substituted piperidinyl, substituted pyrrolidinyl, or substituted tetrahydrofuryl, where W is a substituted group, it is substituted by one or more substituents which are each, independently, —CN, —CO$_2$R$^7$, —C(O)R$^7$, —C(O)NR$^7$R$^7$, —OW, —SR$^7$, —NR$^7$R$^7$, —NO$_2$, —NR$^7$C(O)R$^7$, —NR$^7$C(O)OR$^7$ or halogen.

13. A compound as in claim 12 wherein the cyclic structures of B and L bound directly to D are substituted in the ortho position by hydrogen.

14. A compound of claim 12 wherein B of Formula I is a substituted pyridyl, substituted quinolinyl or isoquinolinyl group substituted 1 to 3 times by 1 or more substituents which are each independently —CN, halogen, C$_1$-C$_{10}$ alkyl, C$_1$-C$_{10}$ alkoxy, —OH, up to per halo substituted C$_1$-C$_{10}$ alkyl, up to per halo substituted C$_1$-C$_{10}$ alkoxy or phenyl substituted by halogen up to per halo.

15. A compound of claim 12 wherein L$^1$ is additionally substituted 1 to 3 times by one or more substituents which are each, independently, C$_1$-C$_{10}$ alkyl, up to per halo substituted C$_1$-C$_{10}$ alkyl, —CN, —OH, halogen, C$_1$-C$_{10}$ alkoxy or up to per halo substituted C$_1$-C$_{10}$ alkoxy.

16. A compound as in claim 12 wherein substituents for B and L and additional substituents for L$^1$, are each, independently, C$_1$-C$_{10}$ alkyl, up to per halo substituted C$_1$-C$_{10}$ alkyl, CN, OH, halogen, C$_1$-C$_{10}$ alkoxy or up to per halo substituted C$_1$-C$_{10}$ alkoxy.

17. A compound of claim 12 which is a pharmaceutically acceptable salt of a compound of formula I which is
a) a basic salt of an organic acid or inorganic acid which is hydrochloric acid, hydrobromic acid, sulfuric acid, phosphoric acid, methanesulfonic acid, trifluorosulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, or mandelic acid; and
b) an acid salt of an organic or inorganic base containing a cation which is an alkaline cation, alkaline earth cation, the ammonium cation, an aliphatic substituted ammonium cation or an aromatic substituted ammonium cation.

18. A pharmaceutical composition comprising a compound of claim 12 or a pharmaceutically acceptable salt of a compound of formula I, and a physiologically acceptable carrier.

* * * * *

UNITED STATES PATENT AND TRADEMARK OFFICE
CERTIFICATE OF CORRECTION

| | |
|---|---|
| PATENT NO. | : 7,928,239 B2 |
| APPLICATION NO. | : 09/777920 |
| DATED | : April 19, 2011 |
| INVENTOR(S) | : Jacques Dumas et al. |

It is certified that error appears in the above-identified patent and that said Letters Patent is hereby corrected as shown below:

On Front Page:

Section (57) reads: "This invention relates to the use of a group of aryl ureas in treating raf mediated diseases, and pharmaceutical compositions in such therapy."

Should read: -- This invention relates to the use of a group of aryl ureas in treating raf mediated diseases, and pharmaceutical compositions for use in such therapy. --

In the Claims:

Column 101, line 44: replace with:

are hereby corrected as shown below:

$-C(O)-R^7$, $-NO_2$, $-OR^7$, $-SR^7$, $-NR^7R^7$,

Column 101, line 57: replace with:

are hereby corrected as shown below:

$-CN$, $-CO_2R^7$, $-C(O)R^7$, $-C(O)NR^7R^7$, $-OR^7$,

Column 101, line 58: replace with:

are hereby corrected as shown below:

$SR^7$, $-NR^7R^7$, $-NO_2$, $-NR^7C(O)R^7$, $-NR^7C$

Signed and Sealed this
Twenty-fourth Day of July, 2012

David J. Kappos
*Director of the United States Patent and Trademark Office*

CERTIFICATE OF CORRECTION (continued)
U.S. Pat. No. 7,928,239 B2

Column 107, Lines 40-41: replace with:

are hereby corrected as shown below:

wherein each W is independently -CN, -CO$_2$R$^7$, -C(O)NR$^7$R$^7$, -C(O)-R$^7$, -NO$_2$, -OR$^7$, -SR$^7$,

Column 108, Line 6: replace with:

are hereby corrected as shown below:

NR$^7$R$^7$, -OR$^7$, -SR$^7$, -NR$^7$R$^7$, -NO$_2$, -NR$^7$C(O)